US007101898B2

(12) United States Patent
Peschke et al.

(10) Patent No.: US 7,101,898 B2
(45) Date of Patent: Sep. 5, 2006

(54) AMIDES OF AMINOALKYL-SUBSTITUTED AZETIDINES, PYRROLIDINES, PIPERIDINES AND AZEPANES

(75) Inventors: Bernd Peschke, Malev (DK); Ingrid Pettersson, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/354,341

(22) Filed: Jan. 30, 2003

(65) Prior Publication Data

US 2003/0195190 A1  Oct. 16, 2003

Related U.S. Application Data

(60) Provisional application No. 60/354,192, filed on Feb. 4, 2002, provisional application No. 60/416,567, filed on Oct. 7, 2002.

(30) Foreign Application Priority Data

| Feb. 1, 2002 | (DK) | ................................ 2002 00160 |
| Oct. 7, 2002 | (DK) | ................................ 2002 01501 |

(51) Int. Cl.
*A61K 31/445* (2006.01)
*C07D 401/04* (2006.01)

(52) U.S. Cl. ...................................... 514/326; 546/208
(58) Field of Classification Search ................ 514/326; 546/208
See application file for complete search history.

(56) References Cited

U.S. PATENT DOCUMENTS

| 6,110,922 A | * | 8/2000 | Link et al. ............... 514/266.3 |
| 6,140,330 A | * | 10/2000 | Mori et al. ............... 514/254.03 |
| 6,316,475 B1 | | 11/2001 | Bennani et al. ............ 514/343 |
| 6,417,218 B1 | * | 7/2002 | Dorwald et al. ............ 514/399 |
| 2001/0039286 A1 | | 11/2001 | Dinnell et al. ............. 514/320 |
| 2002/0042420 A1 | | 4/2002 | Briem et al. ............ 514/253.04 |

FOREIGN PATENT DOCUMENTS

| WO | WO 97/40051 A1 | 10/1997 |
| WO | WO 97/43282 A2 | 11/1997 |
| WO | WO 00/39081 A2 | 7/2000 |
| WO | WO 00/59880 A1 | 10/2000 |
| WO | WO 01/44191 A1 | 6/2001 |
| WO | WO 01/66534 A2 | 9/2001 |
| WO | WO 01/74810 A2 | 10/2001 |
| WO | WO 01/94353 A1 | 12/2001 |
| WO | WO 02/34718 A1 | 5/2002 |

OTHER PUBLICATIONS

Bakeer Botts "In Print, reach through claims" Attorney's practice profiles new & events (2002).*
Linney et al., J. Med. Chem., vol. 43, pp. 2362-2370 (2000).

* cited by examiner

*Primary Examiner*—Celia Chang
(74) *Attorney, Agent, or Firm*—Rosemarie R. Wilk-Drescan; Reza Green; Richard W. Bork

(57) ABSTRACT

Novel amides of aminoalkyl-substituted azetidines, pyrrolidines, piperidines and azepanes, use of these compounds as pharmaceutical compositions, pharmaceutical compositions comprising the compounds, and a method of treatment employing these compounds and compositions. The compounds show a high and selective binding affinity to the histamine H3 receptor indicating histamine H3 receptor antagonistic, inverse agonistic or agonistic activity. As a result, the compounds are useful for the treatment of diseases and disorders related to the histamine H3 receptor.

30 Claims, No Drawings

AMIDES OF AMINOALKYL-SUBSTITUTED AZETIDINES, PYRROLIDINES, PIPERIDINES AND AZEPANES

CROSS-REFERENCE TO RELATED APPLICATIONS

This application claims priority under 35 U.S.C. 119 of Danish application nos. PA 2002 00160 and PA 2002 01501 filed Feb. 1, 2002 and Oct. 7, 2002 respectively, and U.S. provisional application Nos. 60/354,192 and 60/416,567 filed on Feb. 4, 2002 and Oct. 7, 2002 respectively, the contents of which are fully incorporated herein by reference.

FIELD OF THE INVENTION

The present invention relates to novel amides of aminoalkyl-substituted azetidines, pyrrolidines, piperidines and azepanes, to the use of these compounds as pharmaceutical compositions, to pharmaceutical compositions comprising the compounds, and to a method of treatment employing these compounds and compositions. The present compounds show a high and selective binding affinity to the histamine H3 receptor indicating histamine H3 receptor antagonistic, inverse agonistic or agonistic activity. As a result, the compounds are useful for the treatment of diseases and disorders related to the histamine H3 receptor.

BACKGROUND OF THE INVENTION

The existence of the histamine H3 receptor has been known for several years and the receptor is of current interest for the development of new medicaments. Recently, the human histamine H3 receptor has been cloned. The histamine H3 receptor is a presynaptic autoreceptor located both in the central and the peripheral nervous system, the skin and in organs such as the lung, the intestine, probably the spleen and the gastrointestinal tract. Recent evidence suggests that the H3 receptor shows intrinsic, constitutive activity, in vitro as well as in vivo (i.e. it is active in the absence of an agonist). Compounds acting as inverse agonists can inhibit this activity. The histamine H3 receptor has been demonstrated to regulate the release of histamine and also of other neurotransmitters such as serotonin and acetylcholine. A histamine H3 receptor antagonist or inverse agonist would therefore be expected to increase the release of these neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists and antagonists could be important mediators of neuronal activity. Accordingly, the histamine H3 receptor is an important target for new therapeutics.

Compounds similar to the compounds of the present invention have previously been prepared, and their biological properties have been investigated, cf. WO 00/59880, WO 00/39081. However, these references neither disclose nor suggest that these compounds may have a histamine H3 receptor antagonistic or agonistic activity.

Several publications disclose the preparation and use of histamine H3 agonists and antagonists. Most of these are imidazole derivatives. However, recently some imidazole-free ligands of the histamine H3 receptor have been described (see e.g. Linney et al., *J. Med. Chem.* 2000, 43, 2362–2370; U.S. Pat. No. 6,316,475, WO 01/66534 and WO 01/74810). However, these compounds differ structurally from the present compounds.

In view of the art's interest in histamine H3 receptor agonists, inverse agonists and antagonists, novel compounds which interact with the histamine H3 receptor would be a highly desirable contribution to the art.

SUMMARY OF THE INVENTION

The present invention provides a novel class of amides of aminoalkyl-substituted azetidines, pyrrolidines, piperidines and azepanes that has a high and specific affinity to the histamine H3 receptor.

Due to their interaction with the histamine H3 receptor, the present compounds are useful in the treatment of a wide range of conditions and disorders in which an interaction with the histamine H3 receptor is beneficial. Thus, the compounds may find use e.g. in the treatment of diseases of the central nervous system, the peripheral nervous system, the cardiovascular system, the pulmonary system, the gastrointestinal system and the endocrinological system.

Definitions

In the structural formulae given herein and throughout the present specification, the following terms have the indicated meaning:

The term "halogen" means F, Cl, Br or I.

The term "$C_{1-6}$-alkyl" as used herein represents a saturated, branched or straight hydrocarbon group having from 1 to 6 carbon atoms. Typical $C_{1-6}$-alkyl groups include, but are not limited to, methyl, ethyl, n-propyl, isopropyl, butyl, isobutyl, sec-butyl, tert-butyl, pentyl, isopentyl, hexyl, isohexyl and the like.

The term "$C_{2-6}$-alkenyl" as used herein represents a branched or straight hydrocarbon group having from 2 to 6 carbon atoms and at least one double bond. Examples of such groups include, but are not limited to, ethenyl, 1-propenyl, 2-propenyl, isopropenyl, 1,3-butadienyl, 1-butenyl, 2-butenyl, 1-pentenyl, 2-pentenyl, 1-hexenyl, 2-hexenyl and the like.

The term "$C_{2-6}$-alkynyl" as used herein represents a branched or straight hydrocarbon group having from 2 to 6 carbon atoms and at least one triple bond. Examples of such groups include, but are not limited to, ethynyl, 1-propynyl, 2-propynyl, 1-butynyl, 2-butynyl, 1-pentynyl, 2-pentynyl, 1-hexynyl, 2-hexynyl and the like.

The term "$C_{3-6}$-alkylene" as used herein represent a saturated, divalent, branched or straight hydrocarbon group having from 3 to 6 carbon atoms. Typical $C_{3-6}$-alkylene groups include, but are not limited to, 1,2-propylene, 1,3-propylene, butylene, isobutylidene, pentylene, hexylene and the like.

The term "$C_{3-6}$-alkenylene" as used herein represent a divalent, branched or straight hydrocarbon group having from 3 to 6 carbon atoms and at least one double bond. Typical $C_{3-6}$-alkenylene groups include, but are not limited to, n-propenylene, butenylene, pentenylene, hexenylene and the like.

The term "$C_{1-6}$-alkoxy" as used herein refers to the radical —O—$C_{1-6}$-alkyl, wherein $C_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "$C_{1-6}$-alkylthio" as used herein refers to the radical —S—$C_{1-6}$-alkyl, wherein $C_{1-6}$-alkyl is as defined above. Representative examples are methylthio, ethylthio, isopropylthio, n-propylthio, butylthio, pentylthio and the like.

The term "$C_{1-6}$-alkylsulfinyl" as used herein refers to the radical —S(=O)—$C_{1-6}$-alkyl, wherein $C_{1-6}$-alkyl is as defined above. Representative examples are methylsulfinyl, ethylsulfinyl, isopropylsulfinyl, n-propylsulfinyl, butylsulfinyl, pentylsulfinyl and the like.

The term "$C_{1-6}$-alkylsulfonyl" as used herein refers to the radical —S(=O)$_2$—$C_{1-6}$-alkyl, wherein $C_{1-6}$-alkyl is as defined above. Representative examples are methylsulfonyl, ethylsulfonyl, isopropylsulfonyl, n-propylsulfonyl, butylsulfonyl, pentylsulfonyl and the like.

The term "$C_{1-7}$-alkanoyl" as used herein refers to the radical —C(=O)H or —C(=O)$C_{1-6}$-alkyl, wherein $C_{1-6}$-alkyl is as defined above. Representative examples are formyl, acetyl, propionyl, butanoyl, pentanoyl, hexanoyl, heptanoyl and the like.

The term "$C_{1-6}$-alkylcarbamoyl" as used herein refers to the radical —C(=O)NH—$C_{1-6}$-alkyl, wherein $C_{1-6}$-alkyl is as defined above. Representative examples are methylcarbamoyl, ethylcarbamoyl, isopropylcarbamoyl, n-propylcarbamoyl, butylcarbamoyl, pentylcarbamoyl, hexylcarbamoyl and the like.

The term "di-$C_{1-6}$-alkylcarbamoyl" as used herein refers to the radical —C(=O)N($C_{1-6}$-alkyl)$_2$, wherein $C_{1-6}$-alkyl is as defined above. It should be understood that the $C_{1-6}$-alkyl groups may be the same or different. Representative examples are dimethylcarbamoyl, methylethylcarbamoyl, diethylcarbamoyl, diisopropylcarbamoyl, di-n-propylcarbamoyl, dibutylcarbamoyl, dipentylcarbamoyl, dihexylcarbamoyl and the like.

The term "$C_{3-8}$-cycloalkyl" as used herein represents a monocyclic, carbocyclic group having from from 3 to 8 carbon atoms. Representative examples are cyclopropyl, cyclobutyl, cyclopentyl, cyclohexyl, cycloheptyl, cyclooctyl and the like.

The term "$C_{5-8}$-cycloalkenyl" as used herein represents a monocyclic, carbocyclic, non-aromatic group having from 5 to 8 carbon atoms and at least one double bond. Representative examples are cyclopentenyl, cyclohexenyl, cycloheptenyl, cyclooctenyl, and the like.

The term "$C_{3-8}$-cycloalkanoyl" as used herein refers to the radical —C(=O)—$C_{3-8}$-cycloalkyl, wherein $C_{3-8}$-cycloalkyl is as defined above. Representative examples are cyclopropanoyl, cyclobutanoyl, cyclopentanoyl, cyclohexanoyl, cycloheptanoyl, cyclooctanoyl, and the like.

The term "$C_{3-8}$-cycloalkylcarbamoyl" as used herein refers to the radical —C(=O)NH—$C_{3-8}$-cycloalkyl, wherein $C_{3-8}$-cycloalkyl is as defined above. Representative examples are cyclopropylcarbamoyl, cyclobutylcarbamoyl, cyclopentylcarbamoyl, cyclohexylcarbamoyl, cycloheptylcarbamoyl, cyclooctylcarbamoyl, and the like.

The term "$C_{3-8}$-cycloalkyl-oxycarbonyl" as used herein refers to the radical —C(=O)—O—$C_{3-8}$-cycloalkyl, wherein $C_{3-8}$-cycloalkyl is as defined above. Representative examples are cyclopropyloxycarbonyl, cyclobutyloxycarbonyl, cyclopentyloxycarbonyl, cyclohexyloxycarbonyl, cycloheptyloxycarbonyl, cyclooctyloxycarbonyl, and the like.

The term "aryl" as used herein is intended to include carbocyclic aromatic ring systems such as phenyl, biphenylyl, naphthyl, anthracenyl, phenanthrenyl, fluorenyl, indenyl, pentalenyl, azulenyl and the like. Aryl is also intended to include the partially hydrogenated derivatives of the carbocyclic systems enumerated above. Non-limiting examples of such partially hydrogenated derivatives are 1,2,3,4-tetrahydronaphthyl, 1,4-dihydronaphthyl and the like.

The term "aryloxy" as used herein refers to the radical —O-aryl, wherein aryl is as defined above. Non-limiting examples are phenoxy, naphthoxy, anthracenyloxy, phenantrenyloxy, fluorenyloxy, indenyloxy and the like.

The term "aroyl" as used herein refers to the radical —C(=O)-aryl, wherein aryl is as defined above. Non-limiting examples are benzoyl, naphthoyl, anthracenylcarbonyl, phenantrenylcarbonyl, fluorenylcarbonyl, indenylcarbonyl and the like.

The term "arylthio" as used herein refers to the radical —S-aryl, wherein aryl is as defined above. Non-limiting examples are phenoxy, naphthoxy, anthracenylthio, phenantrenylthio, fluorenylthio, indenylthio and the like.

The term "arylsulfinyl" as used herein refers to the radical —S(=O)-aryl, wherein aryl is as defined above. Non-limiting examples are phenylsulfinyl, naphthylsulfinyl, anthracenylsulfinyl, phenantrenylsulfinyl, fluorenylsulfinyl, indenylsulfinyl and the like.

The term "arylsulfonyl" as used herein refers to the radical —S(=O)$_2$-aryl, wherein aryl is as defined above. Non-limiting examples are phenylsulfonyl, naphthylsulfonyl, anthracenylsulfonyl, phenantrenylsulfonyl, fluorenylsulfonyl, indenylsulfonyl and the like.

The term "heteroaryl" as used herein is intended to include heterocyclic aromatic ring systems containing one or more heteroatoms selected from nitrogen, oxygen and sulfur such as furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzothiazolyl, benzoisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, pyrrolinyl, pyrazolinyl, indanyl, indolinyl, oxazolidinyl, oxazolinyl, oxazepinyl and the like.

The term "heteroaroyl" as used herein refers to the radical —C(=O)-heteroaryl, wherein heteroaryl is as defined above.

The term "heteroaryloxy" as used herein refers to the radical —O-heteroaryl, wherein heteroaryl is as defined above.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

DESCRIPTION OF THE INVENTION

The present invention relates to a compound of the general formula (I):

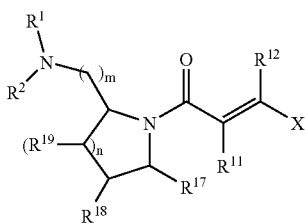

(I)

wherein
m is 1, 2 or 3,
n is 0, 1, 2 or 3,
$R^1$ and $R^2$ independently are hydrogen,
$C_{1-6}$-alkyl, $C_{2-6}$-alkenyl or $C_{2-6}$-alkynyl, which may optionally be substituted with one or more substituents selected from $C_{3-8}$-cycloalkyl, $C_{5-8}$-cycloalkenyl, halogen and hydroxyl, or
$C_{3-8}$-cycloalkyl or $C_{5-8}$-cycloalkenyl, which may optionally be substituted with one or more substituents selected from halogen, hydroxyl, $C_{1-6}$-alkyl, $C_{2-6}$-alkenyl and $C_{2-6}$-alkynyl,
or $R^1$ and $R^2$ together form a $C_{3-6}$-alkylene bridge or a $C_{3-6}$-alkenylene bridge, which may optionally be substituted with one or more substituents selected from halogen and hydroxyl,
$R^{11}$ and $R^{12}$ independently are hydrogen,
$C_{1-6}$-alkyl, which may optionally be substituted with one or more substituents selected from $C_{3-8}$-cycloalkyl, $C_{5-8}$-cycloalkenyl, halogen and hydroxyl, or
$C_{3-8}$-cycloalkyl or $C_{5-8}$-cycloalkenyl, which may optionally be substituted with one or more substituents selected from halogen and hydroxyl,
X is

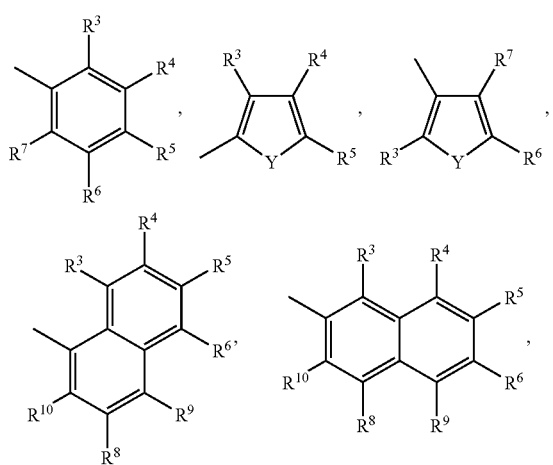

-continued

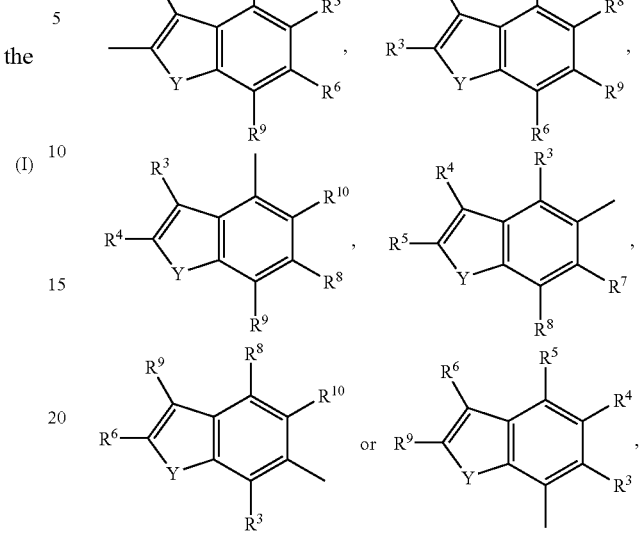

$R^3$, $R^4$, $R^5$, $R^6$, $R^7$, $R^8$, $R^9$ and $R^{10}$ independently are
hydrogen, halogen, cyano, —$NR^{15}R^{16}$, hydroxyl, carbamoyl, carboxyl, —$CF_3$, —$OCF_3$, carboxyl, amidino, guanidino or nitro, or
$C_{1-6}$-alkoxy, $C_{1-6}$-alkyl, $C_{1-7}$-alkanoyl, $C_{1-6}$-alkylcarbamoyl, di-$C_{1-6}$-alkylcarbamoyl, $C_{1-6}$-alkyloxycarbonyl, $C_{1-6}$-alkylthio, $C_{1-6}$-alkylsulfinyl, $C_{1-6}$-alkylsulfonyl, aryl, aroyl, aryloxy, aryloxycarbonyl, arylthio, arylsulfinyl or arylsulfonyl, which may optionally be substituted with one or more substituents selected from halogen, hydroxyl, cyano and —$NR^{15}R^{16}$,
$R^{15}$ and $R^{16}$ independently are
hydrogen or carbamoyl,
$C_{1-6}$-alkyl, which may optionally be substituted with one or more substituents selected from $C_{3-8}$-cycloalkyl, $C_{5-8}$-cycloalkenyl, halogen, hydroxyl, cyano and amino, or
$C_{3-8}$-cycloalkyl, $C_{5-8}$-cycloalkenyl, $C_{1-6}$-alkylcarbamoyl, di-$C_{1-6}$-alkylcarbamoyl or $C_{1-6}$-alkyloxycarbonyl, which may optionally be substituted with one or more substituents selected from halogen, hydroxyl, cyano, amino, $C_{1-6}$-alkyl, $C_{2-6}$-alkenyl and $C_{2-6}$-alkynyl,
or $R^{15}$ and $R^{16}$ together form a $C_{3-6}$-alkylene bridge or a $C_{3-6}$-alkenylene bridge, which may optionally be substituted with one or more substituents selected from halogen and hydroxyl,
or two or more of $R^3$ and $R^4$, $R^4$ and $R^5$, $R^5$ and $R^6$, $R^6$ and $R^7$, $R^7$ and $R^8$, $R^8$ and $R^9$, $R^9$ and $R^6$, and $R^8$ and $R^{10}$ together form a bridge selected from —$OCH_2O$—, —$OCH_2CH_2O$—, —$OCH_2CH_2CH_2O$— and $C_{3-5}$-alkylene,
or $R^{11}$ and $R^3$, $R^{11}$ and $R^7$, or $R^{11}$ and $R^{10}$ together form a bridge selected from —O—, —S—, —$CH_2$—, —C(=O)—, —CH(OH)—, —$NR^{13}$—, —$OCH_2$— and —$CH_2O$—,
$R^{13}$ is hydrogen,
$C_{1-6}$-alkyl, which may optionally be substituted with one or more substituents selected from $C_{3-8}$-cycloalkyl, $C_{5-8}$-cycloalkenyl, halogen, hydroxyl, cyano and amino, $C_{3-8}$-cycloalkyl or $C_{5-8}$-cycloalkenyl, which may optionally be substituted with one or more substituents selected from halogen, hydroxyl, cyano, amino, $C_{1-6}$-alkyl, $C_{2-6}$-alkenyl and $C_{2-6}$-alkynyl, —Y— is —$CH_2$—, —C(=O)—, —$NR^{14}$—, —O—, —S—, —$CH_2O$—, —$OCH_2$— or —CH(OH)—, $R^{14}$ is hydrogen, $C_{1-6}$-alkyl, which may optionally be substituted with one or more substituents selected from $C_{3-8}$-cycloalkyl, $C_{5-8}$-cycloalkenyl, halogen, hydroxyl, cyano and amino, $C_{3-8}$-cycloalkyl or $C_{5-8}$-cycloalkenyl, which may optionally be substituted with one or more substituents selected from halogen, hydroxyl, cyano and amino, $R^{17}$ is hydrogen, $C_{1-6}$-alkyl, $C_{2-6}$-alkenyl or $C_{2-6}$-alkynyl, $R^{18}$ and $R^{19}$ independently are hydrogen, halogen, hydroxyl, amino, $C_{1-6}$-alkyl, $C_{2-6}$-alkenyl or $C_{2-6}$-alkynyl, as well as any diastereomer or enantiomer or tautomeric form thereof including mixtures of these or a pharmaceutically acceptable salt thereof.

In one embodiment $R^{17}$, $R^{18}$ and $R^{19}$ are all hydrogen.

In another embodiment m is 1.

In still another embodiment n is 1.

In yet another embodiment $R^1$ and $R^2$ together form a $C_{3-6}$-alkylene bridge, which may optionally be substituted with one or more substituents selected from halogen and hydroxyl.

In one embodiment $R^1$ and $R^2$ together form a $C_4$-alkylene bridge, which may optionally be substituted with one or more substituents selected from halogen and hydroxyl.

In a further embodiment $R^1$ and $R^2$ together form a $C_4$-alkylene bridge.

In still a further embodiment $R^{11}$ is hydrogen.

In yet a further embodiment $R^{12}$ is hydrogen.

In another embodiment X is

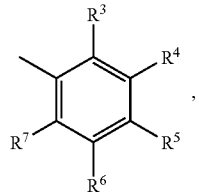

wherein $R^3$, $R^4$, $R^5$, $R^6$ and $R^7$ are as defined for formula (I).

In one embodiment $R^3$, $R^4$, $R^5$, $R^6$ and $R^7$ are independently selected from hydrogen, halogen, —$CF_3$ and $C_{1-6}$-alkoxy.

In a further embodiment four of the substituents $R^3$, $R^4$, $R^5$, $R^6$ and $R^7$ are hydrogen and the remaining substituent is selected from halogen, —$CF_3$ and $C_{1-6}$-alkoxy.

It should be understood that when n is 2 or 3, the $R^{19}$ groups may be the same or different.

In another aspect the invention provides compounds of the general formula (II):

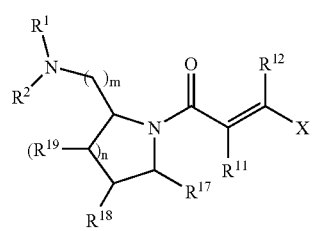

(II)

wherein m is 1, 2 or 3, n is 0, 1, 2 or 3, $R^1$ and $R^2$ independently are hydrogen, $C_{1-6}$-alkyl, $C_{2-6}$-alkenyl or $C_{2-6}$-alkynyl, which may optionally be substituted with one or more substituents selected from $C_{3-8}$-cycloalkyl, $C_{5-8}$-cycloalkenyl, halogen and hydroxyl, or $C_{3-8}$-cycloalkyl or $C_{5-8}$-cycloalkenyl, which may optionally be substituted with one or more substituents selected from halogen, hydroxyl, $C_{1-6}$-alkyl, $C_{2-6}$-alkenyl and $C_{2-6}$-alkynyl, or $R^1$ and $R^2$ together form a $C_{3-6}$-alkylene bridge or a $C_{3-6}$-alkenylene bridge, which may optionally be substituted with one or more substituents selected from halogen and hydroxyl, $R^{11}$ and $R^{12}$ independently are hydrogen, $C_{1-6}$-alkyl, which may optionally be substituted with one or more substituents selected from $C_{3-8}$-cycloalkyl, $C_{5-8}$-cycloalkenyl, halogen and hydroxyl, or $C_{3-8}$-cycloalkyl or $C_{5-8}$-cycloalkenyl, which may optionally be substituted with one or more substituents selected from halogen and hydroxyl, X is

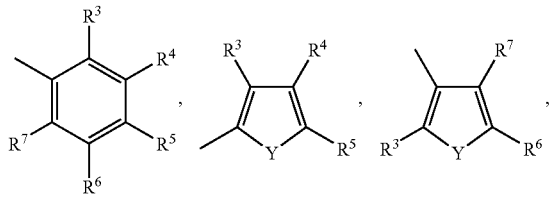

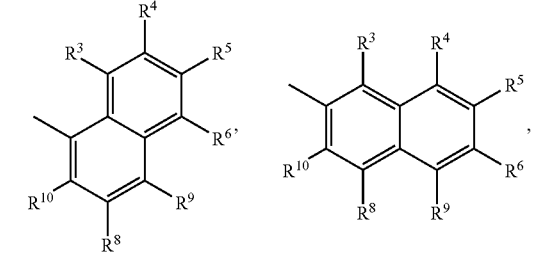

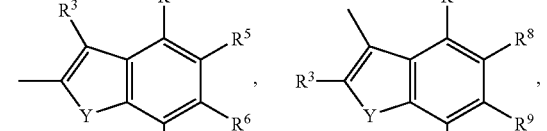

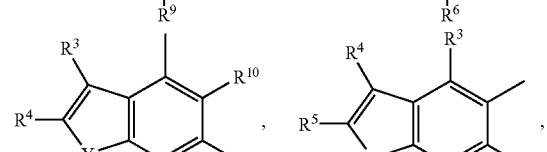

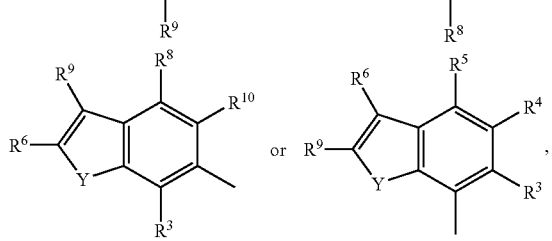

$R^3$, $R^4$, $R^5$, $R^6$, $R^7$, $R^8$, $R^9$ and $R^{10}$ independently are
hydrogen, halogen, cyano, —$NR^{15}R^{16}$, hydroxyl, carbamoyl, carboxyl, —$CF_3$, —$OCF_3$, carboxyl, amidino, guanidino or nitro, or $C_{1-6}$-alkoxy, $C_{1-6}$-alkyl, $C_{1-7}$-alkanoyl, $C_{1-6}$-alkylcarbamoyl, di-$C_{1-6}$-alkylcarbamoyl, $C_{1-6}$-alkyloxycarbonyl, $C_{3-8}$-cycloalkyl, $C_{3-8}$-cycloalkanoyl, $C_{3-8}$-cycloalkylcarbamoyl, $C_{3-8}$-cycloalkyl-oxycarbonyl, $C_{1-6}$-alkylthio, $C_{1-6}$-alkylsulfinyl, $C_{1-6}$-alkylsulfonyl, $C_{1-6}$-alkylsulfonyl-O—, aryl, aroyl, aryloxy, aryloxycarbonyl, arylthio, arylsulfanyl, arylsulfanyl, heteroaryl, heteroaroyl, or heteroaryloxy which may optionally be substituted with one or more substituents selected from halogen, hydroxyl, cyano and —$NR^{15}R^{16}$, $R^{15}$ and $R^{16}$ independently are
hydrogen or carbamoyl, $C_{1-6}$-alkyl, which may optionally be substituted with one or more substituents selected from $C_{3-8}$-cycloalkyl, $C_{5-8}$-cycloalkenyl, halogen, hydroxyl, cyano and amino, or $C_{3-8}$-cycloalkyl, $C_{5-8}$-cycloalkenyl, $C_{1-6}$-alkylcarbamoyl, di-$C_{1-6}$-alkylcarbamoyl or $C_{1-6}$-alkyloxycarbonyl, which may optionally be substituted with one or more substituents selected from halogen, hydroxyl, cyano, amino, $C_{1-6}$-alkyl, $C_{2-6}$-alkenyl and $C_{2-6}$-alkynyl, or $R^{15}$ and $R^{16}$ together form a $C_{3-6}$-alkylene bridge or a $C_{3-6}$-alkenylene bridge, which may optionally be substituted with one or more substituents selected from halogen and hydroxyl, or two or more of $R^3$ and $R^4$, $R^4$ and $R^5$, $R^5$ and $R^6$, $R^6$ and $R^7$, $R^7$ and $R^8$, $R^8$ and $R^9$, $R^9$ and $R^6$, and $R^8$ and $R^{10}$ together form a bridge selected from —$OCH_2O$—, —$OCH_2CH_2O$—, —$OCH_2CH_2CH_2O$— and $C_{3-5}$-alkylene, or $R^{11}$ and $R^3$, $R^{11}$ and $R^7$, or $R^{11}$ and $R^{10}$ together form a bridge selected from —O—, —S—, —$CH_2$—, —C(=O)—, —CH(OH)—, —$NR^{13}$—, —$OCH_2$— and —$CH_2O$—, $R^{13}$ is hydrogen,
$C_{1-6}$-alkyl, which may optionally be substituted with one or more substituents selected from $C_{3-8}$-cycloalkyl, $C_{5-8}$-cycloalkenyl, halogen, hydroxyl, cyano and amino, $C_{3-8}$-cycloalkyl or $C_{5-8}$-cycloalkenyl, which may optionally be substituted with one or more substituents selected from halogen, hydroxyl, cyano, amino, $C_{1-6}$-alkyl, $C_{2-6}$-alkenyl and $C_{2-6}$-alkynyl, —Y— is —$CH_2$—, —C(=O)—, —$NR^{14}$—, —O—, —S—, —$CH_2O$—, —$OCH_2$— or —CH(OH)—, $R^{14}$ is hydrogen,
$C_{1-6}$-alkyl, which may optionally be substituted with one or more substituents selected from $C_{3-8}$-cycloalkyl, $C_{5-8}$-cycloalkenyl, halogen, hydroxyl, cyano and amino, $C_{3-8}$-cycloalkyl or $C_{5-8}$-cycloalkenyl, which may optionally be substituted with one or more substituents selected from halogen, hydroxyl, cyano and amino, $R^{17}$ is hydrogen, $C_{1-6}$-alkyl, $C_{2-6}$-alkenyl or $C_{2-6}$-alkynyl,
$R^{18}$ and $R^{19}$ independently are hydrogen, halogen, hydroxyl, amino, $C_{1-6}$-alkyl, $C_{2-6}$-alkenyl or $C_{2-6}$-alkynyl, as well as any diastereomer or enantiomer or tautomeric form thereof including mixtures of these or a pharmaceutically acceptable salt thereof.

In another embodiment $R^1$ is hydrogen,
$C_{1-6}$-alkyl optionally substituted with one or more substituents selected from $C_{3-8}$-cycloalkyl, $C_{5-8}$-cycloalkenyl, halogen and hydroxyl, or $R^1$ and $R^2$ together form a $C_{3-6}$-alkylene bridge or a $C_{3-6}$-alkenylene bridge, which may optionally be substituted with one or more substituents selected from halogen and hydroxyl In another embodiment $R^1$ is
$C_{1-6}$-alkyl, or
$R^1$ and $R^2$ together form a $C_{3-6}$-alkylene bridge or a $C_{3-6}$-alkenylene bridge, which may optionally be substituted with one or more substituents selected from halogen and hydroxyl In another embodiment $R^1$ is
$C_{1-6}$-alkyl, or
$R^1$ and $R^2$ together form a $C_{3-6}$-alkylene bridge, which may optionally be substituted with one or more substituents selected from halogen and hydroxyl In another embodiment $R^1$ is
$C_{1-6}$-alkyl, or
$R^1$ and $R^2$ together form a $C_{4-5}$-alkylene bridge, which may optionally be substituted with one or more substituents selected from halogen and hydroxyl In another embodiment $R^1$ is
$C_{1-6}$-alkyl, or
$R^1$ and $R^2$ together form a $C_{4-5}$-alkylene bridge In another embodiment $R^1$ and $R^2$ together form a $C_{4-5}$-alkylene bridge In another embodiment $R^1$ and $R^2$ together form a $C_4$-alkylene bridge In another embodiment $R^1$ and $R^2$ together form a $C_5$-alkylene bridge In another embodiment m is 1

In another embodiment n is 1 or 2

In another embodiment n is 1

In another embodiment X is

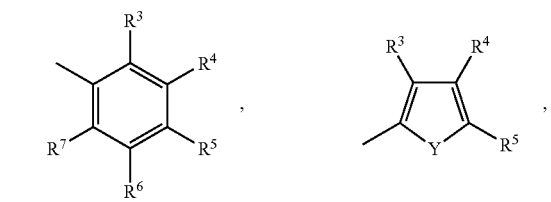

wherein $R^3$, $R^4$, $R^5$, $R^6$ and $R^7$ are as defined in claim 1
In another embodiment —Y— is —O— or —S—
In another embodiment —Y— is —O—
In another embodiment X is

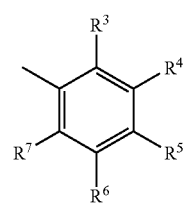

wherein $R^3$, $R^4$, $R^5$, $R^6$ and $R^7$ are as defined in claim 1

In another embodiment $R^3$, $R^4$, $R^5$, $R^6$ and $R^7$ are independently selected from hydrogen, halogen, cyano, —$NR^{15}R^{16}$, —$CF_3$, —$OCF_3$, or nitro, wherein $R^{15}$ and $R^{16}$ are as defined in claim 1
$C_{1-6}$-alkoxy, $C_{3-6}$-cycloalkyl-carbonyl, aryl, heteroaryl, $C_{3-8}$-cycloalkanoyl, $C_{1-6}$-alkylsulfonyl, or $C_{1-6}$-alkylsulfonyl-O— which may optionally be substituted with one or more halogen or $R^4$ and $R^5$ together form a —$OCH_2O$— bridge, or $R^{11}$ and $R^3$ together form a bridge selected from —O— or —S—

In another embodiment $R^3$, $R^4$, $R^5$, $R^6$ and $R^7$ are independently selected from hydrogen, halogen, cyano, —$CF_3$, or —$OCF_3$
$C_{1-6}$-alkoxy, 1,2,4-triazolyl, cyclopropanoyl or $C_{1-6}$-alkylsulfonyl-O— which may optionally be substituted with one or more halogen or $R^4$ and $R^5$ together form a —$OCH_2O$— bridge, or $R^{11}$ and $R^3$ together form a bridge selected from —O— or —S—

In another embodiment $R^3$, $R^4$, $R^5$, $R^6$ and $R^7$ are independently selected from hydrogen, halogen, cyano, —$CF_3$, or —$OCF_3$
—O—$CH_3$, 1,2,4-triazolyl, —O—$CH_2CH_3$, or $CH_3$-sulfonyl-O— which may optionally be substituted with one or more halogen or $R^{11}$ and $R^3$ together form a bridge selected from —O— or —S—

In another embodiment $R^3$, $R^4$, $R^5$, $R^6$ and $R^7$ are independently selected from hydrogen, halogen, cyano, —$CF_3$, or —$OCF_3$
—O—$CH_3$, —O—$CH_2CH_3$, or $CH_3$-sulfonyl-O— or $CF_3$-sulfonyl-O— or $R^{11}$ and $R^3$ together form a bridge selected from —O— or —S—

In another embodiment $R^{11}$ is hydrogen
In another embodiment $R^{12}$ is hydrogen or $C_{1-6}$-alkyl
In another embodiment $R^{12}$ is hydrogen or methyl
In another embodiment $R^{15}$ is hydrogen
In another embodiment $R^{16}$ is hydrogen
In another embodiment $R^{17}$, $R^{18}$ and $R^{19}$ are all hydrogen The compounds of the present invention may be chiral, and it is intended that any enantiomers, as separated, pure or partially purified enantiomers or racemic mixtures thereof are included within the scope of the invention.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention.

Furthermore, some of the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates, which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds of the present invention interact with the histamine H3 receptor and are accordingly useful for the treatment of a wide variety of conditions and disorders in which histamine H3 receptor interactions are beneficial.

Accordingly, in another aspect the present invention relates to a compound of the general formula (I) as well as any diastereomer or enantiomer or tautomeric form thereof including mixtures of these or a pharmaceutically acceptable salt thereof for use as a pharmaceutical composition.

The invention also relates to pharmaceutical compositions comprising, as an active ingredient, at least one compound of the formula (I) or any diastereomer or enantiomer or tautomeric form thereof including mixtures of these or a pharmaceutically acceptable salt thereof together with one or more pharmaceutically acceptable carriers or diluents.

Furthermore, the invention relates to the use of a compound of the general formula (I) as well as any diastereomer or enantiomer or tautomeric form thereof including mixtures of these or a pharmaceutically acceptable salt thereof for the preparation of a pharmaceutical composition for the treatment of disorders and diseases related to the histamine H3 receptor.

In still another aspect, the invention relates to a method for the treatment of diseases and disorders related to the histamine H3 receptor the method comprising administering to a subject in need thereof an effective amount of a compound of the formula (I) or any diastereomer or enantiomer or tautomeric form thereof including mixtures of these or a pharmaceutically acceptable salt thereof or a pharmaceutical composition comprising the same.

In one aspect the invention relates to compounds with histamine H3 receptor antagonistic activity or inverse agonistic activity which may accordingly be useful in the treatment of a wide range of conditions and disorders in which histamine H3 receptor blockade is beneficial.

In another aspect the invention relates to compounds with histamine H3 receptor agonistic activity and which may accordingly be useful in the treatment of a wide range of conditions and disorders in which histamine H3 receptor activation is beneficial.

In a preferred embodiment of the invention the present compounds are used for the preparation of a pharmaceutical composition for the reduction of weight.

In a preferred embodiment of the invention the present compounds are used for the preparation of a pharmaceutical composition for the treatment of overweight or obesity.

In another preferred embodiment of the invention the present compounds are used for the preparation of a pharmaceutical composition for the suppression of appetite or satiety induction.

In a further preferred embodiment of the invention the present compounds are used for the preparation of a pharmaceutical composition for the prevention and/or treatment of disorders and diseases related to overweight or obesity such as atherosclerosis, hypertension, IGT (impaired glucose tolerance), diabetes, especially type 2 diabetes (NIDDM (non-insulin dependent diabetes mellitus)), dyslipidaemia, coronary heart disease, gallbladder disease, osteoarthritis and various types of cancer such as endometrial, breast, prostate and colon cancers.

In yet a further preferred embodiment of the invention the present compounds are used for the preparation of a pharmaceutical composition for the prevention and/or treatment of eating disorders such as bulimia and binge eating.

In a further preferred embodiment of the invention the present compounds are used for the preparation of a pharmaceutical composition for the treatment of IGT.

In a further preferred embodiment of the invention the present compounds are used for the preparation of a pharmaceutical composition for the treatment of type 2 diabetes. Such treatment includes inter alia treatment for the purpose of delaying or prevention of the progression from IGT to type 2 diabetes as well as delaying or prevention of the progression from non-insulin requiring type 2 diabetes to insulin requiring type 2 diabetes.

The compounds of the present invention may also be used for the treatment of airway disorders such as asthma, as anti-diarrhoeals and for the modulation of gastric acid secretion.

Furthermore, the compounds of the present invention may be used for the treatment of diseases associated with the regulation of sleep and wakefulness and for the treatment of narcolepsy and attention deficit disorders.

Moreover, the compounds of the invention may be used as CNS stimulants or as sedatives. The present compounds may also be used for the treatment of conditions associated with epilepsy. Additionally, the present compounds may be used for the treatment of motion sickness and vertigo. Furthermore, they may be useful as regulators of hypothalamo-hypophyseal secretion, antidepressants, modulators of cerebral circulation, and in the treatment of irritable bowel syndrome.

Further, the compounds of the present invention may be used for the treatment of dementia and Alzheimer's disease.

The compounds of the present invention may also be useful for the treatment of allergic rhinitis, ulcer or anorexia.

The compounds of the present invention may furthermore be useful for the treatment of migraine, see McLeod et al., *The Journal of Pharmacology and Experimental Therapeutics* 287 (1998), 43–50, and for the treatment of myocardial infarction, see Mackins et al., *Expert Opinion on Investigational Drugs* 9 (2000), 2537–2542.

In a further aspect of the invention treatment of a patient with the present compounds is combined with diet and/or exercise.

In a further aspect of the invention the present compounds are administered in combination with one or more further active substances in any suitable ratio(s). Such further active agents may be selected from antiobesity agents, antidiabetics, antidyslipidemic agents, antihypertensive agents, agents for the treatment of complications resulting from or associated with diabetes and agents for the treatment of complications and disorders resulting from or associated with obesity.

Thus, in a further aspect of the invention the present compounds are administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, opioid antagonists (such as naltrexone), exendin-4, GLP-1 and ciliary neurotrophic factor.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

In still another embodiment the antiobesity agent is phendimetrazine, diethylpropion, fluoxetine, bupropion, topiramate or ecopipam.

In yet a further aspect the present compounds are administered in combination with one or more antidiabetic agents.

Relevant antidiabetic agents include insulin, insulin analogues and derivatives such as those disclosed in EP 0 792 290 (Novo Nordisk A/S), e.g. $N^{\epsilon B29}$-tetradecanoyl des (B30) human insulin, EP 0 214 826 and EP 0 705 275 (Novo Nordisk A/S), e.g. $Asp^{B28}$ human insulin, U.S. Pat. No. 5,504,188 (Eli Lilly), e.g. $Lys^{B28}$ $Pro^{B29}$ human insulin, EP 0 368 187 (Aventis), e.g. Lantus®, which are all incorporated herein by reference, GLP-1 derivatives such as those disclosed in WO 98/08871 (Novo Nordisk A/S), which is incorporated herein by reference, as well as orally active hypoglycaemic agents.

The orally active hypoglycaemic agents preferably comprise imidazolines, sulfonylureas, biguanides, meglitinides, oxadiazolidinediones, thiazolidinediones, insulin sensitizers, α-glucosidase inhibitors, agents acting on the ATP-dependent potassium channel of the β-cells e.g. potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists, such as ALRT-268, LG-1268 or LG-1069.

In one embodiment of the invention the present compounds are administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment of the invention the present compounds are administered in combination with a sulfonylurea e.g. tolbutamide, chlorpropamide, tolazamide, glibenclamide, glipizide, glimepiride, glicazide or glyburide.

In another embodiment of the invention the present compounds are administered in combination with a biguanide e.g. metformin.

In yet another embodiment of the invention the present compounds are administered in combination with a meglitinide e.g. repaglinide or nateglinide.

In still another embodiment of the invention the present compounds are administered in combination with a thiazolidinedione insulin sensitizer e.g. troglitazone, ciglitazone, pioglitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the present compounds may be administered in combination with an insulin sensitizer e.g. such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In a further embodiment of the invention the present compounds are administered in combination with an α-glucosidase inhibitor e.g. voglibose, emiglitate, miglitol or acarbose.

In another embodiment of the invention the present compounds are administered in combination with an agent acting on the ATP-dependent potassium channel of the β-cells e.g. tolbutamide, glibenclamide, glipizide, glicazide, BTS-67582 or repaglinide.

In yet another embodiment of the invention the present compounds may be administered in combination with nateglinide.

In still another embodiment of the invention the present compounds are administered in combination with an antilipidemic agent e.g. cholestyramine, colestipol, clofibrate, gemfibrozil, lovastatin, pravastatin, simvastatin, probucol or dextrothyroxine.

In another aspect of the invention, the present compounds are administered in combination with more than one of the above-mentioned compounds e.g. in combination with metformin and a sulfonylurea such as glyburide; a sulfonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, $19^{th}$ Edition, Gennaro, Ed., Mack Publishing Co., Easton, Pa., 1995.

It should be understood that any suitable combination of the compounds according to the invention with diet and/or exercise, one or more of the above-mentioned compounds and optionally one or more other active substances are considered to be within the scope of the present invention.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, $19^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

For parenteral routes, such as intravenous, intrathecal, intramuscular and similar administration, typically doses are in the order of about half the dose employed for oral administration. The compounds of this invention are generally utilized as the free substance or as a pharmaceutically acceptable salt thereof. One example is an acid addition salt of a compound having the utility of a free base. When a compound of the formula (I) contains a free base such salts are prepared in a conventional manner by treating a solution or suspension of a free base of the formula (I) with a chemical equivalent of a pharmaceutically acceptable acid, for example, inorganic and organic acids. Representative examples are mentioned above. Physiologically acceptable salts of a compound with a hydroxy group include the anion of said compound in combination with a suitable cation such as sodium or ammonium ion.

For parenteral administration, solutions of the novel compounds of the formula (I) in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

A typical tablet, which may be prepared by conventional tabletting techniques, may contain:

Core:

| | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |

Coating:

| | | |
|---|---|---|
| Hydroxypropyl methylcellulose | approx. | 9 mg |
| Mywacett 9-40 T** | approx. | 0.9 mg |

*Polacrillin potassium NF, tablet disintegrant, Rohm and Haas.
**Acylated monoglyceride used as plasticizer for film coating.

If desired, the pharmaceutical composition of the invention may comprise the compound of the formula (I) in combination with further pharmacologically active substances such as those described in the foregoing.

EXAMPLES

NMR spectra were recorded on Bruker 300 MHz and 400 MHz instruments. HPLC-MS was performed on a Perkin Elmer instrument (API 100).

HPLC (Method A)

The reverse phase analysis was performed using UV detections at 214 and 254 nm on a 218TP54 4.6 mm×150 mm C-18 silica column, which was eluted at 1 ml/min at 42° C. The column was equilibrated with 5% acetonitrile, 85% water and 10% of a solution of 0.5% trifluoroacetic acid in water and eluted by a linear gradient from 5% acetonitrile, 85% water and 10% of a solution of 0.5% trifluoroacetic acid to 90% acetonitrile and 10% of a solution of 0.5% trifluoroacetic acid over 15 min.

HPLC (Method B)

The RP-analyses was performed using a Alliance Waters 2695 system fitted with a Waters 2487 dualband detector. UV detections were collected using a Symmetry C18, 3.5 um, 3.0 mm×100 mm column. Eluted with a linear gradient of 5–90% acetonitrile, 90–0% water, and 5% trifluoroacetic acid (1.0%) in water over 8 minutes at a flow-rate of 1.0 min/min.

General Procedure (A)

The compounds of formula (I) according to the invention may be prepared by the general procedure (A):

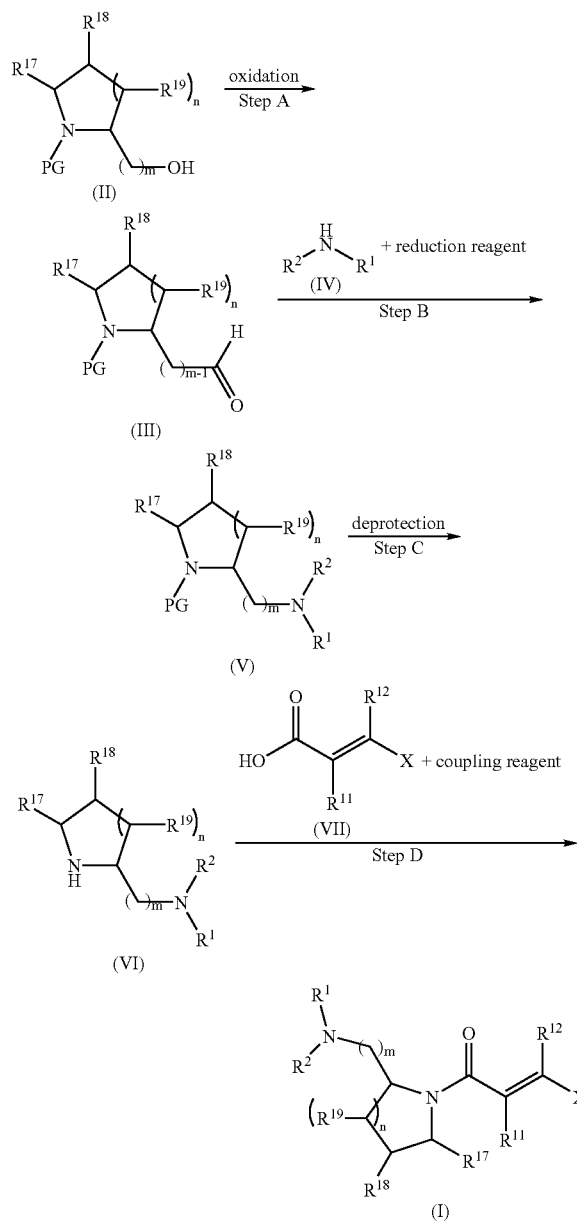

Step A:

The compounds of the general formula (I) are prepared from an N-protected amino alcohol of the general formula (II). The protective group may be chosen from the protective groups known in the art and described in the literature (e.g. T. W. Greene, P. G. Wuts, Protective groups in organic synthesis, $2^{nd}$ edition, John Wiley & Sons Inc., New York, 1991). The amino alcohol of the general formula (II) is oxidized by a suitable method known in the art, e.g. using oxalyl chloride and dimethylsulphoxide or dicyclohexylcarbodiimide and dimethylsulphoxide to yield an aldehyde of the general formula (III).

Step B:

The aldehyde of the general formula (III) is reacted with an amine of the general formula (IV) under acidic or neutral conditions with a reduction reagent such as e.g. sodium acetoxyborohydride or sodium cyanoborohydride to give an amine of the general formula (V).

Step C:

The protective group is removed by a method known in the art and described in the literature (e.g. T. W. Greene, P. G. Wuts, Protective groups in organic synthesis, $2^{nd}$ edition, John Wiley & Sons Inc. New York, 1991) to give an amine of the general formula (VI) either as free base or as a salt.

Step D:

The amine of the general formula (VI)—either as a free base or as a salt—is reacted with an acid of formula (VII) and a coupling reagent such as e.g. a combination of 1-hydroxy-7-azabenzotriazole and 1-(3-dimethylaminopropyl)-3-ethylcarbodiimide hydrochloride salt or a combination of 3-hydroxy-1,2,3-benzotriazin-4(3H)-one and 1-(3-dimethylaminopropyl)-3-ethylcarbodiimide hydrochloride salt, optionally in the presence of an amine base such as e.g. triethylamine or ethyidiisopropylamine, or with an activated derivative of the acid of the formula (VII) such as e.g. an acid chloride, acid imidazolide or a phenolic ester to give a compound of the general formula (I).

General Procedure (B)

The compounds of formula (I) according to the invention may also be prepared by the general procedure (B):

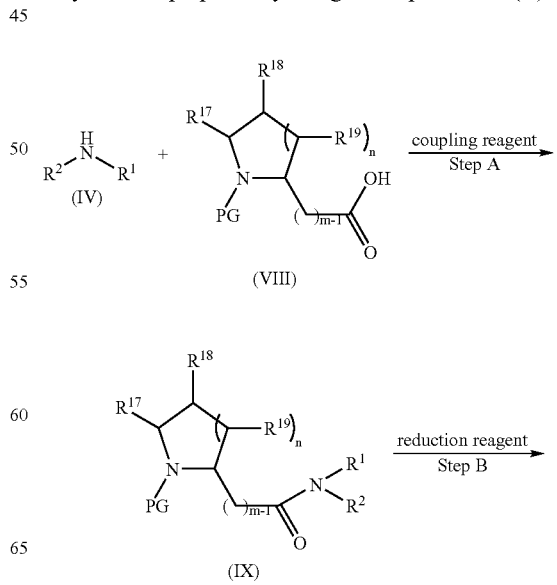

General Procedure (C)

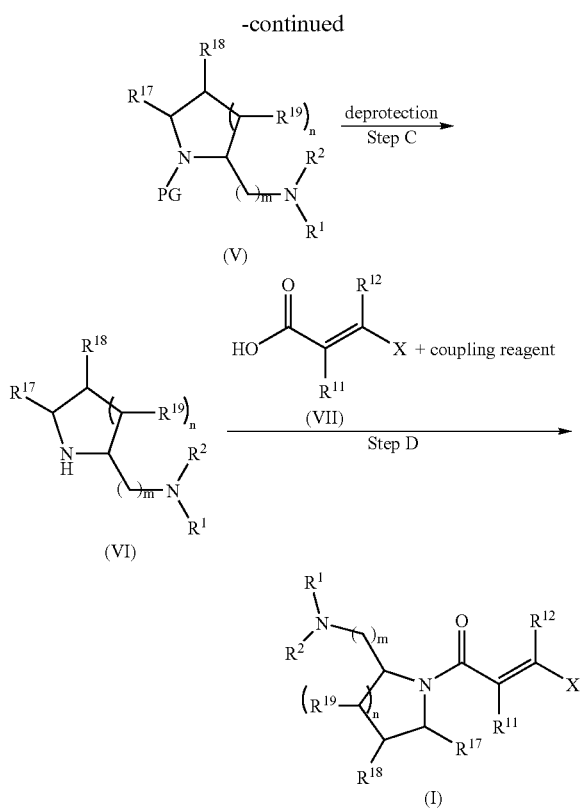

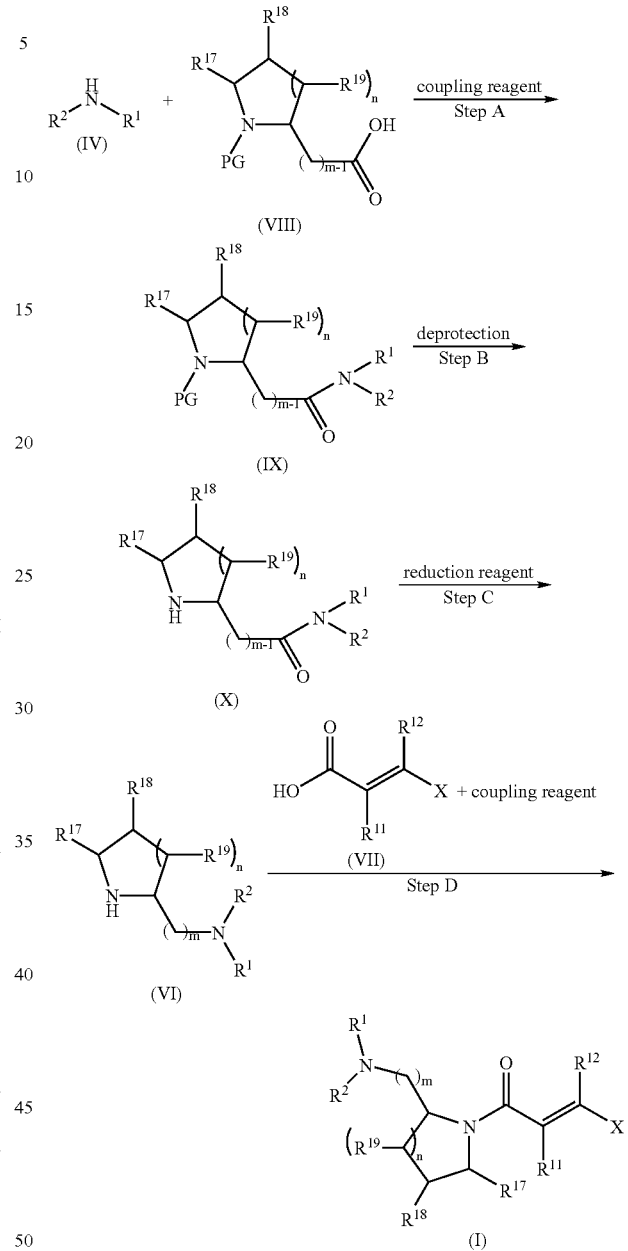

Step A:

The compounds of the general formula (I) are synthesized from a N-protected amino acid of the general formula (VIII). The protective group may be chosen from the protective groups known in the art and described in the literature (e.g. T. W. Greene, P. G. Wuts, Protective groups in organic synthesis, $2^{nd}$ edition, John Wiley & Sons Inc. New York, 1991).

An amine of the general formula (IV)—either as a free base or as a salt—is reacted with a N-protected amino acid of the general formula (VIII) and a coupling reagent such as e.g. a combination of 1-hydroxy-7-azabenzotriazole and 1-(3-dimethylaminopropyl)-3-ethylcarbodiimide hydrochloride salt or a combination of 3-hydroxy-1,2,3-benzotriazin-4(3H)-one and 1-(3-dimethylaminopropyl)-3-ethylcarbodiimide hydrochloride salt, optionally in the presence of an amine base such as e.g. triethylamine or ethyldiisopropylamine, or an activated derivative of the acid of the general formula (VIII) such as e.g. an acid chloride, acid imidazolide or a phenolic ester to give an amide of the general formula (IX).

Step B:

The amide (IX) is reduced with an appropriate reduction reagent such as e.g. borane, a combination of sodium borohydride and iodine or a combination of sodium borohydride and sulfuric acid to give an amine of the general formula (V).

Step C and Step D:

These steps are identical to steps C and D of general procedure (A).

Step A

This step is identical to step A of general procedure (B),

Step B

The protection group of the amine is removed by a method known in the art (e.g. T. W. Greene, P. G. Wuts, Protective groups in organic synthesis, $2^{nd}$ edition, John Wiley & Sons Inc. New York, 1991) to give an amide of the general formula (X) either as free base or as a salt.

Step C:

The amide (X) is reduced with an appropriate reduction reagent such as e.g. lithium aluminum hydride, yielding an amine of the general formula (VI).

Step D:

This step is identical to step D of general procedure (A).

General Procedure (D)

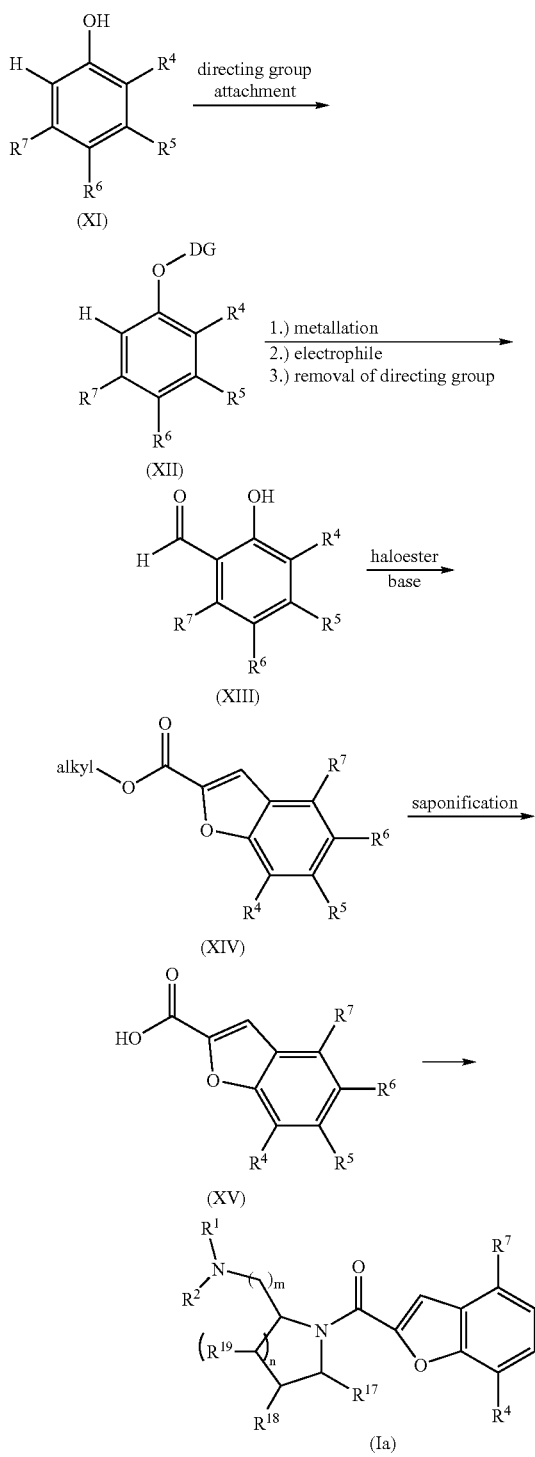

Step A

A metalation directing group DG (e.g. a 2-tetrahydropyranyl group) is attached to a phenol of type (XI) as known for a person trained in the art or described in the literature (e.g. T. W. Greene, P. G. Wuts, Protective groups in organic synthesis, $2^{nd}$ edition, John Wiley & Sons Inc. New York, 1991) to give a compound of type (XII)

Step B

The compound of type (XII) is treated with an alkylmetal reagent such as n-butyllithium sec.-buytllithium or tert.-butyllithium with or without a chelating reagent such as N,N,N',N'-tetramethylethylenediamine at appropriate temperature such as a temperature between −78° C. and room temperature for an appropriate time (5 min-16 h). A suitable electrophile such as N,N-dimethylformamide is added. The directing group is either removed during work up or during a step using a method known for a person trained in the art or described in the literature (e.g. T. W. Greene, P. G. Wuts, Protective groups in organic synthesis, $2^{nd}$ edition, John Wiley & Sons Inc. New York, 1991) to give an aldehyde of type (XIII).

Step C:

The aldehyde of type (XIII) is reacted with a suitable 2-haloester such as e.g. diethyl bromomalonate in the presence of an appropriate base such as potassium carbonate in an appropriate solvent such as ethyl methyl ketone at an appropriate temperature (e.g. between 0° C. and 200° C.) to give the ester of type (XIV).

Step D:

The ester of type (XIV) is saponified with a method known for a person trained in the art or described in the literature (e.g. T. W. Greene, P. G. Wuts, Protective groups in organic synthesis, $2^{nd}$ edition, John Wiley & Sons Inc. New York, 1991), e.g. potassium hydroxide in methanol or lithium hydroxide in a mixture of dioxane and water to give an acid of type (XV).

Step E:

This step is identical to step D of general procedure (A).

General Procedure (E)

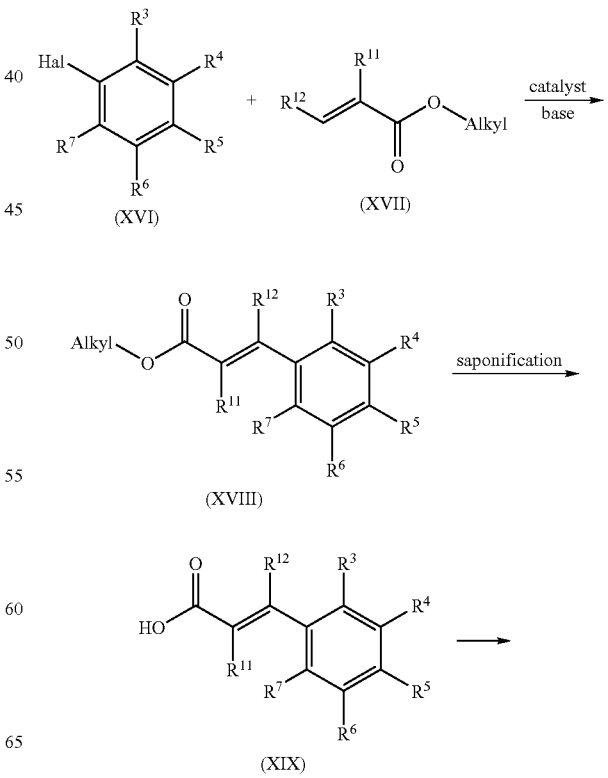

-continued

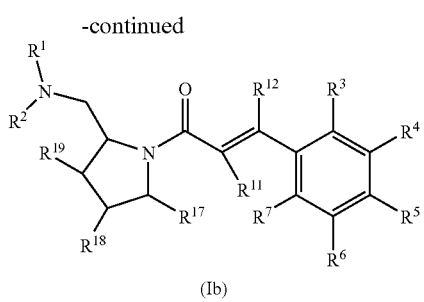

(Ib)

Step A

A suitable halogenarene such as a bromine or iodine compound of the general structure (XVI) is reacted with an alkyl acrylate of the general structure (XVII) in the presence of a suitable catalyst such as e.g. a palladium catalyst such as e.g. palladium(II) acetate in the presence of a suitable ligand such as triphenylphosphine and a suitable base such as e.g. an amine-base such as e.g. triethylamine or ethyidi-isopropylamine, to yield an alkyl acrylate of the general structure (XVIII).

Step B

The ester of type (XVIII) is saponified with a method known for a person trained in the art or described in the literature (e.g. T. W. Greene, P. G. Wuts, Protective groups in organic synthesis, $2^{nd}$ edition, John Wiley & Sons Inc. New York, 1991), e.g. potassium hydroxide in methanol or lithium hydroxide in a mixture of dioxane and water to give an acid of type (XIX).

Step C:

This step is identical to step D of general procedure (A) yielding a compound of the general structure (Ib).

Example 1 (General Procedure (A))

(E)-3-(4-Bromophenyl)-1-((2S)-2-((pyrrolidin-1-yl)methyl)pyrrolidin-1-yl)propenone

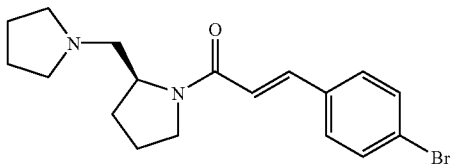

Step A: (S)-2-Formylpyrrolidine-1-carboxylic Acid Tert-Butyl Ester

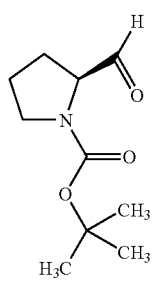

At −78° C., a solution of dimethylsulphoxide (7.06 ml, 0.099 mol) in dichloromethane (10 ml) was added dropwise to a solution of oxalyl chloride (6.40 ml, 0.075 mol) in dichloromethane (15 ml). The reaction mixture was stirred for 20 min at −78° C. A solution of (S)-1-(tert-butoxycarbonyl)-2-pyrrolidinemethanol (10 g, 0.050 mol) in dichloromethane (50 ml) was added. The reaction mixture was stirred for 20 min at −78° C. Triethylamine (27.7 ml, 0.199 mol) was added. The reaction mixture was stirred for 10 min at −78° C. and then warmed to room temperature. It was washed with a 10% aqueous solution of sodium hydrogen sulphate (60 ml). The aqueous phase was extracted with dichloromethane (30 ml). The combined organic layers were washed with a saturated aqueous solution of sodium hydrogen carbonate (100 ml) and dried over magnesium sulphate. The solvent was removed in vacuo, to give 11.2 g of crude (S)-2-formylpyrrolidine-1-carboxylic acid tert-butyl ester, which was used for the next step without purification.

$^1$H NMR (CDCl$_3$, 2 sets of signals) δ 1.50 (m, 9H); 1.75–2.20 (m, 4H); 3.20–4.00 (m, 3H); 4.05 and 4.20 (both t, together 1H); 9.50 and 9.60 (both s, together 1H).

Step B: (S)-2-((Pyrrolidin-1-yl)methyl)pyrrolidine-1-carboxylic Acid Tert-Butyl Ester

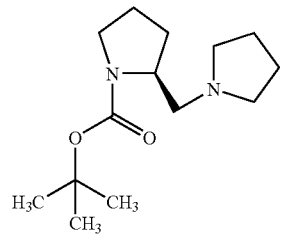

Sodium triacetoxyborohydride (35.7 g, 0.168 mol) was added to a mixture of crude (S)-2-formylpyrrolidine-1-carboxylic acid tert-butyl ester (11.2 g, 0.056 mol), pyrrolidine (5.16 ml, 0.062 mol) and mol sieves (10 g) in dichloromethane (100 ml). Acetic acid (6.42 g, 0.112 mol) was added. The reaction mixture was stirred for 16 hours at room temperature. The precipitation was removed by filtration. The filtrate was diluted with a 1 N aqueous solution of sodium hydroxide (100 ml) and tert-butyl methyl ether (100 ml). The phases were separated. The aqueous phase was extracted with tert-butyl methyl ether (3×80 ml). The combined organic layers were dried over magnesium sulphate. The solvent was removed in vacuo. The crude product was purified by flash chromatography on silica (90 g), using ethyl acetate/heptane/triethylamine (1:1, 5%) as eluent, to give 9.23 g of (S)-2-((pyrrolidin-1-yl)methyl)-pyrrolidine-1-carboxylic acid tert-butyl ester.

$^1$H NMR (CDCl$_3$, 2 sets of signals) δ 1.45 (s, 9H); 1.80–2.10 (m, 8H); 2.50–3.70 (m, 8H); 3.90 and 4.00 (both m, together 1H); HPLC (method A): elution at 10.70 min; MS: Calc. for [M+H]$^+$: 255; Found: 255.

Step C: (S)-2-((Pyrrolidin-1-yl)methyl)pyrrolidine

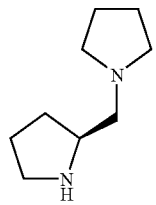

A 3.2 M solution of hydrogen chloride in ethyl acetate (470 ml, 1.5 mol) was added to a solution of (S)-2-((pyrrolidin-1-yl)methyl)pyrrolidine-1-carboxylic acid tert-butyl ester (9.23 g, 0.036 mol) in ethyl acetate (100 ml). The reaction mixture was stirred for 45 min at room temperature. The solvent was removed in vacuo. The residue was dissolved in ethyl acetate (200 ml). The solvent was removed in vacuo, to give 10.30 g of the dihydrochloride salt of (S)-2-((pyrrolidin-1-yl)methyl)pyrrolidine.

$^1$H NMR (DMSO-d$_6$) δ 1.60–2.30 (m, 8H); 3.10 (m, 2H); 3.25 (m, 2H); 3.55 (m, 1H); 3.70 (m, 3H); 3.90 (m, 1H); 9.80 (br, 2H); 11.20 (br, 1H).

Step D:

At 0° C., 1-(3-dimethylaminopropyl)-3-ethylcarbodiimide hydrochloride salt was added to a solution of (E)-4-bromocinnamic acid (0.50 g, 2.20 mmol) and 3-hydroxy-1, 2,3-benzotriazin-4(3H)-one (0.36 g, 2.20 mmol) in a mixture of dichloromethane (6 ml) and N,N-dimethylformamide (6 ml). The reaction mixture was stirred for 20 min at 0° C. A solution of the dihydrochloride salt of (S)-2-((pyrrolidin-1-yl)methyl)pyrrolidine (0.50 g, 2.20 mmol) in N,N-dimethylformamide (8 ml) was added. The reaction mixture was stirred for 16 hours, while it was warming up to room temperature. It was diluted with ethyl acetate (100 ml), washed with brine (100 ml), and dried over magnesium sulphate. The solvent was removed in vacuo. The crude product was purified by flash chromatography on silica (40 g), using dichloromethane/methanol/25% aqueous ammonia as eluent, to give 340 mg of the title compound.

$^1$H NMR (CDCl$_3$, 2 sets of signals) δ 1.70–2.20 (m, 8H); 2.45–2.80 (m, 6H); 3.60 and 3.70 (both m, together 2H); 4.20 and 4.40 (both m, together 1H); 7.70 and 7.90 (both d, together 1H); 7.40 (m, 2H); 7.50 (m, 2H); 7.65 (d, 1H); HPLC (method A): elution at 9.19 min; MS: Calc. for [M+H]$^+$: 363; Found: 363.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

C$_{18}$H$_{23}$BrN$_2$O.HCl.3 H$_2$O (363.30•36.46•3 18.02) Calcd.: C, 47.64; H, 6.66; N, 6.17; Found: C, 47.41; H, 6.68; N, 7.39.

Example 2 (General Procedure (A))

(E)-3-(5-Bromo-2-ethoxyphenyl)-1-((S)-2-((pyrrolidin-1-yl)methyl)pyrrolidin-1-yl)propenone

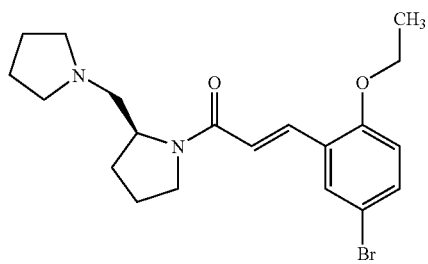

300 mg of the title compound were synthesized as described for (E)-3-(4-bromophenyl)-1-((2S)-2-((pyrrolidin-1-yl)methyl)pyrrolidin-1-yl)propenone, using (E)-5-bromo-2-ethoxycinnamic acid instead of (E)-4-bromocinnamic acid.

$^1$H NMR (CDCl$_3$, 2 sets of signals) δ 1.45 (t, 3H); 1.80–2.20 (m, 8H); 2.45–2.80 (m, 6H); 1.60 and 1.70 (both m, together 2H); 4.05 (q, 2H); 4.15 and 4.40 (both m, together 1H); 6.75 (d, 1H); 6.85 and 6.95 (both d, together 1H); 7.35 (d, 1H); 7.60 (dd, 1H); 7.85 and 7.95 (both d, together 1H); HPLC (method A): elution at 9.89 min; MS: Calc. for [M+H]$^+$: 407; Found: 407.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

C$_{20}$H$_{27}$BrN$_2$O$_2$.HCl.H$_2$O (407.35•36.46•18.02) Calcd.: C, 52.02; H, 6.55; N, 6.07; Found: C, 51.55; H, 6.42; N, 6.60.

Example 3 (General Procedure (A))

(E)-3-(4-Chlorophenyl)-1-((S)-2-((pyrrolidin-1-yl)methyl)pyrrolidin-1-yl)propenone

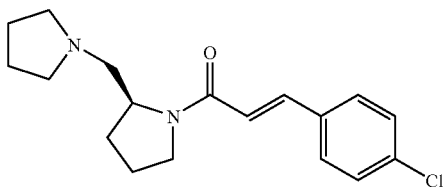

310 mg of the title compound were synthesized as described for (E)-3-(4-bromophenyl)-1-((2S)-2-((pyrrolidin-1-yl)methyl)pyrrolidin-1-yl)propenone, using (E)-4-chlorocinnamic acid instead of (E)-4-bromocinnamic acid.

HPLC (method A): elution at 9.04 min; MS: Calc. for [M+H]$^+$: 319; Found: 319.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

$^1$H NMR (DMSO-d$_6$, 2 sets of signals) δ 1.80–2.15 (m, 8H); 3.10, 3.20, 3.30, 3.45, and 3.55–3.85 (m, together 8H); 4.40 and 4.75 (both m, together 1H); 7.05 and 7.15 (both d, together 1H); 7.50 (m, 3H); 7.80 and 7.90 (both d, together 2H); 10.2 (br, 1H).

Example 4 (General Procedure (A))

(E)-1-((S)-2-((Pyrrolidin-1-yl)methyl)pyrrolidin-1-yl)-3-(4-(trifluoromethyl)phenyl)propenone

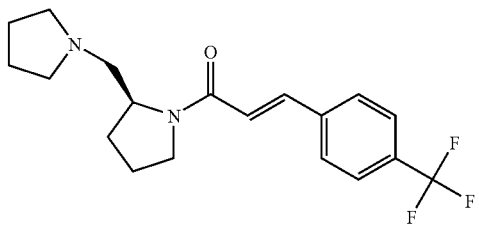

160 mg of the title compound were synthesized as described for (E)-3-(4-bromophenyl)-1-((2S)-2-((pyrrolidin-1-yl)methyl)pyrrolidin-1-yl)propenone, using (E)-4-(trifluoromethyl)cinnamic acid instead of (E)-4-bromocinnamic acid.

HPLC (method A): elution at 9.58 min; MS: Calc. for [M+H]$^+$: 353; Found: 353.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

$^1$H NMR (DMSO-d$_6$, 2 sets of signals) δ 1.80–2.15 (m, 8H); 3.10, 3.25, 3.30, 3.45, and 3.55–3.80 (all m, together 8H); 4.40 and 4.80 (both m, together 1H); 7.20 and 7.30 (both d, together 1H); 7.70 and 7.75 (both d, together 1H); 7.75 and 7.80 (both d, together 2H); 7.95 and 8.10 (both d, together 2H); 10.25 (br, 1H).

Example 5 (General Procedure (A))

(E)-3-(3-Bromophenyl)-1-((S)-2-((pyrrolidin-1-yl)methyl)pyrrolidin-1-yl)propenone

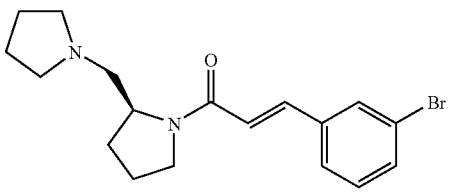

290 mg of the title compound were synthesized as described for (E)-3-(4-bromophenyl)-1-((2S)-2-((pyrrolidin-1-yl)methyl)pyrrolidin-1-yl)propenone, using (E)-3-bromocinnamic acid instead of (E)-4-bromocinnamic acid.

$^1$H NMR (CDCl$_3$, 2 sets of signals) δ 1.70–1.85 (m, 4H); 1.90–2.20 (m, 5H); 2.40–2.75 (m, 6 H); 3.60 (t, 1H); 4.15 and 4.40 (both m, together 1H); 6.70 and 6.95 (both d, together 1H); 7.45 (m, 2H); 7.60 (d, 1H); 7.80 (t, 1H); HPLC (method A): elution at 9.10 min; MS: Calc. for [M+H]$^+$: 363; Found: 363.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 6 (General Procedure (A))

(E)-3-(2-Bromophenyl)-1-((S)-2-((pyrrolidin-1-yl)methyl)pyrrolidin-1-yl)propenone

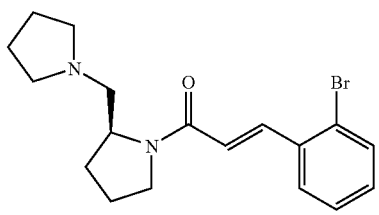

250 mg of the title compound were synthesized as described for (E)-3-(4-bromophenyl)-1-((2S)-2-((pyrroli-din-1-yl)methyl)pyrrolidin-1-yl)propenone, using (E)-2-bromocinnamic acid instead of (E)-4-bromocinnamic acid.

$^1$H NMR (CDCl$_3$, 2 sets of signals) δ 1.50–1.90 (m, 4H); 1.90–2.20 (m, 4H); 2.50–2.85 (m ,6 H); 3.55–3.80 (m, 2H); 4.15 and 4.40 (both m, together 1H); 6.65 and 6.85 (both d, together 1H); 7.10–7.40 (m, 2H); 7.50–7.70 (m, 2H); 8.05 (d, 1H); HPLC (method A): elution at 8.89 min; MS: Calc. for [M+H]$^+$: 363; Found: 363.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 7 (General Procedure (A))

(E)-3-(4-Methoxyphenyl)-1-((S)-2-((pyrrolidin-1-yl)methyl)pyrrolidin-1-yl)propenone

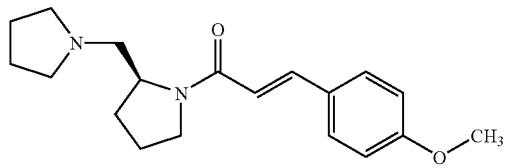

340 mg of the title compound were synthesized as described for (E)-3-(4-bromophenyl)-1-((2S)-2-((pyrrolidin-1-yl)methyl)pyrrolidin-1-yl)propenone, using (E)-4-methoxycinnamic acid instead of (E)-4-bromocinnamic acid.

$^1$H NMR (CDCl$_3$; 2 sets of signals) δ 1.80 (m, 4H); 1.90–2.10 (m, 3H); 2.20 (m, 2H); 2.45–2.80 (m, 5H); 3.60 and 3.70 (both m, together 2H); 3.85 (s, 3H); 4.15 and 4.40 (both m, together 1H); 6.60 and 6.75 (both d, together 1H); 6.90 (m, 2H); 7.48 (d, 2H); 7.64 and 7.65 (both d, together 1H); HPLC (method A): elution at 7.91 min; MS: Calc. for [M+H]$^+$: 315; Found: 315.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 8 (General Procedure (A))

(E)-3-(3-Methoxyphenyl)-1-((S)-2-((pyrrolidin-1-yl)methyl)pyrrolidin-1-yl)propenone

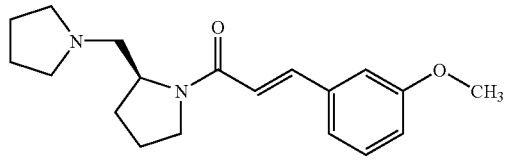

420 mg of the title compound were synthesized as described for (E)-3-(4-bromophenyl)-1-((2S)-2-((pyrrolidin-1-yl)methyl)pyrrolidin-1-yl)propenone, using (E)-3-methoxycinnamic acid instead of (E)-4-bromocinnamic acid.

¹H NMR (CDCl₃; 2 sets of signals) δ 1.80 (m, 4H); 1.90–2.20 (m, 5H); 2.45–2.80 (m, 5H); 3.60 and 3.70 (both m, together 2H); 3.85 (s, 3H); 4.15 and 4.40 (both m, together 1H); 6.70 and 6.85 (both d, together 1H); 6.90 (dd, 1H); 7.05 (s, 1H); 7.15 (d, 1H); 7.30 (m, 1 H); 7.70 (d, 1H); HPLC (method A): elution at 7.99 min; MS: Calc. for [M+H]⁺: 315; Found: 315.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 9 (General Procedure (A))

(E)-3-(4-Bromophenyl)-1-((R)-2-((pyrrolidin-1-yl)methyl)pyrrolidin-1-yl)propenone

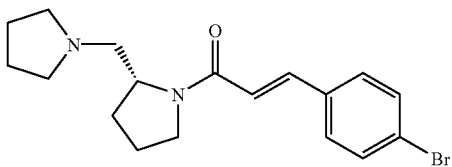

520 mg of the title compound were synthesized as described for (E)-3-(4-bromophenyl)-1-((2S)-2-((pyrrolidin-1-yl)methyl)pyrrolidin-1-yl)propenone, using (R)-1-(tert-butoxycarbonyl)-2-pyrrolidinemethanol instead of (S)-1-(tert-butoxycarbonyl)-2-pyrrolidinemethanol.

¹H NMR (CDCl₃, 2 sets of signals) δ 1.70–2.20 (m, 8H); 2.45–2.80 (m, 6H); 3.60 and 3.70 (both m, together 2H); 4.15 and 4.40 (both m, together 1H); 7.70 and 7.90 (both d, together 1H); 7.40 (m, 2H); 7.50 (m, 2H); 7.65 (d, 1H); HPLC (method A): elution at 9.05 min; MS: Calc. for [M+H]⁺: 363; Found: 363.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 10 (General Procedure (A))

(E)-1-((R)-2-((Pyrrolidin-1-yl)methyl)pyrrolidin-1-yl)-3-(4-trifluoromethylphenyl)propenone

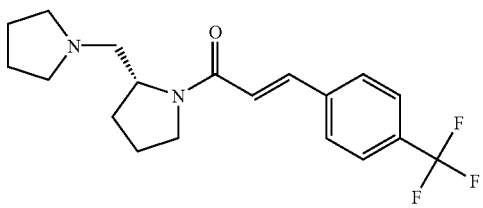

352 mg of the title compound were synthesized as described for (E)-3-(4-bromophenyl)-1-((2S)-2-((pyrrolidin-1-yl)methyl)pyrrolidin-1-yl)propenone, using (R)-1-(tert-butoxycarbonyl)-2-pyrrolidinemethanol instead of (S)-1-(tert-butoxycarbonyl)-2-pyrrolidinemethanol and (E)-4-trifluoromethylcinnamic acid instead of (E)-4-bromocinnamic acid.

¹H NMR (CDCl₃, 2 sets of signals) δ 1.80 (m, 4H); 1.90–2.20 (m, 4H); 2.45–1.85 (m, 6H); 3.60 and 3.70 (both m, together 2H); 4.15 and 4.40 (both m, together 1H); 6.80 and 7.00 (both d, together 1H); 7.65 (AB, 4H); 7.70 (d, 1H); HPLC (method A): elution at 9.33 min; MS: Calc. for [M+H]⁺: 353; Found: 353.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 11 (General Procedure (A))

(E)-3-(3-Chlorophenyl)-1-((S)-2-((pyrrolidin-1-yl)methyl)pyrrolidin-1-yl)propenone

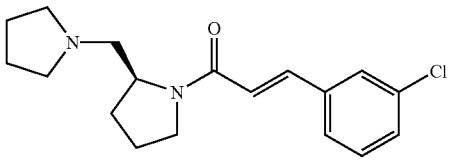

340 mg of the title compound were synthesized as described for (E)-3-(4-bromophenyl)-1-((2S)-2-((pyrrolidin-1-yl)methyl)pyrrolidin-1-yl)propenone, using (E)-3-chlorocinnamic acid instead of (E)-4-bromocinnamic acid.

¹H-NMR (CDCl₃, 2 sets of signals) δ 1.75 (m, 4H); 1.85–2.15 (m, 4H); 2.40–2.75 (m, 6H); 3.50–3.75 (m, 2H); 4.15 and 4.40 (both m, together 1H); 6.75 and 6.90 (both d, together 1H); 7.20–7.40 (m, 3H); 7.50 (s, 1H); 7.65 (d, 1H). HPLC method A: elution at 8.82 min. MS: calc. for [M+H]⁺: 319; found: 319.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 12 (General Procedure (A))

(E)-3-(3-Fluorophenyl)-1-((S)-2-((pyrrolidin-1-yl)methyl)pyrrolidin-1-yl)propenone

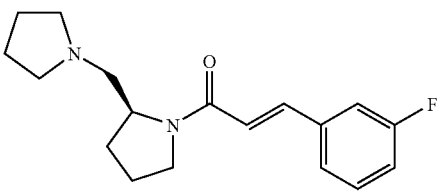

210 mg of the title compound were synthesized as described for (E)-3-(4-bromophenyl)-1-((2S)-2-((pyrrolidin-1-yl)methyl)pyrrolidin-1-yl)propenone, using (E)-3-fluorocinnamic acid instead of (E)-4-bromocinnamic acid.

¹H-NMR (CDCl₃, 2 sets of signals) δ 1.75 (m, 4H); 1.90–2.10 (m, 4H); 2.45–2.75 (m, 7H); 3.60 and 3.67 (t and d, together 2H); 4.15 and 4.40 (both m, together 1H); 6.70 and 6.90 (both d, together 1H); 7.05 (dt, 1H); 7.20 (d, 1H);

7.25–7.40 (m, 2H); 7.65 (d, 1H). HPLC method A: elution at 8.07 min. MS: calc. for [M+H]+: 303; found: 303.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 13 (General Procedure (A))

(E)-3-(4-Fluorophenyl)-1-((S)-2-((pyrrolidin-1-yl)methyl)pyrrolidin-1-yl)propenone

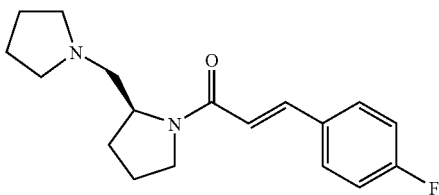

280 mg of the title compound were synthesized as described for (E)-3-(4-bromophenyl)-1-((2S)-2-((pyrrolidin-1-yl)methyl)pyrrolidin-1-yl)propenone, using (E)-4-fluorocinnamic acid instead of (E)-4-bromocinnamic acid.

$^1$H-NMR (CDCl$_3$, 2 sets of signals) δ 1.80 (m, 4H); 1.85–2.20 (m, 4H); 2.40–2.75 (m, 6H); 3.55–3.75 (m, 2H); 4.15 and 4.40 (both m, together 1H); 6.65 and 6.80 (both d, together 1 H); 7.05 (m, 2H); 7.50 (m, 2H); 7.65 (d, 1H). HPLC method A: elution at 8.05 min. MS: calc. for [M+H]+: 303; found: 303.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 14 (General Procedure (A))

(E)-3-(Benzo[1,3]dioxol-5-yl)-1-((S)-2-((pyrrolidin-1-yl)methyl)pyrrolidin-1-yl)propenone

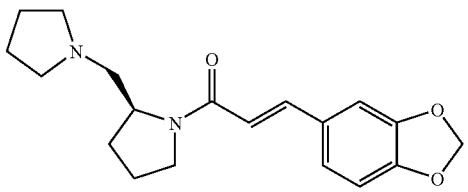

340 mg of the title compound were synthesized as described for (E)-3-(4-bromophenyl)-1-((2S)-2-((pyrrolidin-1-yl)methyl)pyrrolidin-1-yl)propenone, using (E)-3-(benzo[1,3]dioxol-5-yl)acrylic acid instead of (E)-4-bromocinnamic acid.

$^1$H-NMR (CDCl$_3$, 2 sets of signals) δ 1.80 (m, 4H); 1.90–2.30 (m, 4H); 2.45–2.80 (m, 6H); 3.55–3.75 (m, 2H); 4.15–4.40 (both m, together 1H); 6.00 (s, 2H); 6.55 and 6.70 (both d, together 1H); 6.80 (dd, 1H); 7.00 (d, 1H); 7.02 (s, 1H); 7.60 (d, 1H). HPLC method A: elution at 7.86 min. MS: calc. for [M+H]+: 329; found: 329.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 15 (General Procedure (A))

(E)-3-(3,4-Dimethoxyphenyl)-1-((S)-2-((pyrrolidin-1-yl)methyl)pyrrolidin-1-yl)propenone

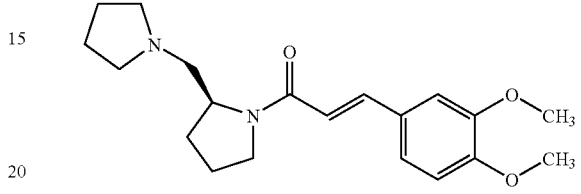

240 mg of the title compound were synthesized as described for (E)-3-(4-bromophenyl)-1-((2S)-2-((pyrrolidin-1-yl)methyl)pyrrolidin-1-yl)propenone, using (E)-3,4-dimethoxycinnamic acid instead of (E)-4-bromocinnamic acid.

$^1$H-NMR (CDCl$_3$, 2 sets of signals) δ 1.75 (m, 4H); 1.85–2.20 (m, 4H); 2.45–2.75 (m, 6H); 3.55–3.75 (m, 2H); 3.90 (s, 6H); 4.15 and 4.40 (both m, together 1H); 6.55 and 6.70 (both d, together 1H); 6.85 (dd, 1H); 7.05 (d, 1H); 7.10 (dd, 1H); 7.55 (d, 1H). HPLC method A: elution at 7.60. MS: calc. for [M+H]+: 345; found: 345.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 16 (General Procedure (A))

(E)-3-(2,4-Dimethoxyphenyl)-1-((S)-2-((pyrrolidin-1-yl)methyl)pyrrolidin-1-yl)propenone

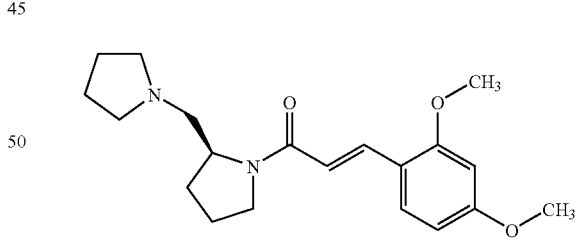

320 mg of the title compound were synthesized as described for (E)-3-(4-bromophenyl)-1-((2S)-2-((pyrrolidin-1-yl)methyl)pyrrolidin-1-yl)propenone, using (E)-2,4-dimethoxycinnamic acid instead of (E)-4-bromocinnamic acid.

$^1$H-NMR (CDCl$_3$, 2 sets of signals) δ 1.75 (m, 4H); 1.85–2.20 (m, 4H); 2.45–2.75 (m, 6H); 3.50–3.75 (m, 2H); 3.82 (s, 3H); 3.85 (s, 3H); 4.15 and 4.40 (both m, together 1H); 6.45 (m, 2H); 6.75 and 6.90 (both d, together 1H); 7.45 (dd, 1H); 7.85 and 7.90 (both d, together 1H). HPLC method A: elution at 8.47 min. MS: calc. for [M+H]+: 345; found: 345.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 17 (General Procedure (A))

(E)-3-(4-Bromo-2-fluorophenyl)-1-((S)-2-((pyrrolidin-1-yl)methyl)pyrrolidin-1-yl)propenone

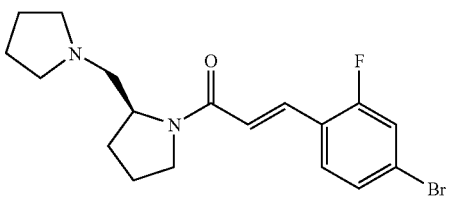

390 mg of the title compound were synthesized as described for (E)-3-(4-bromophenyl)-1-((2S)-2-((pyrrolidin-1-yl)methyl)pyrrolidin-1-yl)propenone, using (E)-4-bormo-2-fluorocinnamic acid instead of (E)-4-bromocinnamic acid.

$^1$H-NMR (CDCl$_3$, 2 sets of signals) δ 1.75 (m, 4H); 1.85–2.20 (m, 4H); 2.35–2.75 (m, 6H); 3.50–3.75 (m, 2H); 4.15 and 4.40 (both m, together 1H); 6.85 and 7.05 (both d, together 1 H); 7.25–7.45 (m, 3H); 7.65 and 7.70 (both d, together 1H). HPLC method A: elution at 9.27 min. MS: calc. for [M+H]$^+$: 381; found: 381.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 18 (General Procedure (A))

(E)-1-((S)-2-((Pyrrolidin-1-yl)methyl)pyrrolidin-1-yl)-3-(4-(trifluoromethoxy)phenyl)propenone

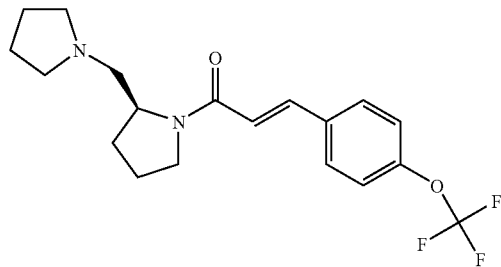

98 mg of the title compound were synthesized as described for (E)-3-(4-bromophenyl)-1-((2S)-2-((pyrrolidin-1-yl)methyl)pyrrolidin-1-yl)propenone, using (E)-4-trifluoromethoxycinnamic acid instead of (E)-4-bromocinnamic acid.

$^1$H-NMR (CDCl$_3$, 2 sets of signals) δ 1.80 (m, 4H); 1.85–2.20 (m, 4H); 2.40–2.80 (m, 6H); 3.55–3.75 (m, 2H); 4.15 and 4.40 (both m, together 1H); 6.70 and 6.85 (both d, together 1H); 7.20 (d, 2H); 7.55 (d, 2H); 7.65 (d, 1H). HPLC method A: elution at 9.75 min. MS: calc. for [M+H]$^+$: 369; found: 369.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 19 (General Procedure (A))

(E)-3-(4-(Dimethylamino)phenyl)-1-((S)-2-((pyrrolidin-1-yl)methyl)pyrrolidin-1-yl)propenone

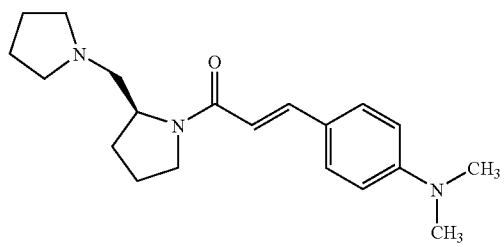

74 mg of the title compound were synthesized as described for (E)-3-(4-bromophenyl)-1-((S)-2-((pyrrolidin-1-yl)methyl)pyrrolidin-1-yl)propenone, using (E)-4-(dimethylamino)cinnamic acid instead of (E)-4-bromocinnamic acid.

$^1$H-NMR (CDCl$_3$, 2 sets of signals) δ 1.50–2.15 (m, 8H); 2.45–2.80 (m, 6H); 3.00 (s, 6H); 3.60 and 3.65 (both m, together 2H); 4.15 and 4.45 (both m, together 1H); 6.50 and 6.65 (both d, together 1H); 6.67 (m, 2H); 7.40 (d, 2H); 7.65 (d, 1H). HPLC method A: elution at 7.23 min. MS: calc. for [M+H]$^+$: 328; found: 328.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 20 (General Procedure (A))

(E)-3-(4-Bromophenyl)-1-((S)-2-((piperidin-1-yl)methyl)pyrrolidin-1-yl)propenone

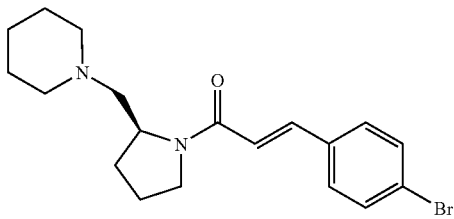

Step 1:

1-(((S)-Pyrrolidin-2-yl)methyl)piperidine

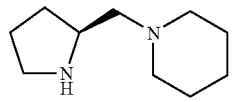

8.3 g of 1-(((S)-pyrrolidin-2-yl)methyl)piperidine were synthesized as desribed for (S)-2-((pyrrolidin-1-yl)methyl)pyrrolidne, using piperidine instead of pyrrolidine.

1H-NMR (CDCl$_3$, free base) δ 1.30 (m, 1H); 1.40 (m, 2H); 1.55 (m, 4H); 1.75 (m, 2H); 1.90 (m, 1H); 2.30 (m, 2H); 2.35 (m, 2H); 2.50 (m, 2H); 2.65 (br, 1H); 2.90 (m, 1H); 3.00 (m, 1H); 3.25 (m, 1H).

Step 2:

520 mg of the title compound were synthesized as described for (E)-3-(4-bromophenyl)-1-((S)-2-((pyrrolidin-1-yl)methyl)pyrrolidin-1-yl)propenone, using 1-(((S)-pyrrolidin-2-yl)methyl)piperidine instead of (S)-2-((pyrrolidin-1-yl)methyl)pyrrolidne.

1H-NMR (CDCl$_3$, 2 sets of signals) δ 1.45 (m, 2H); 1.55 (m, 4H); 2.85–2.10 (m, 4H); 2.15–2.70 (m, 6H); 3.55–3.75 (m, 2H); 4.15 and 4.40 (both m, together 1H); 6.70 and 6.95 (both d, together 1H); 7.40 (d, 2H); 7.50 (d, 2H); 7.60 (d, 1H). HPLC method A: elution at 9.48 min. MS: calc. for [M+H]$^+$: calcd. 377; found: 377.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 21 (General Procedure (A))

(E)-3-(4-Chlorophenyl)-1-((S)-((2-piperidin-1-yl)methyl)pyrrolidin-1-yl)propenone

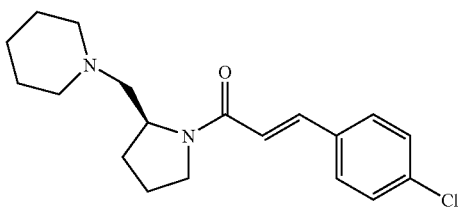

220 mg of the title compound were synthesized as described for (E)-3-(4-bromophenyl)-1-((S)-2-((pyrrolidin-1-yl)methyl)pyrrolidin-1-yl)propenone, using 1-(((S)-pyrrolidin-2-yl)methyl)piperidine instead of (S)-2-((pyrrolidin-1-yl)methyl)pyrrolidine and (E)-4-chlorocinnamic acid instead of (E)-4-bromocinnamic acid.

¹H-NMR (CDCl$_3$, 2 sets of signals) δ 1.45 (m, 2H); 1.55 (m, 4H); 1.80–2.10 (m, 4H); 2.15–2.70 (m, 6H); 3.50–3.75 (m, 2H); 4.15 and 4.40 (both m, together 1H); 6.70 and 6.90 (both d, together 1H); 7.35 (d, 2H); 7.45 (d, 2H); 7.65 (d, 1H). HPLC method A: elution at 9.37 min. MS: calc. for [M+H]$^+$: 333; found: 333.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 22 (General Procedure (A))

(E)-1-((S)-2-((Piperidin-1-yl)methyl)pyrrolidin-1-yl)-3-(4-(trifluoromethyl)phenyl)propenone

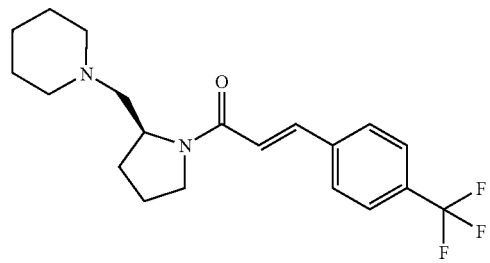

130 mg of the title compound were synthesized as described for (E)-3-(4-bromophenyl)-1-((S)-2-((pyrrolidin-1-yl)methyl)pyrrolidin-1-yl)propenone, using 1-(((S)-pyrrolidin-2-yl)methyl)piperidine instead of (S)-2-((pyrrolidin-1-yl)methyl)pyrrolidine and (E)-4-(trifluoromethyl)cinnamic acid instead of (E)-4-bromocinnamic acid.

¹H-NMR (CDCl$_3$, 2 sets of signals) δ 1.40 (m, 2H); 1.55 (m, 4H); 1.80–2.10 (m, 4H); 2.15–2.70 (m, 6H); 3.55–3.75 (m, 2H); 4.15 and 4.40 (both m, together 1H); 6.80 and 7.05 (both d, together 1H); 7.60 (m, 4H); 7.70 (d, 1H). HPLC method A: elution at 9.87 min. MS: calc. for [M+H]$^+$: 367; found: 367.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 23 (General Procedure (A))

(E)-3-(3-Bromophenyl)-1-((S)-2-((piperidin-1-yl)methyl)pyrrolidin-1-yl)propenone

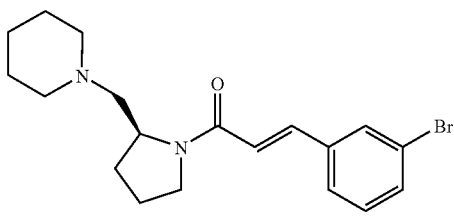

140 mg of the title compound were synthesized as described for (E)-3-(4-bromophenyl)-1-((S)-2-((pyrrolidin-1-yl)methyl)pyrrolidin-1-yl)propenone, using 1-(((S)-pyrrolidin-2-yl)methyl)piperidine instead of (S)-2-((pyrrolidin-1-yl)methyl)pyrrolidine and (E)-3-bromocinnamic acid instead of (E)-4-bromocinnamic acid.

¹H-NMR (CDCl$_3$, 2 sets of signals) δ 1.45 (m, 2H); 1.60 (m, 4H); 1.80–2.10 (m, 4H); 2.15–2.70 (m, 6H); 3.50–3.75 (m, 2H); 4.15 and 4.40 (both m, together 1H); 6.70 and 6.95 (both d, together 1H); 7.25 (m, 1H); 7.45 (m, 1H); 7.60 and 7.61 (both d, together 1H); 7.70 (m, 1H). HPLC method A: elution at 9.60 min. MS: calc. for [M+H]$^+$: 377; found: 377.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 24 (General Procedure (A))

(E)-3-(4-Methoxyphenyl)-1-((S)-2-((piperidin-1-yl)methyl)pyrrolidin-1-yl)propenone

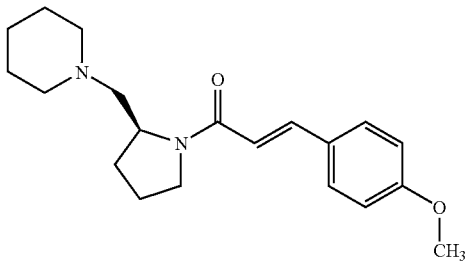

160 mg of the title compound were synthesized as described for (E)-3-(4-bromophenyl)-1-((S)-2-((pyrrolidin-1-yl)methyl)pyrrolidin-1-yl)propenone, using 1-(((S)-pyrrolidin-2-yl)methyl)piperidine instead of (S)-2-((pyrrolidin-1-yl)methyl)pyrrolidine and (E)-4-methoxycinnamic acid instead of (E)-4-bromocinnamic acid.

$^1$H-NMR (CDCl$_3$, 2 sets of signals) δ 1.45 (m, 2H); 1.55 (m, 4H); 1.85–2.10 (m, 4H); 2.15–2.70 (m, 6H); 3.55–3.75 (m, 2H); 3.85 (s, 3H); 4.15 and 4.40 (both m, together 1H); 6.60 and 6.75 (both d, together 1H); 6.90 (m, 2H); 7.50 (d, 2H); 7.65 (d, 1H). HPLC method A: elution at 8.61 min. MS: calc. for [M+H]$^+$: 329; found: 329.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 25 (General Procedure (A))

(E)-3-(3,4-Dimethoxyphenyl)-1-((S)-2-((piperidin-1-yl)methyl)pyrrolidin-1-yl)propenone

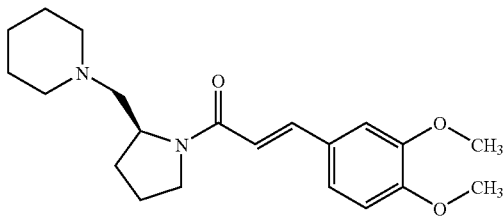

190 mg of the title compound were synthesized as described for (E)-3-(4-bromophenyl)-1-((S)-2-((pyrrolidin-1-yl)methyl)pyrrolidin-1-yl)propenone, using 1-(((S)-pyrrolidin-2-yl)methyl)piperidine instead of (S)-2-((pyrrolidin-1-yl)methyl)pyrrolidine and (E)-3,4-dimethoxycinnamic acid instead of (E)-4-bromocinnamic acid.

$^1$H-NMR (CDCl$_3$, 2 sets of signals) δ 1.40 (m, 2H); 1.55 (m, 4H); 1.80–2.10 (m, 4H); 2.15–2.70 (m, 6H); 3.50–3.75 (m, 2H); 3.90 (s, 6H); 4.15 and 4.40 (both m, together 1H); 6.65 and 6.75 (both d, together 1H); 6.85 (m,1H); 7.10 (AB, 2H); 7.65 (d, 1H). HPLC method A: elution at 8.00 min. MS: calc. for [M+H]$^+$: 359; found. 359.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 26 (General Procedure (A))

(E)-3-(4-Chloro-3-nitrophenyl)-1-((S)-2-((piperidin-1-yl)methyl)pyrrolidin-1-yl)propenone

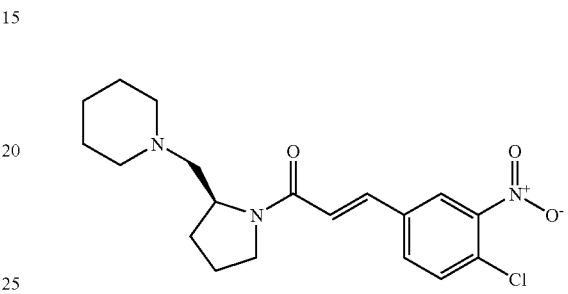

200 mg of the title compound were synthesized as described for (E)-3-(4-bromophenyl)-1-((S)-2-((pyrrolidin-1-yl)methyl)pyrrolidin-1-yl)propenone, using 1-(((S)-pyrrolidin-2-yl)methyl)piperidine instead of (S)-2-((pyrrolidin-1-yl)methyl)pyrrolidine and (E)-4-chloro-3-nitrocinnamic acid instead of (E)-4-bromocinnamic acid.

$^1$H-NMR (CDCl$_3$, 2 sets of signals) δ 1.45 (m, 2H); 1.55 (m, 4H); 1.85–2.10 (m, 4H); 2.15–2.70 (m, 6H); 3.55–3.75 (m, 2H); 4.15 and 4.40 (both m, together 1H); 6.75 and 7.05 (both d, together 1H); 7.50–7.70 (m, 2H); 8.00 and 8.05 (both s, together 1H). HPLC method A: elution at 9.19 min. MS: calc. for [M+H]$^+$: 377; found: 377.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 27 (General Procedure (A))

(E)-1-((S)-2-((Piperidin-1-yl)methyl)pyrrolidin-1-yl)-3-(4-(trifluoromethoxy)phenyl)propenone

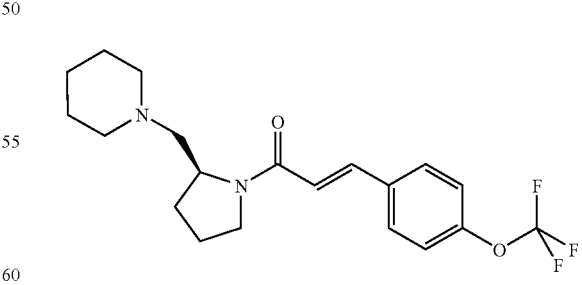

370 mg of the title compound were synthesized as described for (E)-3-(4-bromophenyl)-1-((S)-2-((pyrrolidin-1-yl)methyl)pyrrolidin-1-yl)propenone, using 1-(((S)-pyrrolidin-2-yl)methyl)piperidine instead of (S)-2-((pyrrolidin-1-yl)methyl)pyrrolidine and (E)-4-(trifluoromethoxy)cinnamic acid instead of (E)-4-bromocinnamic acid.

¹H-NMR (CDCl₃, 2 sets of signals) δ 1.45 (m, 2H); 1.55 (m, 4H); 1.85–2.10 (m, 4H); 2.15–2.70 (m, 6H); 3.50–3.75 (m, 2H); 4.15 and 4.40 (both m, together 1H); 6.70 and 6.90 (both d, together 1H); 7.20 (d, 2H); 7.55 (d, 2H); 7.65 (d, 1H). HPLC method A: elution at 10.11 min. MS: calc. for [M+H]⁺: 383; found: 383.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 28 (General Procedure (A))

(E)-3-(Biphenyl-4-yl)-1-((S)-2-((pyrrolidin-1-yl)methyl)pyrrolidin-1-yl)propenone

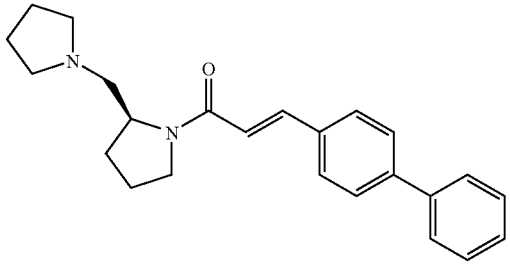

180 mg of the title compound were synthesized as described for (E)-3-(4-bromophenyl)-1-((S)-2-((pyrrolidin-1-yl)methyl)pyrrolidin-1-yl)propenone, using (E)-3-(biphenyl-4-yl)acrylic acid instead of (E)-4-bromocinnamic acid.

¹H-NMR (CDCl₃, 2 sets of signals) δ 1.70–2.20 (m, 8H); 2.45–2.80 (m, 6H); 3.60 and 3.70 (t and m, together 2H); 4.20 and 4.40 (both m, together 1H); 6.75 and 6.90 (both d, together 1H); 7.30–7.50 (m, 3H); 7.60 (m, 6H); 7.75 (d, 1H). HPLC method A: elution at 10.26 min. MS: calc. for [M+H]⁺: 361; found: 361.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 29 (General Procedure (A))

4-[(E)-3-Oxo-3-((S)-2-((pyrrolidin-1-yl)methyl)pyrrolidin-1-yl)propenyl]benzonitrile

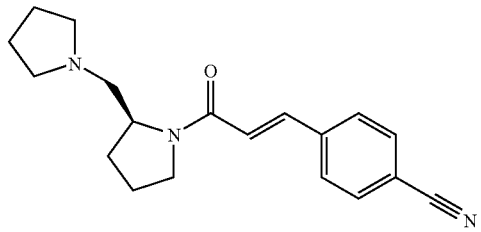

180 mg of the title compound were synthesized as described for (E)-3-(4-bromophenyl)-1-((S)-2-((pyrrolidin-1-yl)methyl)pyrrolidin-1-yl)propenone, using (E)-4-cyanocinnamic acid instead of (E)-4-bromocinnamic acid.

¹H-NMR (CDCl₃, 2 sets of signals) δ 1.75 (m, 4H); 1.85–2.20 (m, 4H); 2.40–2.75 (m, 6H); 3.55–3.75 (m, 2H); 4.15 and 4.40 (both m, together 1H); 6.80 and 7.00 (both d, together 1H); 7.55–7.70 (m, 5H). HPLC method A: elution at 7.46 min. MS: calc. for [M+H]⁺: 310; found: 310.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 30 (General Procedure (A))

(3-Chlorobenzo[b]thien-2-yl)-((S)-2-((pyrrolidin-1-yl)methyl)pyrrolidin-1-yl)methanone

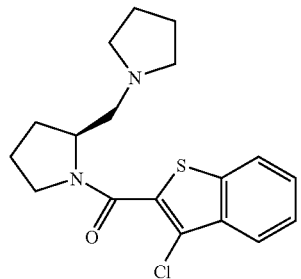

130 mg of the title compound were synthesized as described for (E)-3-(4-bromophenyl)-1-((S)-2-((pyrrolidin-1-yl)methyl)pyrrolidin-1-yl)propenone, using 3-chlorobenzo[b]thiophene-2-carboxylic acid instead of (E)-4-bromocinnamic acid.

¹H-NMR (CDCl₃, 2 sets of signals) δ 11.35–2.15 (m, 8H); 2.20–3.00 (m, 6H); 3.30–3.80 (m, 2H); 4.5–4.55 (m, 1H); 7.45 (m, 2H); 7.80 (m, 2H). HPLC method A: elution at 8.82 min. MS: calc. for [M+H]⁺: 349; found: 349.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 31 (General Procedure (A))

(3-Methoxybenzo[b]thien-2-yl)-((S)-2-((pyrrolidin-1-yl)methyl)pyrrolidin-1-yl)methanone

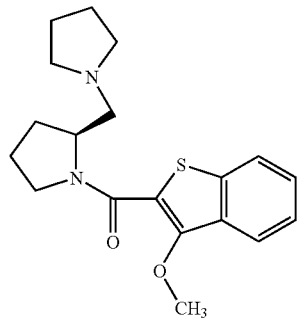

310 mg of the title compound were synthesized as described for (E)-3-(4-bromophenyl)-1-((S)-2-((pyrrolidin- 1-yl)methyl)pyrrolidin-1-yl)propenone, using 3-methoxy-benzo[b]thiophene-2-carboxylic acid instead of (E)-4-bromocinnamic acid.

$^{1}$H-NMR (CDCl$_{3}$, 2 sets of signals) δ 1.40–2.95 (m, 14H); 3.45–3.75 (m, 2H); 4.05 (s, 3H); 4.25–4.55 (m, 1H); 7.40 (m, 2H); 7.75 (m, 2H). HPLC method A: elution at 8.55 min. MS: calc. for [M+H]$^{+}$: 345; found: 345.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 32 (General Procedure (A))

(Benzo[b]thien-2-yl)-((S)-2-((pyrrolidin-1-yl)methyl)pyrrolidin-1-yl)methanone

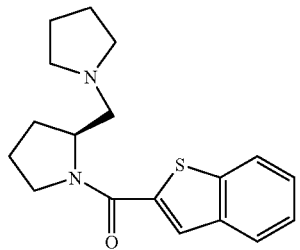

130 mg of the title compound were synthesized as described for (E)-3-(4-bromophenyl)-1-((S)-2-((pyrrolidin-1-yl)methyl)pyrrolidin-1-yl)propenone, using benzo[b]thiophene-2-carboxylic acid instead of (E)-4-bromocinnamic acid.

$^{1}$H-NMR (CDCl$_{3}$, 2 sets of signals) δ 1.55–1.85 (m, 4H); 1.85–2.15 (m, 4H); 2.60 (m, 5H); 2.80 (m, 1H); 3.85 (m, 2H); 4.55 (m, 1H); 7.40 (m, 2H); 7.70 (m, 1H); 7.85 (m, 2H). HPLC method A: elution at 8.35 min. MS: calc. for [M+H]$^{+}$: 315; found: 315.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 33 (General Procedure (A))

(5-Chlorobenzofuran-2-yl)-((S)-2-((pyrrolidin-1-yl)methyl)pyrrolidin-1-yl)methanone

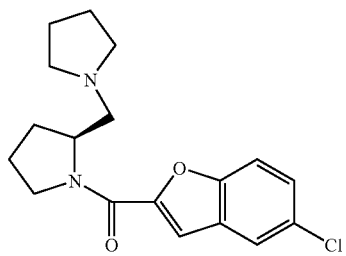

400 mg of the title compound were synthesized as described for (E)-3-(4-bromophenyl)-1-((S)-2-((pyrrolidin-1-yl)methyl)pyrrolidin-1-yl)propenone, using 5-chlorobenzo[b]furane-2-carboxylic acid instead of (E)-4-bromocinnamic acid.

$^{1}$H-NMR (CDCl$_{3}$, 2 sets of signals) δ 1.70 (m, 4H); 1.85–2.90 (m, 10H); 3.65–4.10 (m, 2H); 4.50 and 4.85(both m, together 1H); 7.30–7.50 (m, 3H); 7.65 (s, 1H). HPLC method A: elution at 8.62 min. MS: calc. for [M+H]$^{+}$: 333; found: 333.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 34 (General Procedure (A))

(7-(Ethoxy)benzofuran-2-yl)-((S)-2-((pyrrolidin-1-yl)methyl)pyrrolidin-1-yl)methanone

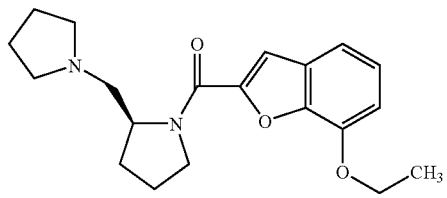

340 mg of the title compound were synthesized as described for (E)-3-(4-bromophenyl)-1-((S)-2-((pyrrolidin-1-yl)methyl)pyrrolidin-1-yl)propenone, using 7-(ethoxy)benzo[b]furane-2-carboxylic acid instead of (E)-4-bromocinnamic acid.

$^{1}$H-NMR (CDCl$_{3}$, 2 sets of signals) δ 1.50 (t, 3H); 1.60–1.85 (m, 4H); 1.85–2.15 (m, 4H); 2.15–2.90 (m, 6H); 3.70 (m, 1H); 3.90 and 4.05 (both m, together 1H); 4.20 (m, 2H); 4.50 and 5.00 (both m, together 1H); 6.85 (d, 1H); 7.10–7.30 (m, 2H); 7.30–7.55 (m, 1H). HPLC method A: elution at 8.67 min. MS: calc. for [M+H]$^{+}$: 343; found: 343.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 35 (General Procedure (A))

(E)-3-(4-(Methylsulfonyl)phenyl)-1-((S)-2-((pyrrolidin-1-yl)methyl)pyrrolidin-1-yl)propenone

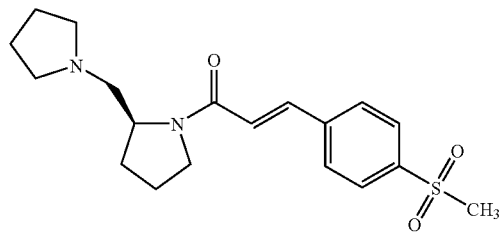

Step 1:
(E)-3-(4-(Methylsulfonyl)phenyl)acrylic Acid Ethyl Ester

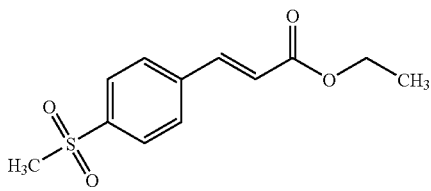

Potassium tert-butoxide (10.96 g, 98 mmol) in tetrahydrofuran (60 ml) was added portionwise to a solution of triethyl phosphonoacetate (21.91 g, 98 mmol) in tetrahydrofuran (150 ml). The reaction mixture was stirred for 40 min at room temp. A solution of 4-(methylsulfonyl)benzaldehyde (Acros no.: 42490-0025; 10.0 g, 54 mmol) in tetrahydrofuran (60 ml) was added dropwise. The reaction mixture was stirred for 1 h at room temp. It was diluted with ethyl acetate (500 ml) and washed with 1 N hydrochloric acid (300 ml): The aqueous phase was extracted with ethyl acetate (2×100 ml). The combined organic layers were dried over magnesium sulphate. The solvent was removed in vacuo. The crude product was purified by crystallization from ethyl acetate/heptane to give 4.3 g of (E)-3-(4-(methylsulfonyl)phenyl) acrylic acid ethyl ester.

$^{1}$H-NMR (CDCl$_3$) δ 1.35 (t, 3H); 3.10 (s, 3H); 4.30 (q, 2H); 6.55 (d, 1H); 7.70 (m, 3H); 7.95 (d 2H).

Step 2:
(E)-4-Methylsulfonylcinnamic Acid

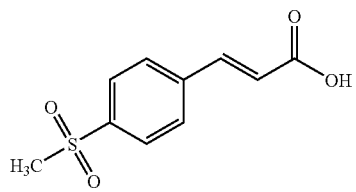

A solution of (E)-3-(4-(methylsulfonyl)phenyl)acrylic acid ethyl ester and lithium hydroxide in dioxane/water (100 ml/100 ml) was stirred for 16 h at room temp. It was washed with tert.-butyl methyl ether (200 ml). The aqueous phase was acidified with a 10% aqueous solution of sodium hydrogensulfate until pH 2. The precipitation was isolated by filtration and dried in vacuo. The residue was suspended in ethanol (100 ml). The solvent was removed. The latter procedure was repeated once to give 2.74 g of crude (E)-4-methylsulfonylcinnamic acid which was used in the next step without further purification.

$^{1}$H-NMR (DMSO-d$_6$) δ 3.25 (s, 3H); 6.70 (d, 1H); 7.65 (d, 1H); 7.95 (AB, 4H); 12.60 (br, 1H).

Step 3
340 mg of the title compound were synthesized as described for (E)-3-(4-bromophenyl)-1-((S)-2-((pyrrolidin-1-yl)methyl)pyrrolidin-1-yl)propenone, using (E)-4-methylsulfonylcinnamic acid instead of (E)-4-bromocinnamic acid.

$^{1}$H-NMR (CDCl$_3$, 2 sets of signals) δ 1.75 (m, 4H); 1.85–2.20 (m, 4H); 2–45–2.80 (m, 6H); 3.05 (s, 3H); 3.55–3.80 (m, 2H); 4.10 and 4.40 (both m, together 1H); 6.85 and 7.05 (both d, together 1H); 7.65 (m, 3H); 7.95 (d, 1H). HPLC method A: elution at 6.58 min. MS: calc. for [M+H]$^+$: 363; found: 363.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 36 (General Procedure (A))

(E)-3-(4-Chlorophenyl)-1-(2-((pyrrolidin-1-yl)methyl)piperidin-1-yl)propenone

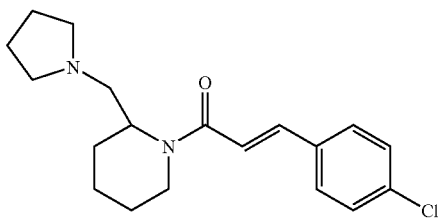

140 mg of the title compound were synthesized as described for (E)-3-(4-bromophenyl)-1-((S)-2-((pyrrolidin-1-yl)methyl)pyrrolidin-1-yl)propenone, using (E)-4-chlorocinnamic acid instead of (E)-4-bromocinnamic acid and 2-formylpiperidine-1-carboxylic acid tert-butyl ester instead of (S)-2-formylpyrrolidine-1-carboxylic acid tert-butyl ester.

$^{1}$H-NMR (CDCl$_3$, 2 sets of signals) δ 1.35–1.95 (m, 10H); 2.40–2.90 and 3.20 (both m, together 7H); 3.90 and 4.25 (both m, together 1H); 4.60 and 5.05 (both m, together 1H); 6.90 (d, 1H); 7.35 (d, 2H); 7.45 (d, 2H); 7.55 (d, 1H). HPLC method A: elution at 12.39 min. MS: calc. for [M+H]$^+$: 333, found: 333.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 37 (General Procedure (A))

(E)-3-(4-Bromophenyl)-1-(2-((pyrrolidin-1-yl)methyl)piperidin-1-yl)propenone

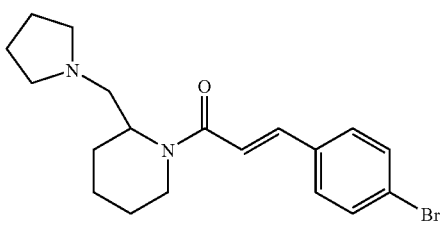

90 mg of the title compound were synthesized as described for (E)-3-(4-bromophenyl)-1-((S)-2-((pyrrolidin-1-yl)methyl)pyrrolidin-1-yl)propenone, using 2-formylpiperidine-1-carboxylic acid tert-butyl ester instead of (S)-2-formylpyrrolidine-1-carboxylic acid tert-butyl ester.

$^{1}$H-NMR (CDCl$_3$, 2 sets of signals) 1.35–1.90 (m, 10H); 2.40–2.90 (m, 7H); 3.90 and 4.25 (both m, together 1H); 4.60 and 5.05 (both m, together 1H); 6.95 (d, 1H); 7.35 (d, 2H); 7.45–7.65 (m, 3H). HPLC method B: elution at 4.28 min. MS: calc. for [M+H]+: 377; found: 377.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 38 (General Procedure (A))

(E)-1-(2-((Pyrrolidin-1-yl)methyl)piperidin-1-yl)-3-(4-(trifluoromethyl)phenyl)propenone

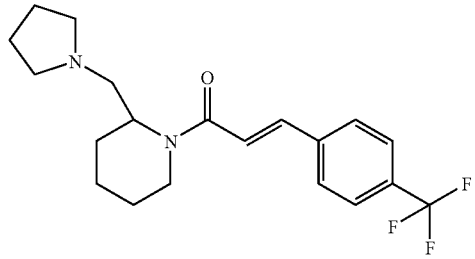

130 mg of the title compound were synthesized as described for (E)-3-(4-bromophenyl)-1-((S)-2-((pyrrolidin-1-yl)methyl)pyrrolidin-1-yl)propenone, using (E)-4-(trifluoromethyl)cinnamic acid instead of (E)-4-bromocinnamic acid and formylpiperidine-1-carboxylic acid tert-butyl ester instead of (S)-2-formylpyrrolidine-1-carboxylic acid tert-butyl ester.

1H-NMR (CDCl3, 2 sets of signals) δ 1.40–1.95 (m, 10H); 2.45–2.85 (m, 7H); 3.90–4.25 (both m, together 1H); 4.60 and 5.00 (both m, together 1H); 7.00 (d, 1H); 7.55–7.65 (m, 5H). HPLC method B: elution at 4.44 min. MS: calc. for [M+H]+: 367; found. 367.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 39 (General Procedure (A))

(E)-3-(4-Methoxyphenyl)-1-(2-((pyrrolidin-1-yl)methyl)piperidin-1-yl)propenone

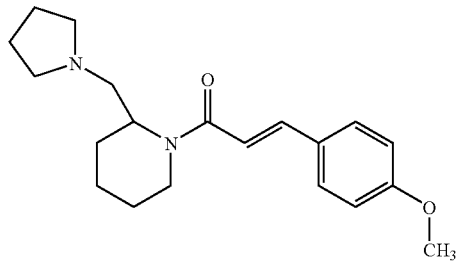

100 mg of the title compound were synthesized as described for (E)-3-(4-bromophenyl)-1-((S)-2-((pyrrolidin-1-yl)methyl)pyrrolidin-1-yl)propenone, using (E)-4-chlorocinnamic acid instead of (E)-4-bromocinnamic acid and 2-formylpiperidine-1-carboxylic acid tert-butyl ester instead of (S)-2-formylpyrrolidine-1-carboxylic acid tert-butyl ester.

1H-NMR (CDCl3, 2 sets of signals) δ 1.30–1.95 (m, 10H); 2.40–3.20 (m, 7H); 3.85 (s, 3H); 4.00 and 4.25 (both m, together 1H); 4.60 and 5.00 (both m, together 1H); 6.80 (d, 1H); 6.90 (d, 2H); 7.45 (d, 2H); 7.60 (d, 1H). HPLC method B: elution at 3.79 min. MS: calc. for [M+H]+: 329; found: 329.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 40 (General Procedure (A))

(E)-1-((S)-((2-Pyrrolidin-1-yl)methyl)pyrrolidin-1-yl)-3-(thien-2-yl)propenone

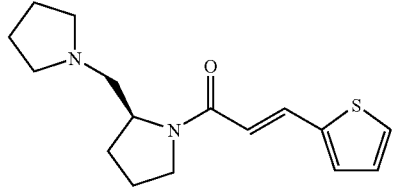

160 mg of the title compound were synthesized as described for (E)-3-(4-bromophenyl)-1-((S)-2-((pyrrolidin-1-yl)methyl)pyrrolidin-1-yl)propenone, using (E)-3-(thien-2-yl)acrylic acid instead of (E)-4-bromocinnamic acid.

1H-NMR (CDCl3, 2 sets of signals) δ 1.80 (m, 4H); 1.85–2.15 (m, 4H); 2.35–2.75 (m, 6H); 3.50–3.70 (m, 2H); 4.10 and 4.35 (both m, together 1H); 6.52 and 6.65 (both d, together 1H); 7.05 (m, 1H); 7.20 (m, 1H); 7.30 (m, 1H); 7.80 (d, 1H). HPLC method A: elution at 7.34 min. MS: calc. for [M+H]+: 291; found: 291.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 41 (General Procedure (A))

(E)-1-((S)-2-((Pyrrolidin-1-yl)methyl)pyrrolidin-1-yl)-3-(thien-3-yl)propenone

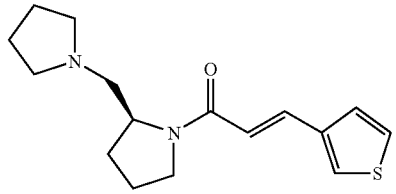

100 mg of the title compound were synthesized as described for (E)-3-(4-bromophenyl)-1-((S)-2-((pyrrolidin-1-yl)methyl)pyrrolidin-1-yl)propenone, using (E)-3-(thien-3-yl)acrylic acid instead of (E)-4-bromocinnamic acid.

¹H-NMR (CDCl₃, 2 sets of signals) δ 1.75 (m, 4H); 1.85–2.20 (m, 4H); 2.40–2.80 (m, 6H); 3.50–3.75 (m, 2H); 4.15 and 4.40 (both m, together 1H); 6.55 and 6.70 (both d, together 1H); 7.20–7.35 (m, 2H); 7.45 (m, 1H); 7.70 (dd, 1H). HPLC method A: elution at 7.32 min. MS: calc. for [M+H]⁺: 291; found: 291.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 42 (General Procedure (A))

(E)-3-(Furan-2-yl)-1-((S)-2-((pyrrolidin-1-yl)methyl)pyrrolidin-1-yl)propenone

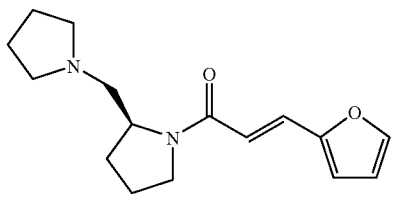

78 mg of the title compound were synthesized as described for (E)-3-(4-bromophenyl)-1-((S)-2-((pyrrolidin-1-yl)methyl)pyrrolidin-1-yl)propenone, using (E)-3-(furan-2-yl)acrylic acid instead of (E)-4-bromocinnamic acid.

¹H-NMR (CDCl₃, 2 sets of signals) δ 1.70 (m, 4H); 1.85–2.20 (m, 4H); 2.40–2.80 (m, 6H); 3.50–3.75 (m, 2H); 4.15 and 4.40 (both m, together 1H); 6.45 (m, 1H); 6.55 (m, 1H); 6.65 and 6.75 (both d, together 1H); 7.45 (m, 2H). HPLC method A: elution at 6.78 min. MS: calc. for [M+H]⁺: 275; found: 275.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 43 (General Procedure (A))

(E)-3-(Furan-3-yl)-1-((S)-2-((pyrrolidin-1-yl)methyl)pyrrolidin-1-yl)propenone

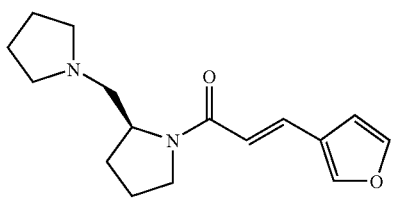

190 mg of the title compound were synthesized as described for (E)-3-(4-bromophenyl)-1-((S)-2-((pyrrolidin-1-yl)methyl)pyrrolidin-1-yl)propenone, using (E)-3-(furan-3-yl)acrylic acid instead of (E)-4-bromocinnamic acid.

¹H-NMR (CDCl₃, 2 sets of signals) δ 1.75 (m, 4H); 1.85–2.20 (m, 4H); 2.40–2.75 (m, 6H); 3.45–3.70 (m, 2H); 4.10 and 4.35 (both m, together 1H); 6.45 and 6.55 (d and m, together 2H); 7.40 (s, 1H); 7.55–7.65 (m, together 2H). HPLC method A: elution at 6.66 min. MS: calc. for [M+H]⁺: 275; found: 275.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 44 (General Procedure (A))

Methanesulfonic Acid 4-[(E)-3-oxo-3-((S)-2-((pyrrolidin-1-yl)methyl)pyrrolidin-1-yl)propenyl]phenyl Ester

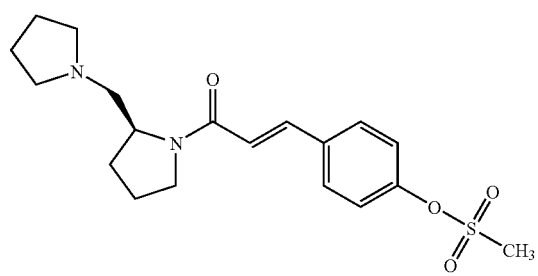

Step 1: Methanesulfonic Acid 4-formylphenyl Ester

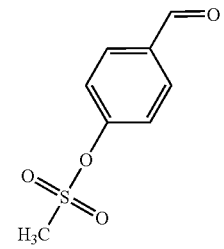

At 0° C., methanesulfonyl chloride (9.51 ml, 0.123 mol) was added to a solution of 4-hydroxybenzaldehyde (15 g, 0.123 mol) in pyridine (12.91 ml, 0.160 mol). The reaction mixture was stirred at 0° C. for 3 h and left at room temperature for 16 h. It was given onto conc. hydrochloric acid/ice (200 ml/200 ml). The mixture was extracted with ethyl acetate (4×300 ml). The combined organic layers were washed with a 5% aqueous solution of sodium hydrogen carbonate (3×200 ml) and brine (100 ml). They were dried over magnesium sulphate. The solvent was removed in vacuo to give 22.87 g of crude methanesulfonic acid 4-formylphenyl ester, which was used in the next step without further purification.

¹H-NMR (CDCl₃) δ 13.22 (s, 3H); 7.45 (d, 2H); 8.00 (d, 2H); 10.02 (s, 1H).

Step 2:

(E)-3-(4-(Methanesulfonyloxy)phenyl)acrylic Acid

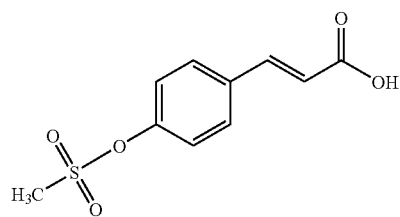

Malonic acid (7.80 g, 74.92 mmol) was added to a solution of the crude methanesulfonic acid 4-formylphenyl ester (10 g, 49.95 mmol), which was synthesized in the preceeding step, and piperidine (0.7 ml, 7.09 mmol) in pyridine (50 ml). The reaction mixture was heated to 90° C. for 2.5 h. It was cooled to room temperature. Concentrated hydrochloric acid/ice (400 ml/100 ml) was added. The precipitation was filtered off and washed with a 10% aqueous solution of acetic acid (200 ml). It was dried in vacuo to give 6.95 g of (E)-3-(4-(methanesulfonyloxy)phenyl)acrylic acid.

$^1$H-NMR (DMSO-d$_6$) δ 3.40 (s, 3H); 6.55 (d, 1H); 7.40 (d, 2H); 7.60 (d, 1H); 7.80 (d, 2H).

Step 3:

150 mg of the title compound were synthesized as described for (E)-3-(4-bromophenyl)-1-((S)-2-((pyrrolidin-1-yl)methyl)pyrrolidin-1-yl)propenone, using (E)-3-(4-(methanesulfonyloxy)phenyl)acrylic acid instead of (E)-4-bromocinnamic acid.

$^1$H-NMR (CDCl$_3$, 2 sets of signals) δ 1.75 (m, 4H); 1.85–2.20 (m, 4H); 2.40–2.80 (m, 5H); 3.15 (s, 3H); 3.50–3.75 (m, 2H); 4.15 and 4.40 (m, 1H); 6.70 and 6.85 (both d, together 1 H); 7.30 (m, 2H); 7.55 (d, 2H); 7.65 (d, 1H). HPLC method A: elution at 7.50 min. MS: calc. for [M+H]$^+$: 379; found: 379.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 45 (General Procedure (A))

Trifluoromethanesulfonic Acid 4-[(E)-3-oxo-3-((S)-2-((pyrrolidin-1-yl)methyl)pyrrolidin-1-yl)propenyl]phenyl Ester

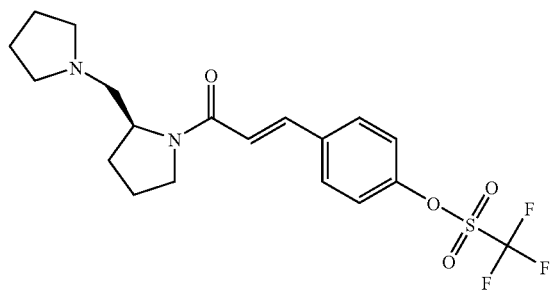

Step 1:

(E)-3-(4-(Trifluoromethylsulfonyloxy)phenyl)acrylic Acid 13.4 g of (E)-3-(4-(trifluoromethylsulfonyloxy)phenyl) acrylic acid was synthesized as described for (E)-3-(4-(methanesulfonyloxy)phenyl)acrylic acid using trifluoromethansulfonic acid anhydride methanesulfonyl chloride.

$^1$H-NMR (DMSO-d$_6$) δ 6.60 (d, 1H); 7.55 (d, 2H); 7.65 (d, 1H); 7.90 (d, 2H).

Step 2:

130 mg of the title compound were synthesized as described for (E)-3-(4-bromophenyl)-1-((S)-2-((pyrrolidin-1-yl)methyl)pyrrolidin-1-yl)propenone, using (E)-3-(4-(trifluoromethylsulfonyloxy)phenyl)acrylic acid instead of (E)-4-bromocinnamic acid.

$^1$H-NMR (CDCl$_3$, 2 sets of signals) δ 1.75 (m, 4H); 1.85–2.15 (m, 4H); 2.40–2.80 (m, 5H); 3.55–3.75 (m, 2H); 4.15 and 4.40 (both m, together 1H); 6.70 and 6.90 (both d, together 1H); 7.30 (d, 2H); 7.60 (d, 2H); 7.65 (d,1H). HPLC method A: elution at 9.97 min. MS: calc. for [M+H]$^+$: 433; found: 433.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 46 (General Procedure (A))

3-[(E)-3-Oxo-3-((S)-2-((pyrrolidin-1-yl)methyl)pyrrolidin-1-yl)propenyl]benzonitrile

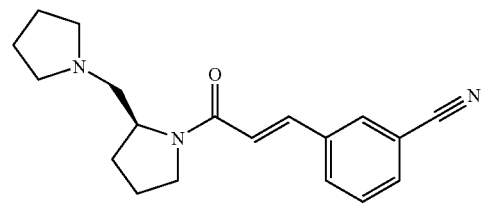

Step 1:

(E)-3-(3-Cyanophenyl)acrylic Acid 11.3 g of (E)-3-(3-cyanophenyl)acrylic acid were synthesized as described for (E)-3-(4-(methanesulfonyloxy)phenyl)acrylic acid, using3-cyanobenzaldehyde (commercially available at Aldrich) instead of methanesulfonic acid 4-formylphenyl ester.

$^1$H-NMR (DMSO-d$_6$) δ 6.70 (d, 1H); 7.60 (m, 2H); 7.85 (d, 1H); 8.05 (d, 1H); 8.25 (s, 1H); 12.50 (br, 1H).

Step 2:

220 mg of the title compound were synthesized as described for (E)-3-(4-bromophenyl)-1-((S)-2-((pyrrolidin-1-yl)methyl)pyrrolidin-1-yl)propenone, using (E)-3-(3-cyanophenyl)acrylic acid instead of (E)-4-bromocinnamic acid.

$^1$H-NMR (as trifluoroacetic acid salt, CDCl$_3$) δ 1.90 (m, 1H); 2.00–2.30 (m, 7H); 3.05–3.20 (m, 2H); 3.25 (m, 1H); 3.65 (m, 1H); 3.70–3.90 (m, 3H); 4.15 (m, 1H); 4.50 (m, 1H); 6.75 (d, 1 H); 7.55 (t, 1H); 7.65 (d, 1H); 7.70 (d, 1H); 7.75 (d, 1H); 7.85 (s, 1H). HPLC method A: elution at 7.37 min. MS: calc. for [M+H]$^+$: 310; found:. 310.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 47 (General Procedure (A))

(E)-1-((S)-2-((Piperidin-1-yl)methyl)pyrrolidin-1-yl)-3-(3-trifluoromethylphenyl)propenone

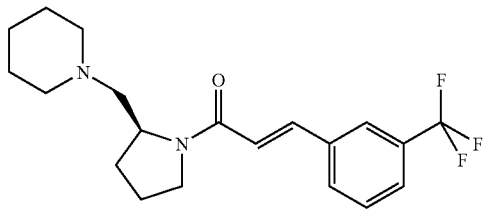

310 mg of the title compound were synthesized as described for (E)-3-(4-bromophenyl)-1-((S)-2-((pyrrolidin-1-yl)methyl)pyrrolidin-1-yl)propenone, using 1-(((S)-pyrrolidin-2-yl)methyl)piperidine instead of (S)-2-((pyrrolidin-1-yl)methyl)pyrrolidine and (E)-3-(trifluoromethyl)cinnamic acid instead of (E)-4-bromocinnamic acid.

$^1$H-NMR (CDCl$_3$, 2 sets of signals) δ 1.40 (m, 2H); 1.55 (m, 4H); 1.80–2.15 (m, 4H); 2.15–2.70 (m, 6H); 3.60 and 3.70 (both m, together 2H); 4.15 and 4.40 (both m, together 1H); 6.80 and 7.05 (both d, together 1H); 7.45–7.85 (m, together 5H). HPLC method A: elution at 9.73 min. MS: calc. for [M+H]$^+$: 367; found: 367.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 48 (General Procedure (A))

3-[(E)-3-Oxo-3-((S)-2-((piperidin-1-yl)methyl)pyrrolidin-1-yl)propenyl]benzonitrile

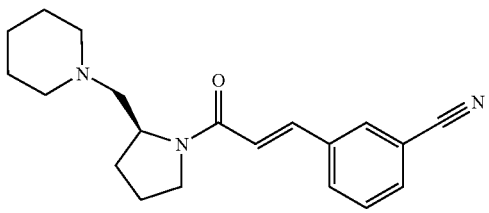

370 mg of the title compound were synthesized as described for (E)-3-(4-bromophenyl)-1-((S)-2-((pyrrolidin-1-yl)methyl)pyrrolidin-1-yl)propenone, using (E)-3-(3-cyanophenyl)acrylic acid instead of (E)-4-bromocinnamic acid and 1-(((S)-pyrrolidin-2-yl)methyl)piperidine instead of (S)-2-((pyrrolidin-1-yl)methyl)pyrrolidine.

$^1$H-NMR (CDCl$_3$, 2 sets of signals) δ 1.40 (m, 2H); 1.55 (m, 4H); 1.85–2.15 (m, 4H); 2.15–2.55 (m, 5H); 2.65 (m, 1H); 3.60 and 3.75 (both m, together 2H); 4.15 and 4.40 (both m, together 1H); 6.75 and 7.05 (both d, together 1H); 7.50 (t, 1H); 7.60–7.75 (m, 4H); 7.85 (d, 1H). HPLC method B: elution at 3.10 min. MS: calc. for [M+H]$^+$: 324; found: 324.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 49 (General Procedure (A))

4-[(E)-3-Oxo-3-((S)-2-((piperidin-1-yl)methyl)pyrrolidin-1-yl)propenyl]benzonitrile

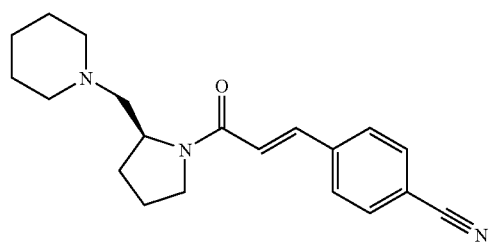

150 mg of the title compound were synthesized as described for (E)-3-(4-bromophenyl)-1-((S)-2-((pyrrolidin-1-yl)methyl)pyrrolidin-1-yl)propenone, using (E)-4-cyanocinnamic acid instead of (E)-4-bromocinnamic acid and 1-(((S)-pyrrolidin-2-yl)methyl)piperidine instead of (S)-2-((pyrrolidin-1-yl)methyl)pyrrolidine.

$^1$H-NMR (CDCl$_3$, 2 sets of signals) δ 1.30–1.65 (m, 6H); 1.95–2.15 (m, 4H); 2.15–2.70 (m, 6 H); 3.60 and 3.70 (both m, together 2H); 4.15 and 4.40 (both m, together 1H); 6.80 and 7.05 (both d, together 1H); 7.50–7.70 (m, 5H). HPLC method B: elution at 3.05 min. MS: calc. for [M+H]$^+$: 324; found: 324.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 50 (General Procedure (A))

(E)-3-(4-(Methylsulfonyl)phenyl)-1-((S)-2-((piperidin-1-yl)methyl)pyrrolidin-1-yl)propenone

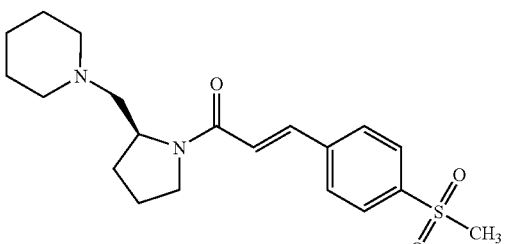

190 mg of the title compound were synthesized as described for (E)-3-(4-bromophenyl)-1-((S)-2-((pyrrolidin-1-yl)methyl)pyrrolidin-1-yl)propenone, using (E)-4-methylsulfonylcinnamic acid instead of (E)-4-bromocinnamic acid 1-(((S)-pyrrolidin-2-yl)methyl)piperidine instead of (S)-2-((pyrrolidin-1-yl)methyl)pyrrolidine.

$^1$H-NMR (CDCl$_3$, 2 sets of signals) δ 1.45 (m, 2H); 1.50–1.70 (m, 4H); 1.85–2.15 (m, 4H); 2.15–2.70 (m, 6H); 3.10 (s, 3H); 3.65 and 3.75 (both m, together 2H); 4.20 and 4.40 (both m, together 1H); 6.85 and 7.10 (both d, together 1H); 7.70 (m, 3H); 7.95 (d, 2H). HPLC method B: elution at 2.60 min. MS: calc. for [M+H]⁺: 377; found: 377.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 51 (General Procedure (A))

Methanesulfonic Acid 4-[(E)-3-oxo-3-((S)-2-((piperidin-1-yl)methyl)pyrrolidin-1-yl)propenyl]phenyl Ester

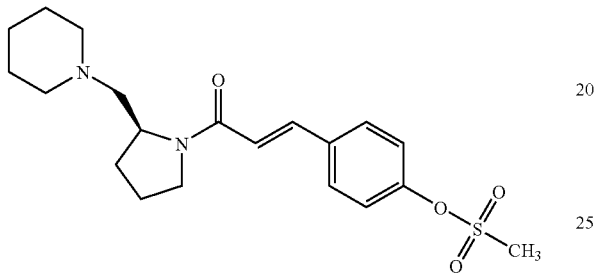

230 mg of the title compound were synthesized as described for (E)-3-(4-bromophenyl)-1-((S)-2-((pyrrolidin-1-yl)methyl)pyrrolidin-1-yl)propenone, using (E)-3-(4-(methanesulfonyloxy)phenyl)acrylic acid instead of (E)-4-bromocinnamic acid and 1-(((S)-pyrrolidin-2-yl)methyl)piperidine instead of (S)-2-((pyrrolidin-1-yl)methyl)pyrrolidine.

¹H-NMR (CDCl₃, 2 sets of signals) δ 1.45 (m, 2H); 1.55 (m, 4H); 1.70–2.15 (m, 4H); 2.15–2.70 (m, 6H); 3.15 (s, 3H); 3.60 and 3.70 (both m, together 2H); 4.15 and 4.35 (both m, together 1H); 6.70 and 6.90 (both d, together 1H); 7.30 (d, 2H); 7.55 (d, 2H); 7.65 (d, 1H). HPLC method B: elution at 3.17 min. MS: calc. for [M+H]⁺: 393, found: 393.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 52 (General Procedure (A))

Trifluoromethanesulfonic Acid 4-[(E)-3-oxo-3-((S)-2-((piperidin-1-yl)methyl)pyrrolidin-1-yl)propenyl] phenyl Ester

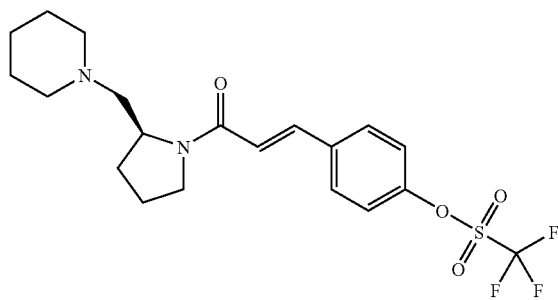

190 mg of the title compound were synthesized as described for (E)-3-(4-bromophenyl)-1-((S)-2-((pyrrolidin-1-yl)methyl)pyrrolidin-1-yl)propenone, using (E)-3-(4-(trifluoromethylsulfonyloxy)phenyl)acrylic acid instead of (E)-4-bromocinnamic acid 1-(((S)-pyrrolidin-2-yl)methyl)piperidine instead of (S)-2-((pyrrolidin-1-yl)methyl)pyrrolidine.

¹H-NMR (CDCl₃, 2 sets of signals) δ 1.30–2.70 (m, 16H); 3.60 and 3.70 (both m, together 2 H); 4.15 and 4.40 (both m, together 1H); 6.70 and 6.95 (both d, together 1H); 7.30 (d, 2H); 7.60 (d, 2H); 7.65 (d, 1H). HPLC method B: elution 4.45 min. MS: calc. for [M+H]⁺: 447; found: 447.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 53 (General Procedure (A))

2-Fluoro-5-[(E)-3-oxo-3-((S)-2-((piperidin-1-yl)methyl)pyrrolidin-1-yl)propenyl]benzonitrile

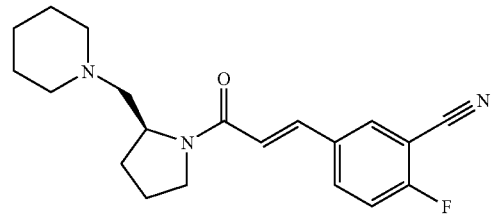

Step 1:
(E)-3-(3-Cyano-4-fluorophenyl)acrylic Acid

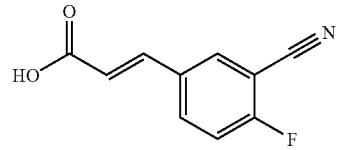

5.52 g of (E)-3-(3-cyano-4-fluorophenyl)acrylic acid was synthesized as described for (E)-3-(4-(methanesulfonyloxy)phenyl)acrylic acid, using 4-fluoro-3-cyanobenzaldehyde (commercially available at Aldrich) instead of methanesulfonic acid 4-formylphenyl ester.

¹H-NMR (DMSO-d₆) δ 6.60 (d, 1H); 7.55 (m, 2H); 8.15 (m, 1H); 8.35 (dd, 1H); 12.50 (br, 1H).

Step 2:
300 mg of the title compound were synthesized as described for (E)-3-(4-bromophenyl)-1-((S)-2-((pyrrolidin-1-yl)methyl)pyrrolidin-1-yl)propenone, using (E)-3-(3-cyano-4-fluorophenyl)acrylic acid instead of (E)-4-bromocinnamic acid and 1-(((S)-pyrrolidin-2-yl)methyl)piperidine instead of (S)-2-((pyrrolidin-1-yl)methyl)pyrrolidine.

¹H-NMR (CDCl₃, 2 sets of signals) δ 1.45 (m, 2H); 1.55 (m, 4H); 2.85–2.10 (m, 4H); 2.15–2.55 (m, 5H); 2.65 (m, 1H); 3.60 and 3.70 (both m, together 2H); 4.15 and 4.40 (both m, together 1H); 6.70 and 7.00 (both d, together 1H); 7.20 (m, 1H); 7.60 (dd, 1H); 7.70 (m, 1H); 7.80 (m, 1H). HPLC method B: elution MS: calc. for [M+H]⁺: 342; found: 342.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 54 (General Procedure (A))

(E)-3-(2-Fluoro-4-trifluoromethylphenyl)-1-((S)-2-((piperidin-1-yl)methyl)pyrrolidin-1-yl)propenone

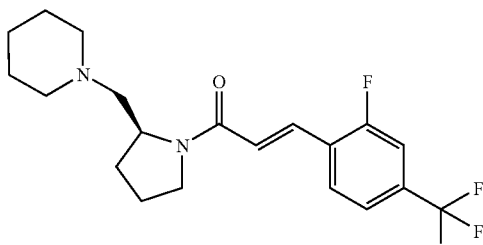

Step 1:
(E)-2-Fluoro-4-(trifluoromethyl)cinnamic Acid

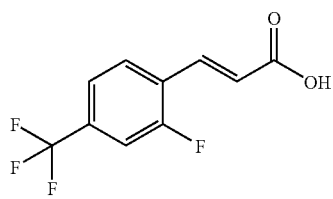

5.12 g of (E)-2-Fluoro-4-(trifluoromethyl)cinnamic acid were synthesized as described for (E)-3-(4-(methanesulfonyloxy)phenyl)acrylic acid using 2-fluoro-4-trifluoromethylbenzaldehyde (commercially available from Aldrich) instead of methanesulfonic acid 4-formylphenyl ester.

$^1$H-NMR (DMSO-$d_6$) δ 6.70 (d, 1H); 7.65 (m, 2H); 7.80 (d, 1H); 8.10 (t, 1H). 12.00 (br, 1H).

Step 2:

220 mg of the title compound were synthesized as described for (E)-3-(4-bromophenyl)-1-((S)-2-((pyrrolidin-1-yl)methyl)pyrrolidin-1-yl)propenone, using (E)-2-fluoro-4-(trifluoromethyl)cinnamic acid instead of (E)-4-bromocinnamic acid and 1-(((S)-pyrrolidin-2-yl)methyl)piperidine instead of (S)-2-((pyrrolidin-1-yl)methyl)pyrrolidine.

$^1$H-NMR (CDCl$_3$, 2 sets of signals) δ 1.40 (m, 2H); 1.55 (m, 4H); 1.75–2.15 (m, 4H); 2.15–2.70 (m, 6H); 3.60 and 3.70 (both m, together 2H); 4.15 and 4.40 (both m, together 1H); 6.95 and 7.15 (both d, together 1H); 7.30–7.45 (m, 2H); 7.60 m, 1H); 7.65–7.80 (m, 2H). HPLC method B: elution at 4.54 min. MS: calc. for [M+H]$^+$: 385; found: 385.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 55 (General Procedure (A))

(General Procedure (C)): (E)-3-(2-Fluoro-4-trifluoromethylphenyl)-1-((S)-2-((pyrrolidin-1-yl)methyl) pyrrolidin-1-yl)propenone

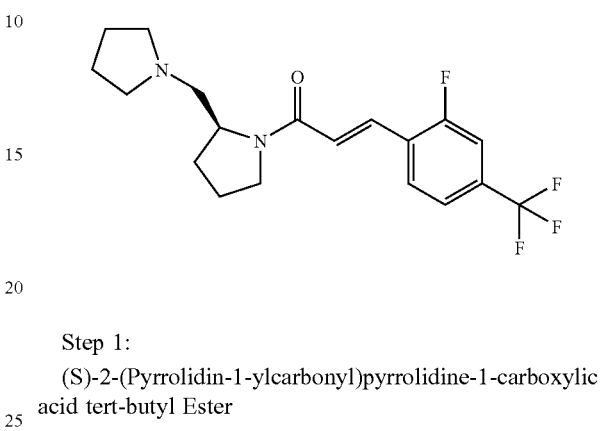

Step 1:
(S)-2-(Pyrrolidin-1-ylcarbonyl)pyrrolidine-1-carboxylic acid tert-butyl Ester

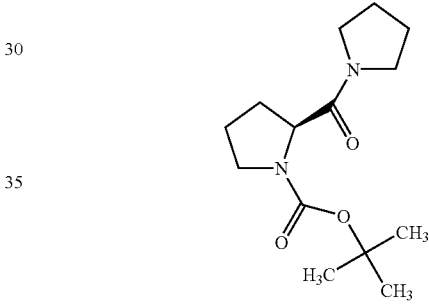

Ar 0° C., 1-(3-dimethylaminopropyl)-3-ethylcarbodiimide hydrochloride salt (17.81 g, 93 mmol) was added to a solution of (S)-1-(tert-butoxycarbonyl)pyrrolidine-1-carboxylic acid (20.0 g, 93 mmol) and 3-hydroxy-1,2,3-benzotriazin-4(3H)-one (15.2 g, 93 mmol) in a mixture of dichloromethane (150 ml) and N,N-dimethylformamide (150 ml). The reaction mixture was stirred for 20 min at 0° C. Pyrrolidine (7.76 ml, 93 mmol) and triethylamine (91 ml, 650 mmol) were added successively. The reaction mixture was stirred for 16 h, while it was warming up to room temperature. It was diluted with ethyl acetate (500 ml) and washed with a mixture of water and a saturated aqueous solution of sodium hydrogencarbonate (250 ml/250 ml). The aqueous solution was dried over magnesium sulphate. The solvent was removed in vacuo. The crude product was purified by flash chromatography on silica (90 g), using dichloromethane/methanol/25% aqueous ammonia (100:10:1) as eluent, to give 5.9 g of (S)-2-(pyrrolidin-1-ylcarbonyl) pyrrolidine-1-carboxylic acid tert-butyl ester.

$^1$H-NMR (CDCl$_3$, 2 sets of signals) δ 1.40 and 1.45 (both s, together 9H); 1.75–2.25 (m, 8H); 3.35–3.80 (m, 6H); 4.35 and 4.50 (both dd, together 1H). HPLC method A: elution at 9.35 min. MS: calc. for [M+H]$^+$: 269; found: 269.

Step 2:
(Pyrrolidin-1-yl)-((S)-pyrrolidin-2-yl)methanone

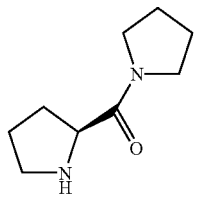

(S)-2-(Pyrrolidin-1-ylcarbonyl)pyrrolidine-1-carboxylic acid tert-butyl ester (5.90 g, 22 mmol) was dissolved in dichloromethane (50 ml) Trifluoroacetic acid (30 ml) was added. The reaction mixture was stirred for 50 min at room temperature. The solvent was removed in vacuo. The residue was dissolved in a saturated aqueous solution of potassium carbonate (200 ml). It was extracted with dichloromethane (3×100 ml). The aqueous phase was saturated with sodium chloride and extracted with dichloromethane (3×200 ml). The combined organic layers were dried over magnesium sulphate. The solvent was removed in vacuo to give 4.89 g of the crude (pyrrolidin-1-yl)-((S)-pyrrolidin-2-yl)methanone, which was used in the next step without further purification.

$^1$H-NMR (CDCl$_3$) δ 1.90 (m, 7H); 2.25 (m, 1H); 3.10–3.70 (m, 6H); 4.10 (m, 1H); 4.60 br, 1H).

Step 3
(S)-2-((Pyrrolidin-1-yl)methyl)pyrrolidine

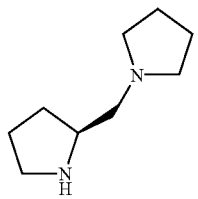

A 1.0 M solution of lithium aluminium hydride in tetrahydrofuran (87 ml, 87 mmol) was added dropwise to a solution of the crude (pyrrolidin-1-yl)-((S)-pyrrolidin-2-yl) methanone (4.89 g, 29 mmol) in tetrahydrofuran (90 ml). The reaction mixture was heated to reflux for 6 h. It was cooled to room temperature. Water (3.6 ml) was added carefully. A 1 N solution of sodium hydroxide (3.6 ml, 3.6 mmol) was added carefully. Water (10.7 ml) was added. The mixture was stirred for 1 h at room temperature. The precipitation was filtered off. The solvent was removed in vacuo to give 2.67 g of (S)-2-((pyrrolidin-1-yl)methyl)pyrrolidine.

$^1$H-NMR (CDCl$_3$) δ 1.25–2.00 (m, 8H); 2.30–2.70 (m, 6H); 2.85 (m, 1H); 3.00 (m, 1H); 3.20 (m, 1H).

Step 4:

220 mg of the title compound were synthesized as described in step 4 for the preparation of (E)-3-(4-bromophenyl)-1-((S)-2-((pyrrolidin-1-yl)methyl)pyrrolidin-1-yl)propenone, using (E)-2-fluoro-4-(trifluoromethyl)cinnamic acid instead of (E)-4-bromocinnamic acid.

$^1$H-NMR (CDCl$_3$, 2 sets of signals) δ 1.45–1.85 (m, 4H); 1.85–2.20 (m, 4H); 2.40–2.75 (m, 6 H); 3.60 and 3.70 (both m, together 2H); 4.15 and 4.40 (both m, together 1H); 6.95 and 7.15 (both d, together 1H); 7.40 (m, 2H); 7.60 (m, 1H); 7.75 (m, 1H). HPLC method B: elution at 4.31 min. MS: calc. for [M+H]$^+$: 371; found: 371.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 56 (General Procedure (A))

2-Fluoro-5-[(E)-3-oxo-3-((S)2-((pyrrolidin-1-yl) methyl)pyrrolidin-1-yl)propenyl]benzonitrile

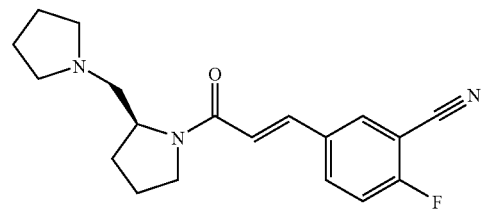

250 mg of the title compound were synthesized as described for (E)-3-(4-bromophenyl)-1-((S)-2-((pyrrolidin-1-yl)methyl)pyrrolidin-1-yl)propenone, using (E)-3-(3-cyano-4-fluorophenyl)acrylic acid instead of (E)-4-bromocinnamic acid.

$^1$H-NMR (CDCl$_3$, 2 sets of signals) δ 1.55–2.15 (m, 8H); 2.40–2.75 (m, 6H); 3.65 and 3.70 (both m, together 2H); 4.15 and 4.40 (both m, together 1H); 6.70 and 6.95 (both d, together 1H); 7.25 (t, 1H); 7.60 (d, 1H); 7.70 (m, 1H); 7.80 (m, 1H). HPLC method B: elution at 3.59 min. MS: calc. for [M+H]$^+$: 328; found: 328.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 57 (General Procedure (A))

(E)-1-((S)-2-((Pyrrolidin-1-yl)methyl)pyrrolidin-1-yl)-3-(3-(trifluoromethyl)phenyl)propenone

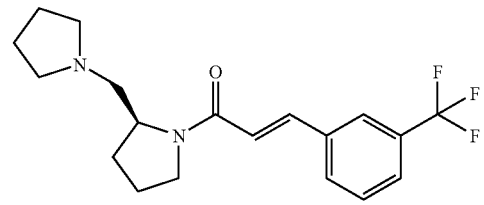

320 mg of the title compound were synthesized as described for (E)-3-(4-bromophenyl)-1-((S)-2-((pyrrolidin-1-yl)methyl)pyrrolidin-1-yl)propenone, using (E)-3-(tifluoromethyl)cinnamic acid instead of (E)-4-bromocinnamic acid.

$^1$H-NMR (CDCl$_3$, 2 sets of signals) δ 1.75 (m, 4H); 1.85–2.25 (m, 4H); 2.45–2.80 (m, 6H); 3.60 and 3.75 (both m, together 2H); 4.15 and 4.40 (both m, together 1H); 6.80 and 7.00 (both d, together 1H); 7.45–7.80 (m, 5H). HPLC method B: elution at 4.16 min. MS: calc. for [M+H]+: 353; found: 353.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 58 (General Procedure (A))

(E)-3-(4-tert-Butylphenyl)-1-((S)-2-((pyrrolidin-1-yl)methyl)pyrrolidin-1-yl)propenone

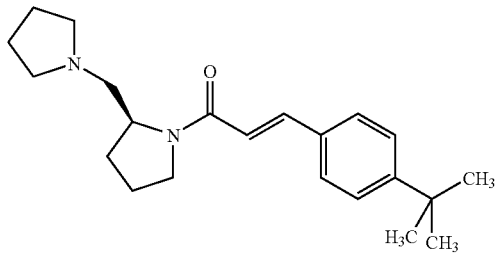

340 mg of the title compound were synthesized as described for (E)-3-(4-bromophenyl)-1-((S)-2-((pyrrolidin-1-yl)methyl)pyrrolidin-1-yl)propenone, using (E)-4-tert-butylcinnamic acid (commercially available at e.g. Emkachem) instead of (E)-4-bromocinnamic acid.

$^1$H-NMR (CDCl$_3$, 2 sets of signals) δ 1.40 (s, 9H); 1.75 (m, 4H); 1.85–2.20 (m, 4H); 2.40–2.75 (m, 6H); 3.60 and 3.70 (both m, together 2H); 4.15 and 4.40 (both m, together 1H); 6.70 and 6.85 (both d, together 1H); 7.40 (m, 2H); 7.50 (d, 2H); 7.70 (d, 1H). HPLC method B: elution at 4.76 min. MS: calc. for [M+H]+: 341; found: 341.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 59 (General Procedure (A))

(E)-1-((S)-2-((Pyrrolidin-1-yl)methyl)pyrrolidin-1-yl)-3-(3-(trifluoromethoxy)phenyl)propenone

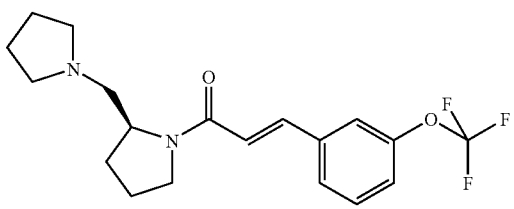

340 mg of the title compound were synthesized as described for (E)-3-(4-bromophenyl)-1-((S)-2-((pyrrolidin-1-yl)methyl)pyrrolidin-1-yl)propenone, using (E)-3-(trifluoromethoxy)cinnamic acid (commercially available at e.g. Lancaster) instead of (E)-4-bromocinnamic acid.

$^1$H-NMR (CDCl$_3$, 2 sets of signals) δ 1.80 (m, 4H); 1.85–2.20 (m, 4H); 2.40–2.80 (m, 6H); 3.65 and 3.70 (both m, together 2H); 4.15 and 4.40 (both m, together 1H); 6.75 and 6.90 (both d, together 1H); 7.20 (m, 1H); 7.40 (m, 2H); 7.65 (d, 1H). HPLC method B: elution at 4.30 min. MS: calc. for [M+H]+: 369; found: 369.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 60 (General Procedure (A))

(E)-3-(4-Chloro-3-trifluoromethylphenyl)-1-((S)-2-((pyrrolidin-1-yl)methyl)pyrrolidin-1-yl)propenone

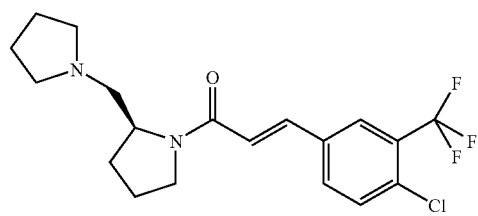

210 mg of the title compound were synthesized as described for (E)-3-(4-bromophenyl)-1-((S)-2-((pyrrolidin-1-yl)methyl)pyrrolidin-1-yl)propenone, using (E)-4-chloro-3-(trifluoromethyl)cinnamic acid (commercially available at e.g. Interchim, France) instead of (E)-4-bromocinnamic acid.

$^1$H-NMR (CDCl$_3$, 2 sets of signals) δ 1.75 (m, 4H); 1.85–2.20 (m, 4H); 2.40–2.75 (m, 6H); 3.60 and 3.70 (both m, together 2H); 4.15 and 4.40 (both m, together 1H); 6.75 and 6.95 (both d, together 1H); 74.5–7.60 (m, 2H); 7.65 (d, 1H); 7.85 (m, 1H). HPLC method B: elution at 4.50 min. MS: calc. for [M+H]+: 387; found: 387.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 61 (General Procedure (A))

(E)-3-(3-Fluoro-5-(trifluoromethyl)phenyl)-1-((S)-2-((pyrrolidin-1-yl)methyl)pyrrolidin-1-yl)propenone

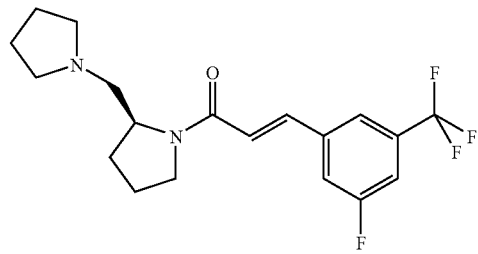

290 mg of the title compound were synthesized as described for (E)-3-(4-bromophenyl)-1-((S)-2-((pyrrolidin-1-yl)methyl)pyrrolidin-1-yl)propenone, using (E)-3-fluoro-5-(trifluoromethyl)cinnamic acid (commercially available at e.g. Interchim, France) instead of (E)-4-bromocinnamic acid.

¹H-NMR (CDCl₃, 2 sets of signals) δ 1.75 (m, 4H); 1.85–2.15 (m, 4H); 2.45–2.75 (m, 6H); 3.60 and 3.70 (both m, together 2H); 4.15 and 4.40 (both m, together 1H); 7.80 and 7.00 (both d, together 1H); 7.30 (d, 1H); 7.40 (d, 1H); 7.55 (m, 1H); 7.65 (dd, 1H). HPLC method B: elution at 4.29 min. MS: calc. for [M+H]⁺: 371; found: 371.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 62 (General Procedure (C))

(E)-1-((S)-2-(Diethylaminomethyl)pyrrolidin-1-yl)-3-(4-(trifluoromethoxy)phenyl)propenone

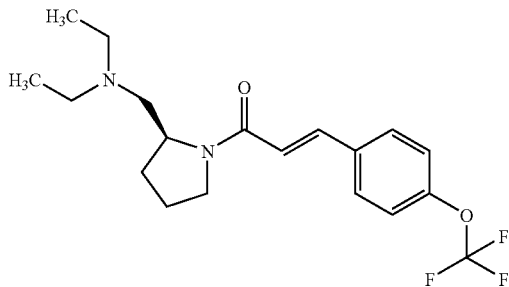

Step 1: N,N-Diethyl-N-(((S)-pyrrolidin-2-yl)methyl)amine

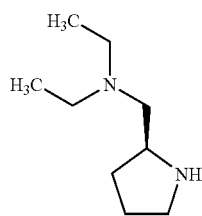

N,N-Diethyl-N-(((S)-pyrrolidin-2-yl)methyl)amine was synthesized as described for (S)-2-((pyrrolidin-1-yl)methyl)pyrrolidine starting with N,N-diethylamine instead of pyrrolidine.

¹H-NMR (CDCl₃) δ 1.00 (t, 6H); 1.35 (m, 1H); 1.75 (m, 2H); 1.85 (m, 1H); 2.35 (m, 2H); 2.55 (m, 4H); 2.85 (m, 1H); 3.00 (m, 1H); 3.20 (m, 1H).

Step 2

170 mg of the title compound were synthesized as described for (E)-3-(4-bromophenyl)-1-((S)-2-((pyrrolidin-1-yl)methyl)pyrrolidin-1-yl)propenone, using (E)-4-trifluoromethoxycinnamic acid instead of (E)-4-bromocinnamic acid and N,N-diethyl-N-(((S)-pyrrolidin-2-yl)methyl)amine instead of (S)-2-((pyrrolidin-1-yl)methyl)pyrrolidine.

¹H-NMR (CDCl₃, 2 sets of signals) δ 1.05 (m, 6H); 1.85–2.15 (m, 4H); 2.15–2.80 (m, 6H); 3.50–3.75 (m, 2H); 4.10 and 4.30 (both m, together 1H); 6.70 and 6.90 (both d, together 1H); 7.20 (d, 2H); 7.55 (d, 2H); 7.65 and 7.66 (both d, together 1H). HPLC method B: elution at 4.54 min. MS: calc. for [M+H]⁺: 371; found: 371.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 63 (General Procedure (C))

(E)-1-((S)-2-(Diethylaminomethyl)pyrrolidin-1-yl)-3-(4-(trifluoromethyl)phenyl)propenone

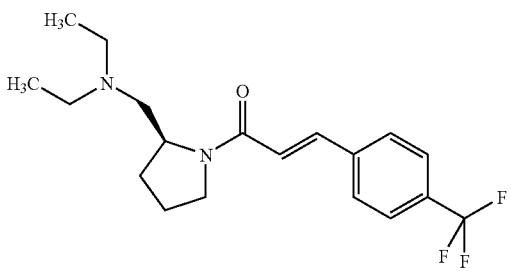

310 mg of the title compound were synthesized as described for (E)-3-(4-bromophenyl)-1-((S)-2-((pyrrolidin-1-yl)methyl)pyrrolidin-1-yl)propenone, using (E)-4-trifluoromethylcinnamic acid instead of (E)-4-bromocinnamic acid and N,N-diethyl-N-(((S)-pyrrolidin-2-yl)methyl)amine instead of (S)-2-((pyrrolidin-1-yl)methyl)pyrrolidine.

¹H-NMR (CDCl₃, 2 sets of signals) δ 1.00 (m, 6H); 1.85–2.15 (m, 4H); 2.20–2.80 (m, 6H); 3.60 and 3.70 (both m, together 2H); 4.10 and 4.30 (both m, together 1H); 6.80 and 7.00 (both d, together 1H); 7.60 (AB, 2H); 7.70 and 7.71 (both d, together 1H). HPLC method B: elution at 4.39 min. MS: calc. for [M+H]⁺: 355; found: 355.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 64 (General Procedure (C))

(E)-1-((S)-2-(Diethylaminomethyl)pyrrolidin-1-yl)-3-(3,4-dimethoxyphenyl)propenone

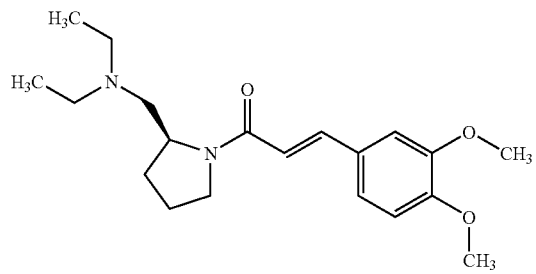

190 mg of the title compound were synthesized as described for (E)-3-(4-bromophenyl)-1-((S)-2-((pyrrolidin-1-yl)methyl)pyrrolidin-1-yl)propenone, using (E)-3,4-dimethoxycinnamic acid instead of (E)-4-bromocinnamic acid and N,N-diethyl-N-(((S)-pyrrolidin-2-yl)methyl)amine instead of (S)-2-((pyrrolidin-1-yl)methyl)pyrrolidine.

¹H-NMR (CDCl₃, 2 sets of signals) δ 1.05 (m, 6H); 1.85–2.15 (m, 4H); 2.15–2.80 (m, 6H); 3.60 and 3.75 (both m, together 2H); 3.90 (s, 6H); 4.10 and 4.35 (both m, together 1H); 6.60 and 6.75 (both d, together 1H); 6.85 (d, 1H); 7.03 and 7.05 (both s, together 1H); 7.10 (d, 1H); 7.65 and 7.66 (both d, together 1H). HPLC method B: elution at 3.47 min. MS: calc. for [M+H]+: 347; found: 347.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 65 (General Procedure (C))

(E)-1-((R)-2-((Piperidin-1-yl)methyl)pyrrolidin-1-yl)-3-(4-(trifluoromethoxy)phenyl)propenone

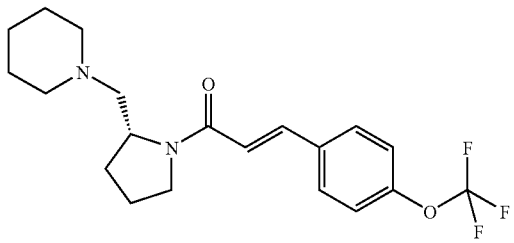

Step 1:

1-(((R)-Pyrrolidin-2-yl)methyl)piperidine

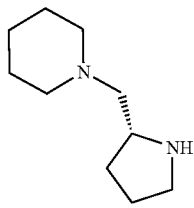

1-(((R)-Pyrrolidin-2-yl)methyl)piperidine was synthesized as described for (S)-2-((pyrrolidin-1-yl)methyl)pyrrolidine starting with (R)-1-(tert-butoxycarbonyl)pyrrolidine-1-carboxylic acid instead of (S)-1-(tert-butoxycarbonyl)pyrrolidine-1-carboxylic acid.

¹H-NMR (CDCl₃) δ 1.30 (m, 1H); 1.40 (m, 2H); 1.55 (m, 4H); 1.70 (m, 3H); 1.85 (m, 1H); 2.25–2.60 (m, 6H); 2.80 (m, 1H); 3.00 (m, 1H); 3.25 (m, 1H).

Step 2

185 mg of the title compound were synthesized as described for (E)-3-(4-bromophenyl)-1-((S)-2-((pyrrolidin-1-yl)methyl)pyrrolidin-1-yl)propenone, using (E)-4-trifluoromethoxycinnamic acid instead of (E)-4-bromocinnamic acid and 1-(((R)-pyrrolidin-2-yl)methyl)piperidine instead of (S)-2-((pyrrolidin-1-yl)methyl)pyrrolidine.

¹H-NMR (CDCl₃, 2 sets of signals) δ 1.45 (m, 2H); 1.60 (m, 4H); 1.80–2.10 (m, 4H); 2.15–2.70 (m, 6H); 3.50–3.75 (m, 2H); 4.15 and 4.40 (both m, together 1H); 6.70 and 6.90 (both d, together 1H); 7.20 (d, 2H); 7.55 (d, 2H); 7.65 (d, 1H). HPLC method B: elution at 4.61 min. MS: calc. for [M+H]+: 383; found: 383.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 66 (General Procedure (C))

(E)-1-((R)-2-((Piperidin-1-yl)methyl)pyrrolidin-1-yl)-3-(4-(trifluoromethyl)phenyl)propenone

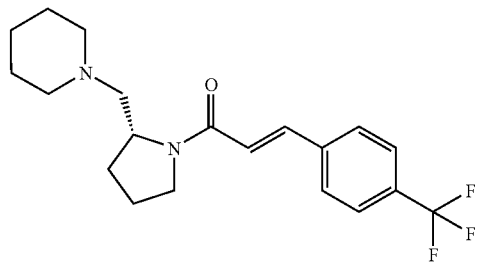

479 mg of the title compound were synthesized as described for (E)-3-(4-bromophenyl)-1-((S)-2-((pyrrolidin-1-yl)methyl)pyrrolidin-1-yl)propenone, using (E)-4-trifluoromethylcinnamic acid instead of (E)-4-bromocinnamic acid and 1-(((R)-pyrrolidin-2-yl)methyl)piperidine instead of (S)-2-((pyrrolidin-1-yl)methyl)pyrrolidine.

¹H-NMR (CDCl₃, 2 sets of signals) δ 1.45 (m, 2H); 1.55 (m, 4H); 1.85–2.10 (m, 4H); 2.15–2.70 (m, 6H); 3.50–3.75 (m, 2H); 4.15 and 4.40 (both m, together 1H); 6.80 and 7.05 (both d, together 1H); 7.65 (AB, 4H); 7.70 (d, 1H). HPLC method B: elution at 4.44 min. MS: calc. for [M+H]+: 367; found: 367.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 67 (General Procedure (D))

((S)-2-((Piperidin-1-yl)methyl)pyrrolidin-1-yl)-(5-(trifluoromethyl)benzofuran-2-yl)methanone

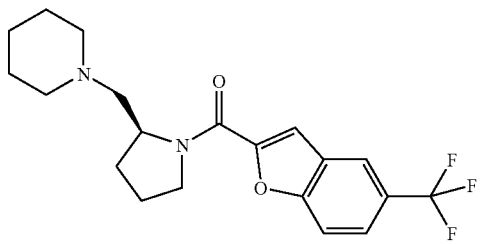

Step 1: 2-(4-(Trifluoromethyl)phenoxy)tetrahydropyran

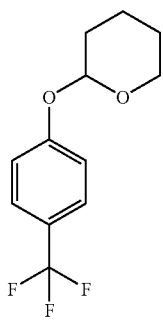

a solution of 4-(trifluoromethyl)phenol (2.44 g, 15 mmol) in dichloromethane (5 ml) was added to a solution of 3,4-dihydro-2H-pyran (4.10 ml, 45 mmol) and a 3.6 M solution of hydrogen chloride in ethyl acetate (0.015 ml, 0.05 mmol) in dichloromethane (10 ml). The reaction mixture was stirred at room temperature for 16 h. It was diluted with ethyl acetate (100 m) and washed with a saturated aqueous solution of sodium hydrogencarbonate (100 ml). The aqueous phase was extracted with ethyl acetate (2×30 ml). The combined organic layers were dried over magnesium sulphate. The solvent was removed in vacuo. The crud product was purified by flash chromatography on silica (90 g), using ethyl acetate/heptane 1:10 as eluent to give 3.09 g of 2-(4-(trifluoromethyl)phenoxy)tetrahydropyran.

$^1$H-NMR (CDCl$_3$) δ 1.65 (m, 3H); 1.85 (m, 2H); 2.00 (m, 1H); 3.60 (m, 1H); 3.85 (m, 1H); 5.45 (t, 1H); 7.15 (d, 2H); 7.55 (d, 2H).

Step 2: 2-Hydroxy-5-(trifluoromethyl)benzaldehyde

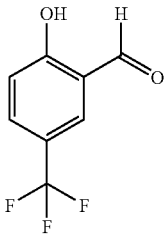

At −15° C., an 1.6 N solution of n-butyllithium in hexanes (7.20 ml, 11.5 mmol) was added to N,N,N',N'-tetramethylethylenediamine (1.72 ml, 11.4 mmol). The reaction mixture was stirred for 10 min at −10° C. 2-(4-(trifluoromethyl)phenoxy)tetrahydropyran (2.0 g, 8.12 mmol) was added. The reaction mixture was stirred for 2 h at −10° C. N,N-Dimethylformamide (0.88 ml, 11.4 mmol) was added. The reaction mixture was stirred for 15 min at −10° C. It was given onto a 6 M hydrochloric acid. This mixture was stirred at room temperature for 16 h. The organic layer was isolated and dried. The solvent was removed in vacuo. 659 mg of 2-hydroxy-5-(trifluoromethyl)benzaldehyde were isolated from the crude mixture by flash chromatography on silica (90 g), using ethyl acetate/heptane 1:10 as eluent.

$^1$H-NMR (CDCl$_3$) δ 7.10 (d, 1H); 7.80 (d, 1H); 7.90 (s, 1H); 9.90 (s, 1H); 11.30 (s, 1H).

Step 3: 5-(Trifluoromethyl)benzofuran-2-carboxylic Acid Ethyl Ester

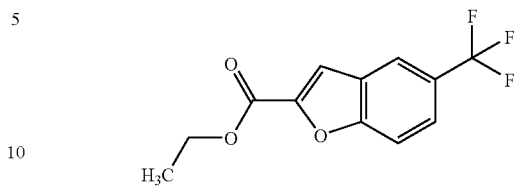

A mixture of potassium carbonate (4.00 g, 8.6 mmol) diethyl bromomalonate (1.43 ml, 8.4 mmol), 2-hydroxy-5-(trifluoromethyl)benzaldehyde (638 mg, 3.40 mmol) and methyl ethyl ketone (15 ml) was heated to reflux for 16 h. It was cooled to room temperature. The solid was filtered off and washed with acetone. The solvent was removed from the filtrate. The crude product was purified by flash chromatography on silica (40 g), using ethyl acetate/heptane 1:5 as eluent, to give 747 mg of 5-(trifluoromethyl)benzofuran-2-carboxylic acid ethyl ester.

$^1$H-NMR (CDCl$_3$) δ 1.45 (t, 3H); 4.50 (q, 2H); 7.60 (s, 1H); 7.70 (s, 2H); 8.00 (s, 1H).

Step 4: 5-(Trifluoromethyl)benzofuran-2-carboxylic Acid

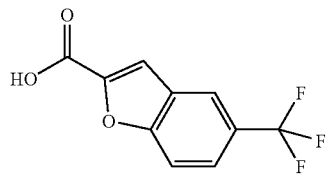

A solution of lithium hydroxide (78 mg, 3.7 mmol) in water (6 ml) was added to a solution of 5-(trifluoromethyl)benzofuran-2-carboxylic acid ethyl ester (705 mg, 2.73 mmol) in 1,4-dioxane (6 ml). 1,4-Dioxane was added until a clear solution was obtained. The reaction mixture was stirred for 16 h at room temperature. It was diluted with an 1 N aqueous solution of sodium hydroxide and washed with tert-butyl methyl ether (2×30 ml). The aqueous solution was acidified with a 10% aqueous solution of sodium hydrogen sulphate until pH 3 was obtained. It was extracted with ethyl acetate (3×40 ml). The combined ethyl acetate layers were dried over magnesium sulphate. The solvent was removed in vacuo to give crude 5-(trifluoromethyl)benzofuran-2-carboxylic acid which was used in the next step without further purification.

$^1$H-NMR (DMSO-d$_6$) δ 7.80 (s, 1H); 7.85 (d, 1H); 7.95 (d, 1H); 8.25 (s, 1H); 13.80 (br, 1H).

180 mg of the title compound were synthesized as described for (E)-3-(4-bromophenyl)-1-((S)-2-((pyrrolidin-1-yl)methyl)pyrrolidin-1-yl)propenone, using 5-(trifluoromethyl)benzofuran-2-carboxylic acid instead of (E)-4-bromocinnamic acid and 1-(((S)-pyrrolidin-2-yl)methyl)piperidine instead of (S)-2-((pyrrolidin-1-yl)methyl)pyrrolidine.

$^1$H-NMR (CDCl$_3$) δ 1.40–1.80 (br, 6H); 2.00 (br, 2H); 2.30 (br, 2H); 2.55 (br, 2H); 3.60–4.10 (br, 2H); 4.50 and 4.85 (both br, together 1H); 7.35–7.70 (br, 3H); 8.00 (s, 1H). HPLC method A: elution at 9.55 min. MS: calc. for [M+H]$^+$: 381; found: 381.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 68 (General Procedure (E))

(E)-3-(4-(Cyclopropanecarbonyl)phenyl)-1-((S)-2-((pyrrolidin-1-yl)methyl)pyrrolidin-1-yl)propenone

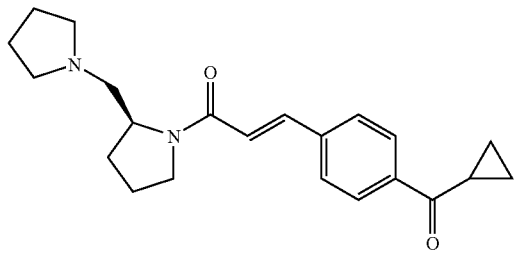

Step 1
(E)-3-(4-(Cyclopropanecarbonyl)phenyl)acrylic Acid Methyl Ester

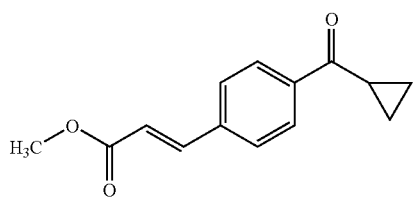

A mixture of (4-bromophenyl)-(cyclopropyl)methanone (0.450 g, 2.00 mmol), palladium acetate 49 mg, 0.220 mmol), triphenylphosphine (55 mg, 0.21 mmol), methyl acrylate (0.43 g, 2.50 mmol) and triethylamine (10 ml, 72 mmol) was heated to 100° C. for 48 in a closed reaction vial. The reaction mixture was cooled to room temperature. The solid was removed by filtration. A mixture of ice and 1 N hydrochloric acid was added to the liquid. The mixture was stirred for 1 h at room temperature. It was extracted with ethyl acetate (2×150 ml). The combined organic layers were washed with a saturated aqueous solution of sodium hydrogencarbonate (100 ml) and dried over magnesium sulphate. The solvent was removed in vacuo. The crude product was purified by flash chromatography on silica (40 g) using a mixture of dichloromethane/ethyl acetate/heptane (1:1:1) as eluent, to give 217 mg of (E)-3-(4-(cyclopropanecarbonyl)phenyl)acrylic acid methyl ester.

$^1$H-NMR (CDCl$_3$) δ 1.05 (m, 2H); 1.25 (m, 2H); 2.65 (m, 1H); 3.85 (s, 3H); 6.55 (d, 1H); 7.62 (d, 2H); 7.75 (d, 1H); 8.05 (d, 2H).

Step 2:
(E)-3-(4-(Cyclopropanecarbonyl)phenyl)acrylic Acid

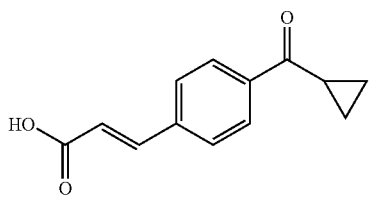

A solution of lithium hydroxide (27 mg, 1.1 mmol) in water (2.00 ml) was added to a solution of (E)-3-(4-(cyclopropanecarbonyl)phenyl)acrylic acid methyl ester (217 mg, 0.94 mmol) in 1,4-dioxane (2.00 ml). 1,4-Dioxane was added until a clear solution was obtained. The reaction mixture was stirred for 16 h at room temperature. It was diluted with an 1 N aqueous solution of sodium hydroxide (50 ml) and washed with tert-butyl methyl ether (2×40 ml). The aqueous solution was acidified with a 10% aqueous solution of sodium hydrogensulphate until pH 3 was obtained. It was extracted with ethyl acetate (3×100 ml) The combined organic layers were dried over magnesium sulphate. The solvent was removed in vacuo to give 170 mg of crude (E)-3-(4-(cyclopropanecarbonyl)phenyl)acrylic acid which was used in the next step without further purification.

$^1$H-NMR (DMSO-d$_6$) δ 1.05 (m, 4H); 2.95 (m, 1H); 6.70 (d, 1H); 7.65 (d, 1H); 7.85 (d, 2H); 8.05 (d, 2H); 12.60 (br, 1H).

Step 3

130 mg of the title compound were synthesized as described for (E)-3-(4-bromophenyl)-1-((S)-2-((pyrrolidin-1-yl)methyl)pyrrolidin-1-yl)propenone, using (E)-3-(4-(cyclopropanecarbonyl)phenyl)acrylic acid instead of (E)-4-bromocinnamic acid.

$^1$H-NMR (CDCl$_3$, two sets of signals, broad signals) δ 1.05 (m, 2H); 1.25 (m, 2H); 1.80 (m, 4 H); 1.90–2.15 (m, 4H); 2.40–2.80 (m, 6H); 3.60 and 3.70 (both m, together 2H); 4.15 and 4.40 (both m, together 1H); 6.85 and 7.00 (both d, together 1H); 7.40 (d, 2H); 7.75 (d, 1H); 8.00 (m, 2H). HPLC method A: elution at 8.48 min. MS: calc. for [M+H]$^+$: 353; found: 353.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 69 (General Procedure (D))

((S)-2-((Pyrrolidin-1-yl)methyl)pyrrolidin-1-yl)-(5-(trifluoromethoxy)benzofuran-2-yl)methanone

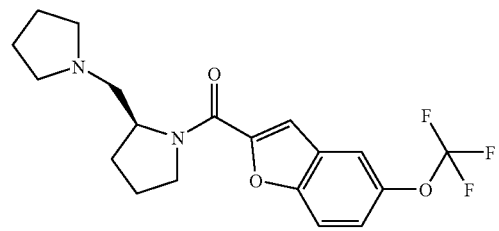

Step 1:
5-(Trifluoromethoxy)benzofuran-2-carboxylic Acid

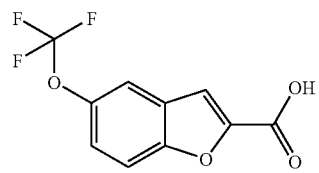

93 mg of 5-(trifluoromethoxy)benzofuran-2-carboxylic acid were prepared as described for 5-(trifluoromethyl)

benzofuran-2-carboxylic acid, using 4-(trifluoromethoxy)phenol instead of 4-(trifluoromethyl)phenol.

¹H-NMR (DMSO-d₆) δ 7.50 (d, 1H); 7.70 (s, 1H); 7.85 (m, 2H); 13.80 (br, 1H).

69 mg of the title compound were synthesized as described for (E)-3-(4-bromophenyl)-1-((S)-2-((pyrrolidin-1-yl)methyl)pyrrolidin-1-yl)propenone, using 5-(trifluoromethoxy)benzofuran-2-carboxylic acid instead of (E)-4-bromocinnamic acid.

¹H-NMR (CDCl₃, two sets of signals, broad signals) δ 1.75 (m, 5H); 1.90–2.30 (m, 5H); 2.30–2.90 (m, 6H); 3.60–4.10 (m, 2H); 4.50 and 4.85 (both m, together 1H); 7.30 (m, 1H); 7.35–7.60 (m, 2H). HPLC method A: elution at 9.51 min. MS: calc. for [M+H]⁺: 383; found: 383.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 70 (General Procedure (D))

((S)-2-((Diethylamino)methyl)pyrrolidin-1-yl)-(6-(trifluoromethyl)benzofuran-2-yl)methanone

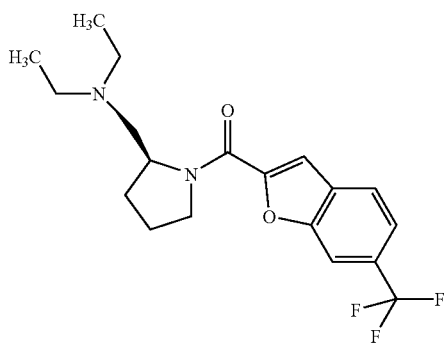

Step 1: 6-(Trifluoromethyl)benzofuran-2-carboxylic Acid

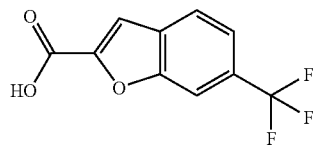

93 mg of 6-(trifluoromethyl)benzofuran-2-carboxylic acid were prepared as described for 5-(trifluoromethyl)benzofuran-2-carboxylic acid, using 3-(trifluoromethyl)phenol instead of 4-(trifluoromethyl)phenol.

¹H-NMR (DMSO-d₆) δ 7.70 (d, 1H); 7.80 (s, 1H); 8.05 (d, 1H); 8.20 (s, 1H); 13.90 (br, 1H).

220 mg of the title compound were synthesized as described for (E)-3-(4-bromophenyl)-1-((S)-2-((pyrrolidin-1-yl)methyl)pyrrolidin-1-yl)propenone, using 6-(trifluoromethyl)benzofuran-2-carboxylic acid instead of (E)-4-bromocinnamic acid and N,N-diethyl-N-(((S)-pyrrolidin-2-yl)methyl)amine instead of (S)-2-((pyrrolidin-1-yl)methyl)pyrrolidine.

¹H-NMR (CDCl₃, two sets of signals) δ 0.90 and 1.05 (both m, together 6H); 1.90–2.15 (m, 4 H); 2.20–2.90 (m, 6H); 3.75, 3.90, and 4.05 (all m, together 2H); 4.50 and 4.85 (both m, together 1H); 7.40–7.60 (m, 2H); 7.70–7.85 (m, 2H). HPLC method A: elution at 10.18 min. MS: calc. for [M+H]⁺: 369; found: 369.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 71 (General Procedure (D))

((S)-2-((Piperidin-1-yl)methyl)pyrrolidin-1-yl)-(6-(trifluoromethyl)benzofuran-2-yl)methanone

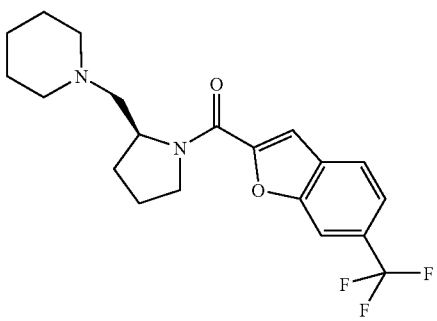

71 mg of the title compound were synthesized as described for (E)-3-(4-bromophenyl)-1-((S)-2-((pyrrolidin-1-yl)methyl)pyrrolidin-1-yl)propenone, using 6-(trifluoromethyl)benzofuran-2-carboxylic acid instead of (E)-4-bromocinnamic acid and 1-(((S)-pyrrolidin-2-yl)methyl)piperidine instead of (S)-2-((pyrrolidin-1-yl)methyl)pyrrolidine.

¹H-NMR (CDCl₃, two sets of signals) δ 1.20–1.70 (m, 6H); 1.90–2.20 (m, 4H); 2.20–2.85 (m, 6H); 3.60–3.95 and 3.95–4.15 (both m, together 2H); 4.55 and 4.85 (both m, together 1H); 7.40–7.60 (m, 2H); 7.65–7.90 (m, 2H). HPLC method A: elution at 9.74 min. MS: calc. for [M+H]⁺: 381; found: 381.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 72 (General Procedure (D))

((S)-2-((Pyrrolidin-1-yl)methyl)pyrrolidin-1-yl)-(6-(trifluoromethyl)benzofuran-2-yl)methanone

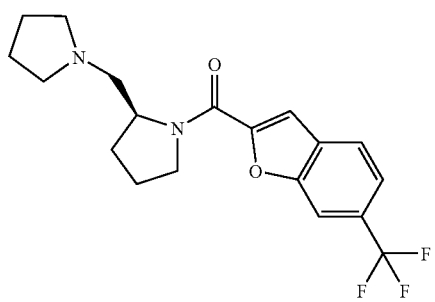

150 mg of the title compound were synthesized as described for (E)-3-(4-bromophenyl)-1-((S)-2-((pyrrolidin- 1-yl)methyl)pyrrolidin-1-yl)propenone, using 6-(trifluoromethyl)benzofuran-2-carboxylic acid instead of (E)-4-bromocinnamic acid.

$^1$H-NMR (CDCl$_3$, two sets of signals) δ 1.70 (m, 4H); 1.90–2.20 (m, 4H); 2.20–2.90 (m, 6H); 3.60–4.10 (m, 2H); 4.55 and 4.85 (both m, together 1H); 7.40–7.60 (m, 2H); 7.70–7.90 (m, 2H). HPLC method A: elution at 9.39 min. MS: calc. for [M+H]$^+$: 367; found: 367.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 73 (General Procedure (C))

(E)-3-(4-Chloro-3-trifluoromethylphenyl)-1-((S)-2-((piperidin-1-yl)methyl)pyrrolidin-1-yl)propenone

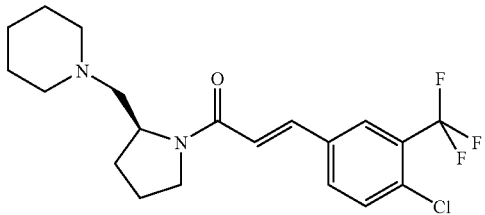

220 mg of the title compound were synthesized as described for (E)-3-(4-bromophenyl)-1-((S)-2-((pyrrolidin-1-yl)methyl)pyrrolidin-1-yl)propenone, using (E)-4-chloro-3-(trifluoromethyl)cinnamic acid instead of (E)-4-bromocinnamic acid and 1-(((S)-pyrrolidin-2-yl)methyl)piperidine instead of (S)-2-((pyrrolidin-1-yl)methyl)pyrrolidine.

$^1$H-NMR (CDCl$_3$, two sets of signals) δ 1.30–1.70 (m, 6H); 1.80–2.15 (m, 4H); 2.15–2.75 (m, 6H); 3.60 and 3.70 (both m, together 2H); 4.15 and 4.40 (both m, together 1H); 6.75 and 7.00 (both d, together 1H); 7.45–7.70 (m, 3H); 7.80 and 7.85 (both s, together 1H). HPLC method A: elution at 10.41 min. MS: calc. for [M+H]$^+$: 401; found: 401.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 74 (General Procedure (C))

(E)-3-(3-Fluoro-5-(trifluoromethyl)phenyl)-1-((S)-2-((piperidin-1-yl)methyl)pyrrolidin-1-yl)propenone

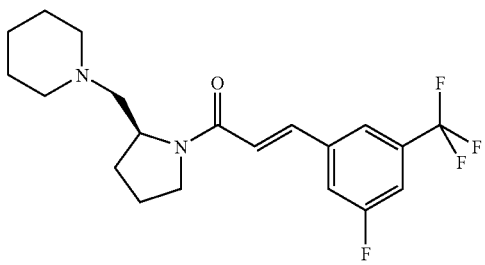

210 mg of the title compound were synthesized as described for (E)-3-(4-bromophenyl)-1-((S)-2-((pyrrolidin-1-yl)methyl)pyrrolidin-1-yl)propenone, using (E)-3-fluoro-5-(trifluormethyl)cinnamic acid instead of (E)-4-bromocinnamic acid and 1-(((S)-pyrrolidin-2-yl)methyl)piperidine instead of (S)-2-((pyrrolidin-1-yl)methyl)pyrrolidine.

$^1$H-NMR (CDCl$_3$, two sets of signals) δ 1.25–1.70 (m, 6H); 1.80–2.15 (m, 4H); 2.15–2.70 (m, 6H); 3.60 and 3.70 (both m, together 2H); 4.15 and 4.40 (both m, together 1H); 6.75 and 7.05 (both d, together 1H); 7.20–7.45 (m, 2H); 7.45–7.70 (m, 2H). HPLC method A: elution at 9.74 min. MS: calc. for [M+H]$^+$: 385; found: 385.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 75 (General Procedure (D))

((S)-2-((Pyrrolidin-1-yl)methyl)pyrrolidin-1-yl)-(5-(trifluoromethyl)benzofuran-2-yl)methanone

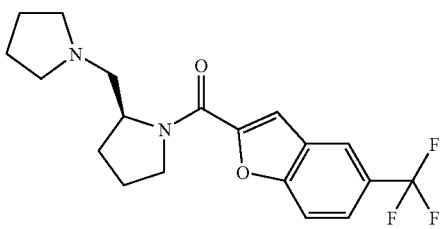

210 mg of the title compound were synthesized as described for (E)-3-(4-bromophenyl)-1-((S)-2-((pyrrolidin-1-yl)methyl)pyrrolidin-1-yl)propenone, using 5-(trifluoromethyl)benzofuran-2-carboxylic acid instead of (E)-4-bromocinnamic acid.

$^1$H-NMR (CDCl$_3$, two sets of signals) δ 1. HPLC method A: elution at MS: calc. for [M+H]$^+$:

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 76 (General Procedure (D))

((S)-2-(Diethylaminomethyl)pyrrolidin-1-yl)-(5-(trifluoromethyl)benzofuran-2-yl)methanone

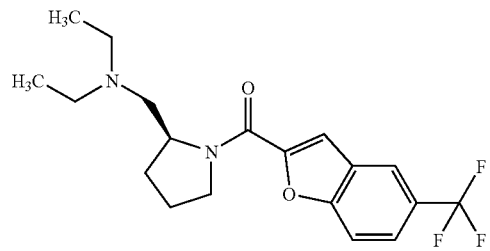

110 mg of the title compound were synthesized as described for (E)-3-(4-bromophenyl)-1-((S)-2-((pyrrolidin-1-yl)methyl)pyrrolidin-1-yl)propenone, using 5-(trifluoromethyl)benzofuran-2-carboxylic acid instead of (E)-4-bromocinnamic acid and N,N-diethyl-N-(((S)-pyrrolidin-2-yl)methyl)amine instead of (S)-2-((pyrrolidin-1-yl)methyl)pyrrolidine.

¹H-NMR (CDCl₃, two sets of signals, broad signals) δ 0.80–1.20 (m, 6H); 1.65 and 2.00 (both m, together 4H); 2.20–2.90 (m, 6H); 3.75, 3.90, and 4.05 (all m, together 2H); 4.45 and 4.80 (both m, together 1H); 7.40–7.70 (m, 3H); 8.00 (s, 1H). HPLC method A: elution at 9.31 min. MS: calc. for [M+H]⁺: 369; found: 369.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 77 (General Procedure (A))

(E)-1-(((S)-2-((Pyrrolidin-1-yl)methyl)pyrrolidin-1-yl)-3-(4-(trifluoromethyl)phenyl)but-2-en-1-one

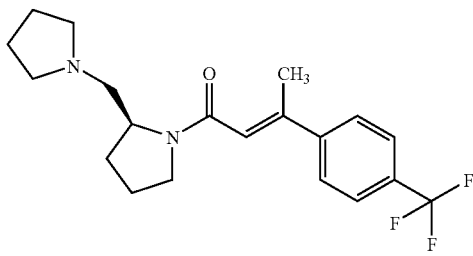

Step 1:
(E)-3-(4-(Trifluoromethyl)phenyl)but-2-enoic Acid

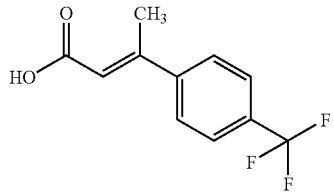

2.85 g of (E)-3-(4-(trifluoromethyl)phenyl)but-2-enoic acid were prepared as described for (E)-4-methylsulfonylcinnamic acid, using 1-(4-(trifluoromethyl)phenyl)ethanone instead of 4-(methylsulfonyl)benzaldehyde.

¹H-NMR (DMSO-d₆) δ 2.50 (s, 3H); 6.20 (s, 1H); 7.80 (s, 4H).

Step 2

240 mg of the title compound were synthesized as described for (E)-3-(4-bromophenyl)-1-((S)-2-((pyrrolidin-1-yl)methyl)pyrrolidin-1-yl)propenone, using (E)-3-(4-(trifluoromethyl)phenyl)but-2-enoic acid instead of (E)-4-bromocinnamic acid.

¹H-NMR (CDCl₃, two sets of signals, broad signals) δ 1.65–1.85 (m, 4H); 1.85–2.15 (m, 4H); 2.35–2.80 (m, 6H); 2.50 (s, 3H); 3.40–3.70 (m, 2H); 4.05 and 4.40 (both m, together 1H); 6.25 and 6.50 (both s, together 1H); 7.55 (m, 2H); 7.65 (d, 2H). HPLC method A: elution at 10.43 min. MS: calc. for [M+H]⁺: 367; found: 367.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 78 (General Procedure (A))

(E)-1-((S)-2-((Piperidin-1-yl)methyl)pyrrolidin-1-yl)-3-(4-(trifluoromethyl)phenyl)but-2-en-1-one

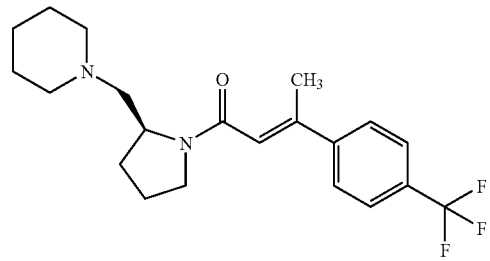

110 mg of the title compound were synthesized as described for (E)-3-(4-bromophenyl)-1-((S)-2-((pyrrolidin-1-yl)methyl)pyrrolidin-1-yl)propenone, using (E)-3-(4-(trifluoromethyl)phenyl)but-2-enoic acid instead of (E)-4-bromocinnamic acid and 1-(((S)-pyrrolidin-2-yl)methyl)piperidine instead of (S)-2-((pyrrolidin-1-yl)methyl)pyrrolidine.

¹H-NMR (CDCl₃, two sets of signals, broad signals) δ 1.30–1.65 (m, 6H); 2.80–2.10 (m, 4H); 2.15–2.70 (m, 6H); 2.45 (s, 3H); 3.40–3.70 (m, 2H); 4.00 and 4.35 (both m, together 1H); 6.25 and 6.50 (both s, together 1H); 7.50–7.65 (m, 4H). HPLC method A: elution at 10.69 min. MS: calc. for [M+H]⁺: 381; found: 381.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 79 (General Procedure (A))

(E)-3-(4-(Isobutyl)phenyl)-1-((S)-2-((pyrrolidin-1-yl)methyl)pyrrolidin-1-yl)but-2-en-1-one

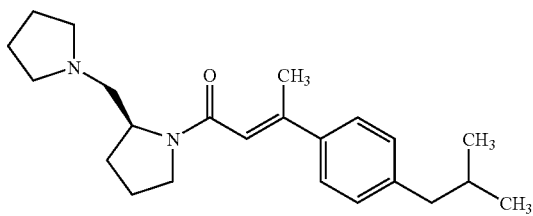

Step 1:
(E)-3-(4-(Isobutyl)phenyl)but-2-enoic Acid

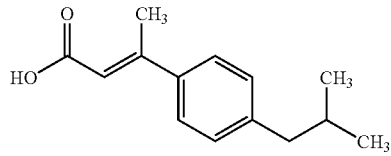

0.91 g of (E)-3-(4-(isobutyl)phenyl)but-2-enoic acid were prepared as described for (E)-4-methylsulfonylcinnamic acid, using 1-(4-(isopropyl)phenyl)ethanone instead of 4-(methylsulfonyl)benzaldehyde.

¹H-NMR (DMSO-d₆) δ 0.90 (d, 6H); 1.85 (m, 1H); 2.50 (m, 5H); 6.10 (s, 1H); 7.20 (d, 2H); 7.45 (d, 2H); 12.15 (br, 1H).

Step 2

250 mg of the title compound were synthesized as described for (E)-3-(4-bromophenyl)-1-((S)-2-((pyrrolidin-1-yl)methyl)pyrrolidin-1-yl)propenone, using (E)-3-(4-(isobutyl)phenyl)but-2-enoic acid instead of (E)-4-bromo-cinnamic acid.

$^1$H-NMR (CDCl$_3$, two sets of signals, broad signals) δ 0.95 (d, 6H); 1.65–1.80 (m, 4H); 1.80–2.15 (m, 5H); 2.40–2.80 (m, 6H); 2.45 (s, 3H); 2.50 (d, 2H); 3.45–3.60 (m, 2H); 4.05 and 4.40 (both m, together 1H); 6.25 and 6.45 (both s, together 1H); 7.15 (d, 2H); 7.40 (m, 2H). HPLC method A: elution at 11.19 min. MS: calc. for [M+H]$^+$: 355; found: 355.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 80 (General Procedure (A))

(E)-3-(4-(Isobutyl)phenyl)-1-((S)-2-((piperidin-1-yl)methyl)pyrrolidin-1-yl)but-2-en-1-one

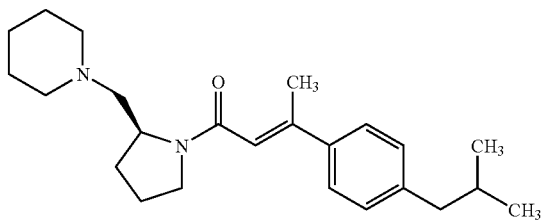

130 mg of the title compound were synthesized as described for (E)-3-(4-bromophenyl)-1-((S)-2-((pyrrolidin-1-yl)methyl)pyrrolidin-1-yl)propenone, using (E)-3-(4-(Isobutyl)phenyl)but-2-enoic acid instead of (E)-4-bromo-cinnamic acid and 1-(((S)-pyrrolidin-2-yl)methyl)piperidine instead of (S)-2-((pyrrolidin-1-yl)methyl)pyrrolidine.

$^1$H-NMR (CDCl$_3$, two sets of signals, broad signals) δ 0.90 (d, 6H); 1.30–1.65 (m, 6H); 1.70–2.10 (m, 5H); 2.10–2.70 (m, 6H); 2.45 (s, 3H); 2.50 (d, 2H); 3.35–3.65 (m, 2H); 4.05 and 4.40 (both m, together 1H); 6.25 and 6.45 (both s, together 1H); 7.15 (d, 2H); 7.35 and 7.45 (both d, together 2H). HPLC method A: elution at 11.63 min. MS: calc. for [M+H]$^+$: 369; found: 369.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 81 (General Procedure (A))

(E)-1-((S)-2-((Pyrrolidin-1-yl)methyl)pyrrolidin-1-yl)-3-(4-(1,2,4-triazol-1-yl)phenyl)propenone

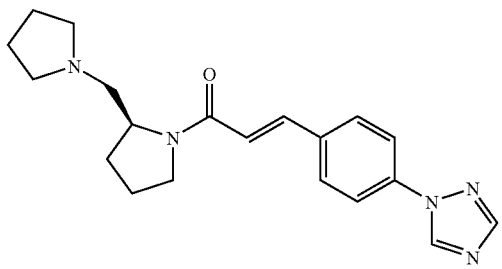

Step 1:

(E)-3-(4-(1,2,4-Triazol-1-yl)phenyl)acrylic Acid

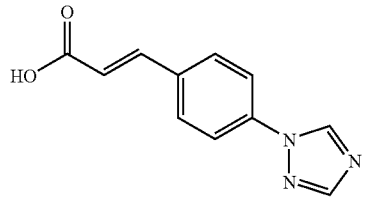

1.9 g of (E)-3-(4-(1,2,4-triazol-1-yl)phenyl)acrylic acid were prepared as described for (E)-3-(4-(methanesulfonyloxy)phenyl)acrylic acid, using 4-(1,2,4-triazol-1-yl)benzaldehyde instead of methanesulfonic acid 4-formylphenyl ester.

$^1$H-NMR (DMSO-d$_6$) δ 6.60 (d, 1H); 7.65 (d, 1H); 7.90 (AB, 4H); 8.30 (s, 1H); 9.40 (s, 1H); 12.50 (br, 1H).

Step 2

74 mg of the title compound were synthesized as described for (E)-3-(4-bromophenyl)-1-((S)-2-((pyrrolidin-1-yl)methyl)pyrrolidin-1-yl)propenone, using (E)-3-(4-(1,2,4-triazol-1-yl)phenyl)acrylic acid instead of (E)-4-bromo-cinnamic acid.

$^1$H-NMR (CDCl$_3$, two sets of signals) δ 1.80 (m, 4H); 1.85–2.20 (m, 4H); 2.45–2.80 (m, 6H); 3.60 and 3.70 (both m, together 2H); 4.20 and 4.40 (both m, together 1H); 6.80 and 6.95 (both m, together 1H); 7.70 (m, 5H); 8.10 (s, 1H); 8.60 (s, 1H). HPLC method A: elution at 2.96 min.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

Example 82 (General Procedure (A))

(E)-1-((S)-2-((Piperidin-1-yl)methyl)pyrrolidin-1-yl)-3-(4-(1,2,4-triazol-1-yl)phenyl)propenone

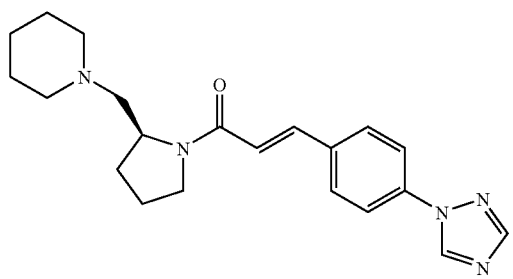

165 mg of the title compound were synthesized as described for (E)-3-(4-bromophenyl)-1-((S)-2-((pyrrolidin-1-yl)methyl)pyrroidin-1-yl)propenone, using (E)-3-(4-(1,2,4-triazol-1-yl)phenyl)acrylic acid instead of (E)-4-bromo-cinnamic acid and and 1-(((S)-pyrrolidin-2-yl)methyl)piperidine instead of (S)-2-((pyrrolidin-1-yl)methyl)pyrrolidine.

$^1$H-NMR (CDCl$_3$, two sets of signals) δ 1.40 (m, 2H); 1.55 (m, 4H); 1.80–2.15 (m, 4H); 2.15–2.70 (m, 6H); 3.60 and 3.70 (both m, together 2H); 4.20 and 4.40 (both m, together 1H); 6.75 and 7.00 (both d, together 1H); 7.70 (m, 5H); 8.10 (s, 1H); 8.60 (s, 1H). HPLC method A: elution at 3.15 min.

The title compound was transferred into its hydrochloride salt, by dissolving it in ethyl acetate (5 ml). A 3.2 M solution of hydrogen chloride in ethyl acetate (5 ml) was added. The solvent was removed in vacuo. The residue was dissolved in ethanol (50 ml). The solvent was removed in vacuo.

The ability of the compounds to interact with the histamine H3 receptor can be determined by the following in vitro binding assays.

Binding Assay I

Rat cerebral cortex is homogenized in ice cold K-Hepes, 5 mM $MgCl_2$ pH 7.1 buffer. After two differential centrifugations the last pellet is resuspended in fresh Hepes buffer containing 1 mg/ml bacitracin. Aliquots of the membrane suspension (400 μg/ml) are incubated for 60 min at 25° C. with 30 pM [$^{125}$I]-iodoproxifan, a known histamine H3 receptor antagonist, and the test compound at various concentrations. The incubation is stopped by dilution with ice-cold medium, followed by rapid filtration through Whatman GF/B filters pretreated for 1 hour with 0.5% polyethyleneimine. The radioactivity retained on the filters is counted using a Cobra II auto gamma counter. The radioactivity of the filters is indirectly proportional to the binding affinity of the tested compound. The results are analyzed by nonlinear regression analysis.

Binding Assay II

The H3-receptor agonist ligand R-α-methyl[$^3$H]histamine (RAMHA) is incubated with isolated rat cortex cell-membranes at 25° C. for 1 hour, followed by a filtration of the incubate through Whatman GF/B filters. Radioactivity retained on the filters is measured using a beta counter. Male Wistar rats (150–200 g) are decapitated and cerebral cortex is quickly dissected out and frozen immediately on dry ice. Tissue is kept at −80° C. until membrane preparation. During the membrane preparation the tissue is kept on ice all the time. Rat cerebral cortex is homogenized in 10 volumes (w/w) ice-cold Hepes buffer (20 mM Hepes, 5 mM $MgCl_2$ pH 7.1 (KOH)+1 mg/ml bacitracin) using an Ultra-Turrax homogenizer for 30 seconds. The homogenate is centrifuged at 140 g in 10 min. The supernatant is transferred to a new test tube and centrifuged for 30 min at 23 000 g. Pellet is resuspended in 5–10 ml Hepes buffer, homogenized and centrifuged for 10 min at 23 000 g. This short centrifugation step is repeated twice. After the last centrifugation the pellet is resuspended in 2–4 ml Hepes buffer and the protein concentration is determined. The membranes are diluted to a protein concentration of 5 mg/ml using Hepes buffer, aliquoted and stored at −80° C. until use.

50 μl test-compound, 100 μl membrane (200 μg/ml), 300 μl Hepes buffer and 50 μl R-α-methyl[$^3$H]histamine (1 nM) are mixed in a test tube. The compounds to be tested are dissolved in DMSO and further diluted in $H_2O$ to the desired concentrations. Radioligand and membranes are diluted in Hepes buffer+1 mg/ml bacitracin. The mixture is incubated for 60 min at 25° C. Incubation is terminated by adding 5 ml ice-cold 0.9% NaCl, followed by rapid filtration through Whatman GF/B filters pre-treated for 1 hour with 0.5% polyethyleneimine. The filters are washed with 2×5 ml ice-cold NaCl. To each filter a 3 ml scintillation cocktail is added and the radioactivity retained is measured with a Packard Tri-Carb beta counter. $IC_{50}$ values are calculated by non-linear regression analysis of binding curves (6 points minimum) using the windows program GraphPad Prism, GraphPad software, USA.

Binding Assay III

The human H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM (GIBCO-BRL) with glutamax, 10% foetal calf serum, 1% penicillin/streptavidin and 1 mg/ml G 418 at 37° C. and 5% $CO_2$. Before harvesting, the confluent cells are rinsed with PBS and incubated with Versene (proteinase, GIBCO-BRL) for approximately 5 min. The cells are flushed with PBS and DMEM and the cell suspension collected in a tube and centrifuged for 5–10 min at 1500 rpm in a Heraeus Sepatech Megafuge 1.0. The pellet is resuspended in 10–20 vol. Hepes buffer (20 mM Hepes, 5 mM $MgCl_2$, pH 7.1 (KOH)) and homogenized for 10–20 seconds using an Ultra-Turrax homogenizer. The homogenate is centrifuged for 30 min at 23 000 g. The pellet is resuspended in 5–10 ml Hepes buffer, homogenized 5–10 seconds with the Ultra-Turrax and centrifuged for 10 min at 23 000 g. Following this centrifugation step, the membrane pellet is resuspended in 2–4 ml Hepes buffer, homogenized with a syringe or Teflon homogenizer, and the protein concentration determined. The membranes are diluted to a protein concentration of 1–5 mg/ml in Hepes buffer, aliquoted and kept at −80° C. until use.

Aliquots of the membrane suspension are incubated for 60 min at 25° C. with 30 pM [$^{125}$I]-iodoproxifan, a known compound with high affinity for the H3 receptor, and the test compound at various concentrations. The incubation is stopped by dilution with ice-cold medium, followed by rapid filtration through Whatman GF/B filters pretreated for 1 hour with 0.5% polyethyleneimine. The radioactivity retained on the filters is counted using a Cobra II auto gamma counter. The radioactivity of the filters is indirectly proportional to the binding affinity of the tested compound. The results are analysed by nonlinear regression analysis. When tested, the present compounds of the formula (I) generally show a high binding affinity to the histamine H3 receptor.

Preferably, the compounds according to the invention have an $IC_{50}$ value as determined by one or more of the assays of less than 10 μM, more preferred of less than 1 μM, and even more preferred of less than 500 nM, such as of less than 100 nM.

Functional Assay I

The ability of the compounds to interact with the histamine H3 receptor as agonists, inverse agonists and/or antagonists, is determined by an in vitro functional assay utilizing membranes from HEK 293 cell expressing the human H3 receptors.

The H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM with glutamax, 10% foetal calf serum, 1% penicillin/streptavidin and 1 mg/ml G 418 at 37° C. and 5% $CO_2$.

The H3 receptor expressing cells are washed once with phosphate buffered saline (PBS) and harvested using versene (GIBCO-BRL). PBS is added and the cells are centrifuged for 5 min at 188 g. The cell pellet is resuspended in stimulation buffer to a concentration of 1×10$^6$ cells/ml. cAMP accumulation is measured using the Flash Plate® cAMP assay (NEN™ Life Science Products). The assay is generally performed as described by the manufacturer.

Briefly, 50 μl cell suspension is added to each well of the Flashplate which also contained 25 μl 40 μM isoprenaline, to stimulate cAMP generation, and 25 μl of test compound (either agonists or inverse agonists alone, or agonist and antagonist in combination). The assay can be run in "agonist-mode" which means that the test compound is added, in increasing concentration, on its own, to the cells, and cAMP is measured. If cAMP goes up, it is an inverse agonist; if cAMP does not change, it is a neutral antagonist, and if cAMP goes down, it is an agonist. The assay can also be run in the "antagonist-mode" which means that a test compound is added, in increasing concentrations, together with increasing concentrations of a known H3 agonist (e.g. RAMHA). If the compound is an antagonist, increasing concentrations of it cause a right-ward shift in the H3-agonist's dose-response curves. The final volume in each well is 100 μl. Test compounds are dissolved in DMSO and diluted in $H_2O$. The mixture is shaken for 5 min, and allowed to stand for 25 min at room temperature. The reaction is stopped with 100 μl "Detection Mix" per well. The plates are then sealed with plastic, shaken for 30 min, allowed to stand overnight, and finally the radioactivity is counted in the Cobra II auto gamma topcounter. $EC_{50}$ values are calculated by non-linear regression analysis of dose response curves (6 points minimum) using GraphPad Prism. Kb values are calculated by Schild plot analysis.

Functional Assay II

The ability of the compounds to bind and interact with the human H3 receptor as agonists, inverse agonists and/or antagonists, is determined by a functional assay, named [$^{35}$S] GTPγS assay. The assay measures the activation of G proteins by catalyzing the exchange of guanosine 5'-diphosphate (GDP) by guanosine 5'-triphosphate (GTP) at the α-subunit. The GTP-bounded G proteins dissociate into two subunits, $Gα_{GTP}$ and Gβγ, which in turn regulate intracellular enzymes and ion channels. GTP is rapidly hydrolysed by the Gα-subunit (GTPases) and the G protein is deactivated and ready for a new GTP exchange cycle. To study the function of ligand induced G protein coupled receptor (GPCR) activation by an increase in guanine nucleotide exchange at the G proteins, the binding of [$^{35}$S]-guanosine-5'-O-(3-thio) triphosphate [$^{35}$S] GTPγS, a non-hydrolysed analogue of GTP, is determined. This process can be monitored in vitro by incubating cell membranes containing the G protein coupled receptor H3 with GDP and [$^{35}$S] GTPγS. Cell membranes are obtained from CHO cells stably expressing the human H3 receptor. The cells are washed twice in PBS, harvested with PBS+1 mM EDTA, pH 7.4 and centrifuged at 1000 rpm for 5 min. The cell pellet is homogenized in 10 ml ice-cold Hepes buffer (20 mM Hepes, 10 mM EDTA pH 7.4 (NaOH)) using an Ultra-Turrax homogenizer for 30 seconds and centrifuged for 15 min at 20.000 rpm. Following this centrifugation step, the membrane pellet is resuspended in 10 ml ice-cold Hepes buffer (20 mM Hepes, 0.1 mM EDTA pH 7.4 (NaOH)) and homogenized as describe above. This procedure is repeated twice except for the last homogenization step, the protein concentration is determined and membranes are diluted to a protein concentration at 2 mg/ml, aliquoted and kept at −80° C. until use.

In order to study the presence and the potency of an inverse agonist/antagonist the H3-receptor agonist ligand R-α-methyl histamine (RAMHA) is added. The ability of the test compound to counteract the effect of RAMHA is measured. When studying the effect of an agonist RAMHA is not added to the assay medium. The test compound is diluted in the assay buffer (20 mM HEPES, 120 mM NaCl, 10 mM $MgCl_2$ pH 7.4 (NaOH)) at various concentrations followed by addition of $10^{-8}$ nM RAMHA (only in the case where an inverse agonist/antagonist is examined), 3 μM GDP, 2.5 μg membranes, 0.5 mg SPA beads and 0.1 nM [$^{35}$S] GTPγS and incubated for 2 hours by slightly shaking at room temperature. The plates are centrifuged at 1500 rpm for 10 min and the radioactivity is measured using a Topcounter. The results are analyzed by non linear regression and the $IC_{50}$ value is determined. RAMHA and other H3 agonists stimulate the binding of [$^{35}$S] GTPγS to membranes expressing the H3 receptor. In the antagonist/inverse agonist test, the ability of increasing amounts of test compound to inhibit the increased [$^{35}$S] GTPγS binding by $10^{-8}$ M RAMHA is measured as a decrease in radioactivity signal. The $IC_{50}$ value determined for an antagonist is the ability of this compound to inhibit the effect of $10^{-8}$M RAMHA by 50%. In the agonist test, the ability of increasing amounts of test compound is measured as an increase in radioactivity signal.

The $EC_{50}$ value determined for an agonist, is the ability of this compound to increase the signal by 50% of the maximal signal that is obtained by $10^{-5}$ M RAMHA.

Preferably, the antagonists and agonists according to the invention have an $IC_{50}/EC_{50}$ value as determined by one or more of the assays of less than 10 μM, more preferred of less than 1 μM, and even more preferred of less than 500 nM, such as of less than 100 nM.

The Open Cage Schedule-Fed Rat Model

The ability of the present compounds to reduce weight is determined using the in vivo open cage Schedule-fed rat model.

Sprague-Dawley (SD) male rats of an age of about 1½ to 2 months and a weight of about 200–250 g are purchased from Møllegård Breeding and Research Centre A/S (Denmark). On arrival they are allowed some days of acclimatisation before being placed in individual open plastic cages. They are habituated to the presence of food (Altromin pelleted rat chow) in their home cage only during 7 hours in the morning from 07.30 to 14.30 all days a week. Water is present ad libitum. As the consumption of food has stabilised after 7 to 9 days, the animals are ready for use.

Each animal is used only once to avoid carry-over effects between treatments. During the test sessions, the test compound is administered intraperitoneally or orally 30 min before the start of the sessions. One group of animals is administered the test compound at different doses and a control group of animals is given a vehicle. Food and water intake are monitored at 1, 2 and 3 hours post administration.

Any side effects may rapidly be discovered (barrel-rolling, bushy fur etc.) since the animals are kept in transparent plastic cages to enable continuous monitoring.

What is claimed is:

1. A compound of formula (II):

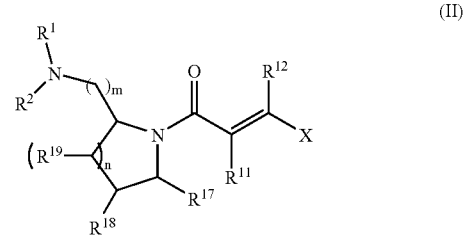

wherein m is 1, 2 or 3, n is 1, or 2, wherein, when n is 1, R¹ and R² together form a C₅-alkylene bridge, which may optionally be substituted with one or more substituents selected from halogen and hydroxyl; and when n is 2, R¹ and R² together form a C₄-alkylene bridge, which may optionally be substituted with one or more substituents selected from halogen and hydroxyl;

R¹¹ and R¹² independently are hydrogen,

C₁₋₆-alkyl, which may optionally be substituted with one or more substituents selected from C₃₋₈-cycloalkyl, C₅₋₈-cycloalkenyl, halogen and hydroxyl, or C₃₋₈-cycloalkyl or C₅₋₈-cycloalkenyl, which may optionally be substituted with one or more substituents selected from halogen and hydroxyl,

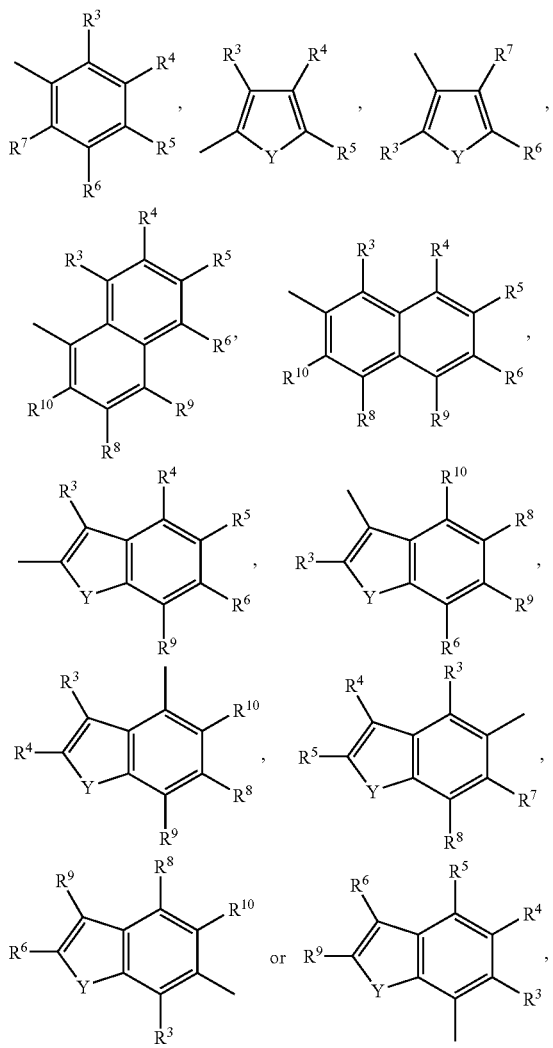

R³, R⁴, R⁵, R⁶, R⁷, R⁸, R⁹ and R¹⁰ independently are hydrogen, halogen, cyano, —NR¹⁵R¹⁶, hydroxyl, carbamoyl, carboxyl, —CF₃, —OCF₃, carboxyl, amidino, guanidino or nitro, or C₁₋₆-alkoxy, C₁₋₆-alkyl, C₁₋₇-alkanoyl, C₁₋₆-alkylcarbamoyl, di-C₁₋₆-alkylcarbamoyl, C₁₋₆-alkyloxycarbonyl, C₃₋₈-cycloalkyl, C₃₋₈cycloalkanoyl, C₃₋₈-cycloalkylcarbamoyl, C₃₋₈-cycloalkyl-oxycarbonyl, C₁₋₆-alkylthio, C₁₋₆-alkylsulfinyl, C₁₋₆-alkylsulfonyl, C₁₋₆-alkylsulfonyl-O—, aryl, aroyl, aryloxy, aryloxycarbonyl, heteroaryl, heteroaroyl, or heteroaryloxy which may optionally be substituted with one or more substituents selected from halogen, hydroxyl, cyano and —NR¹⁵R¹⁶, R¹⁵ and R¹⁶ independently are hydrogen or carbamoyl, C₁₋₆-alkyl, which may optionally be substituted with, one or more substituents selected from C₃₋₈-cycloalkyl, C₅₋₈-cycloalkenyl, halogen, hydroxyl, cyano and amino, or C₃₋₈-cycloalkyl, C₅₋₈-cycloalkenyl, C₁₋₆-alkylcarbamoyl, di-C₁₋₆-alkylcarbamoyl or C₁₋₆-alkyloxycarbonyl, which may optionally be substituted with one or more substituents selected from halogen, hydroxyl, cyano, amino, C₁₋₆-alkyl, C₂₋₆-alkenyl and C₂₋₆-alkynyl, or R¹⁵ and R¹⁶ together form a C₃₋₆-alkylene bridge or a C₃₋₆-alkenylene bridge, which may optionally be substituted with one or more substituents selected from halogen and hydroxyl, or two or more of R³ and R⁴, R⁴ and R⁵, R⁵ and R⁶, R⁶ and R⁷, R⁷ and R⁸, R⁸ and R⁹, R⁹ and R⁶, and R⁸ and R¹⁰ together form a bridge selected from —OCH₂O—, —OCH₂CH₂O—, —OCH₂CH₂CH₂O— and C₃₋₅-alkylene, or R¹¹ and R³, R¹¹ and R⁷, or R¹¹ and R¹⁰ together form a bridge selected from —O—, —S—, —CH₂—, —C(=O)—, —CH(OH)—, —NR¹³—, —OCH₂— and —CH₂O—, R¹³ is hydrogen, C₁₋₆-alkyl, which may optionally be substituted with one or more substituents selected from C₃₋₈-cycloalkyl, C₅₋₈-cycloalkenyl, halogen, hydroxyl, cyano and amino, C₃₋₈-cycloalkyl or C₅₋₈-cycloalkenyl, which may optionally be substituted with one or more substituents selected from halogen, hydroxyl, cyano, amino, C₁₋₆-alkyl, C₂₋₆-alkenyl and C₂₋₆-alkynyl, —Y— is —CH₂—, —C(=O)—, —NR¹⁴—, —O—, —S—, —CH₂O—, —OCH₂— or —CH(OH)—, R¹⁴ is hydrogen, C₁₋₆-alkyl, which may optionally be substituted with one or more substituents selected from C₃₋₈-cycloalkyl, C₅₋₈-cycloalkenyl, halogen, hydroxyl, cyano and amino, C₃₋₈-cycloalkyl or C₅₋₈-cycloalkenyl, which may optionally be substituted with one or more substituents selected from halogen, hydroxyl, cyano and amino, R¹⁷ is hydrogen, C₁₋₆-alkyl, C₂₋₆-alkenyl or C₂₋₆-alkynyl, R¹⁸ and R¹⁹ independently are hydrogen, halogen, hydroxyl, amino, C₁₋₆-alky, C₂₋₆-alkenyl or C₂₋₆-alkynyl, as well as any diasteromer or enantiomer or tautomeric form thereof, mixtures of these or a pharmaceutically acceptable salt thereof.

2. A compound according to claim 1 wherein m is 1.

3. A compound according to claim 1 wherein X is.

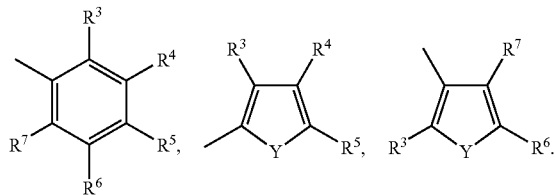

4. A compound according to claim 1 wherein —Y— is —O— or —S—.
5. A compound according to claim 4 wherein —Y— is —O—.
6. A compound according to claim 3 wherein X is.

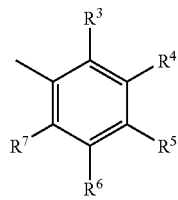

7. A compound according to any claim 1 wherein $R^3$, $R^4$, $R^5$, $R^6$ and $R^7$ are independently selected from
hydrogen, halogen, cyano, —$NR^{15}R^{16}$, —$CF_3$, —$OCE_3$, or nitro,
$C_{1-6}$-alcoxy, $C_{3-6}$-cycloalkyl-carbonyl, aryl, heteroaryl, $C_{3-8}$-cycloalkanoyl, $C_{1-6}$-alkylsulfonyl, or $C_{1-6}$-alkylsulfonyl-O— which may optionally be substituted with one or more halogen
or $R^4$ and $R^5$ together form a —$OCH_2O$— bridge,
or $R^{11}$ and $R^3$ together form a bridge selected from —O— or —S—.
8. A compound according to claim 7 wherein $R^3$, $R^4$, $R^5$, $R^6$ and $R^7$ are independently selected from
hydrogen, halogen, cyano, —$CF_3$, or —$OCF_3$
$C_{1-6}$-alkoxy, 1,2,4-triazolyl, cyclopropanoyl or $C_{1-6}$-alkylsulfonyl-O— which may optionally be substituted with one or more halogen
or $R^4$ and $R^5$ together form a —$OCH_2O$— bridge,
or $R^{11}$ and $R^3$ together form a bridge selected from —O— or —S—.
9. A compound according to claim 8 wherein $R^3$, $R^4$, $R^5$, $R^6$ and $R^7$ are independently selected from
hydrogen, halogen, cyano, —$CF_3$, or —$OCF_3$
—O—$CH_3$, 1,2,4-triazolyl, —O—$CH_2CH_3$, or $CH_3$-sulfonyl-O— which may optionally be substituted with one or more halogen
or $R^{11}$ and $R^3$ together form a bridge selected from —O— or —S—.
10. A compound according to claim 9 wherein $R^3$, $R^4$, $R^5$, $R^6$ and $R^7$ are independently selected from
hydrogen, halogen, cyano, —$CF_3$, or —$OCF_3$
—O—$CH_3$, —O—$CH_2CH_3$, or $CH_3$-sulfonyl-O— or $CF_3$-sulfonyl-O—
or $R^{11}$ and $R^3$ together form a bridge selected from —O— or —S—.
11. A compound according to claim 1 wherein $R^{11}$ is hydrogen.
12. A compound according to claim 1 wherein $R^{12}$ is hydrogen or $C_{1-6}$-alkyl.
13. A compound according to claim 12 wherein $R^{12}$ is hydrogen or methyl.
14. A compound according to claim 1 wherein $R^{15}$ is hydrogen.
15. A compound according to claim 1 wherein $R^{16}$ is hydrogen.
16. A compound according to claim 1 wherein $R^{17}$, $R^{18}$ and $R^{19}$ are all hydrogen.
17. A compound according to claim 1, wherein n is 1.
18. A compound according to claim 1, wherein n is 2.
19. A pharmaceutical composition comprising at least one compound according to claim 1 together with one or more pharmaceutically acceptable carriers or excipients.
20. A pharmaceutical composition according to claim 19 in unit dosage form, said compositon comprising from about 0.05 mg to about 1000 mg of said compound.
21. A pharmaceutical composition according to claim 19 in unit dosage form, said composition comprising from about 0.1 mg to about 500 mg of said compound.
22. A pharmaceutical composition according to claim 19 in unit dosage form, said composition comprising from about 0.5 mg to about 200 mg of said compound.
23. A method for the treatment of disorders or diseases selected from the following: obesity, overweight, impaired glucose tolerance (IGT), type 1 diabetes, type 2 diabetes, dyslipidemia, progression from IGT to type II diabetes, and progression of non-insulin-requiring type II diabetes to insulin-requiring type II diabetes comprising administering to a subject in need thereof an effective amount of a compound according to claim 1.
24. The method according to claim 23 wherein the effective amount of the compound is in the range of from about 0.05 mg to about 2000 mg per day.
25. The method according to claim 23 wherein the effective amount of the compound is in the range of from about 0.1 mg to about 1000 mg per day.
26. The method according to claim 23 wherein the effective amount of the compound is in the range of from about 0.5 mg to about 500 mg per day.
27. A method according to claim 23, wherein the disorder or disease is selected from impaired glucose tolerance and type II diabetes.
28. A method according to claim 23, wherein the disorder or disease is selected from: progression from IGT to type II diabetes, and progression of non-insulin-requiring type II diabetes to insulin-requiring type II diabetes.
29. A method according to claim 23, wherein the disorder or disease is selected from: obesity and overweight.
30. A method according to claim 23, wherein the disorder or disease is dyslipidemia.

* * * * *